US005846773A

United States Patent [19]
Lee et al.

[11] Patent Number: 5,846,773
[45] Date of Patent: Dec. 8, 1998

[54] SINGLE GENE ENCODING AORTIC-SPECIFIC AND STRIATED-SPECIFIC MUSCLE CELL ISOFORMS AND USES THEREOF

[75] Inventors: Mu-En Lee, Newton; Chung-Ming Hsieh, Boston, both of Mass.

[73] Assignee: President and Fellows of Harvard College, Cambridge, Mass.

[21] Appl. No.: 795,868

[22] Filed: Feb. 6, 1997

Related U.S. Application Data

[63] Continuation-in-part of Ser. No. 494,577, Jun. 22, 1995.

[51] Int. Cl.[6] ............................ C12P 21/02; C12N 15/85; C12N 15/11; C07H 21/04
[52] U.S. Cl. .................... 435/69.1; 435/70.1; 435/320.1; 435/325; 536/23.1; 536/24.1
[58] Field of Search ............................. 435/69.1, 320.1, 435/70.1, 325; 536/23.1, 24.1

[56] References Cited

PUBLICATIONS

Blobel et al., "Structure, Function and Evolutionary Relationship of Proteins Containing a Distintegrin Domain", *Curr. Opin. Cell Biol.*, 4:760–65 (1992).

Del Sal et al., "The Growth Arrest–Specific Gene, gas1, Is Involved in Growth Suppression", 1992, *Cell*,70:595–607 (1992).

Gallagher et al., "The Carboxyl Terminus of the Smooth Muscle Myosin Light Chain Kinase Is Expressed as an Independent Protein, Telokin", *J. Biol. Chem.*, 266:23945–52 (1991).

Gorski et al., "Molecular Cloning of a Diverged Homeobox Gene That Is Rapidly Down–Regulated During the $G_0/G_1$ Transition in Vascular Smooth Muscle Cells", *Mol. And Cell. Biol.*, 13:3722–33 (1993).

Holden, et al., "X–ray Structure Determination of Tekokin, the C–terminal Domain of Myosin Light Chain Kinase, at 2.8 Å Resolution", *J. Mol. Biol.*, 277:840–51 (1992).

Hunter et al., "Targeting Gene Expression to Specific Cardiovascular Cell Types in Transgenic Mice", *Hypertension*, 22:608–17 (1993).

Hynes, "Integrins: Versatility, Modulation, and Signaling in Cell Adhesion", *Cell*, 69:11–25 (1992).

Kozak, "At Lease Six Nucleotides Preceding the AUG Initiator Codon Enhance Translation in Mammalian Cells", *J. Mol. Biol.*, 196:947–50 (1987).

Leco et al., "Tissue Inhibitor of Metalloproteinases–3 (TIMP–3) Is an Extracellular Matrix–associated Protein with a Distinctive Pattern of Expression in Mouse Cells and Tissues", *J. Biol. Chem.*, 269:9352–60 (1994).

Pauly et al., "Experimental Models That Mimic the Differentiation of Vascular Cells", *Circulation* (*Supp III*), 86:III–68–73 (1992).

Hsieh et al., "APEG–1, a Novel Gene Preferentially Expressed in Aortic Smooth Muscle Cells, is Down–regulated by Vascular Injury," *FASEB J.*, 10:6, p. A1012, No. 74 (1996).

Hsieh et al., "APEG–1, A Novel Gene Preferentially Expressed In Aortic Smooth Muscle Cells, is Down–regulated by Vascular Injury," *J. Biol. Chem.* (*Microfilms*) 271(29):17354–59 (1996).

McGeoch et al., "Complete DNA Sequence of the Short Repeat Region in the Genome of Herpes Simplex Virus Type I," *Nucleic Acids Research* 14(4):1727–1745 (1986).

EMBL EST, Accession No. R24327, Sequence reference yg32f04.rl, 23–Apr–1995, *Homo sapiens* cDNA clone 33988 5'XP002014921.

EMBL EST, Accession No. W55328, Sequence reference mb12e01.rl, 06–Jun–1996, Life Tech mouse brain, *Mus musculus* cDNA clone 319992 5'XP002014922.

Ross, "The Pathogenesis of Atherosclerosis: A Perspective for the 1990s", *Nature*, 362:801–809 (1993).

Ruoslahti et al., "New Perspectives in Cell Adhesion: RGD and Integrins", *Science*, 238:491–96 (1987).

Shanahan et al., "Isolation of Gene Markers of Differentiated and proliferating Vascular Smooth Muscle Cells", *CIRCULATION RES.*, 73:193–204 (1993).

Sun et al., "Molecular Cloning of Five Messenger RNAs Differentially Expressed in Preneoplastic or Neoplastic JB6 Mouse Epidermal Cells: One Is Homologous to Human Tissue Inhibitor of Metalloproteinases–3", *Cancer Res.*, 54;1139–44.

*Primary Examiner*—Nancy Degen
*Attorney, Agent, or Firm*—Fish & Richardson P.C.

[57] ABSTRACT

Aortic-preferentially-expressed gene-1 (APEG-1) and striated muscle preferentially expressed (SPEG) polypeptide, DNA sequences encoding and controlling the transcription of the APEG-1/SPEG encoding gene, methods of diagnosing vascular injury, methods of conferring smooth muscle-cell specific expression, and methods of inhibiting vascular smooth muscle cell proliferation by increasing the level of APEG-1 at the site of vascular injury.

8 Claims, 24 Drawing Sheets

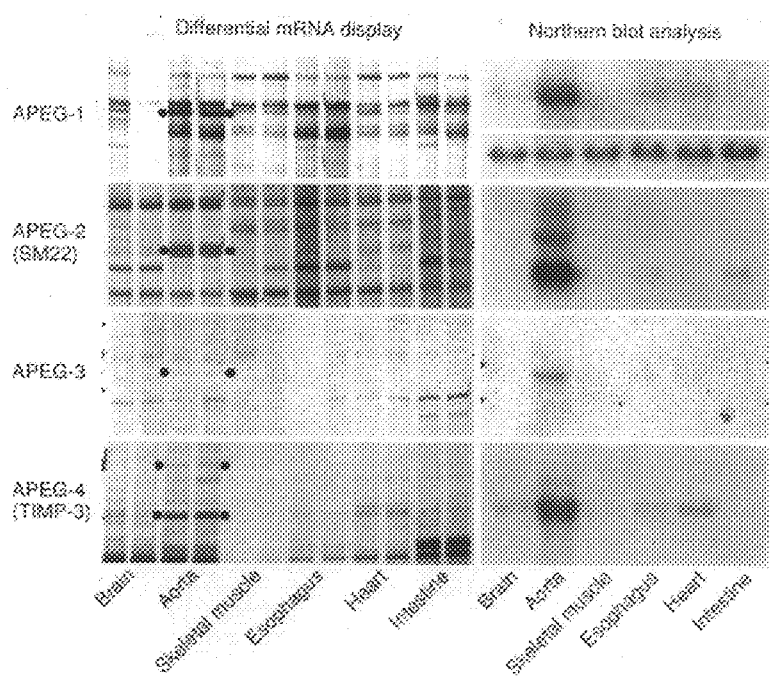

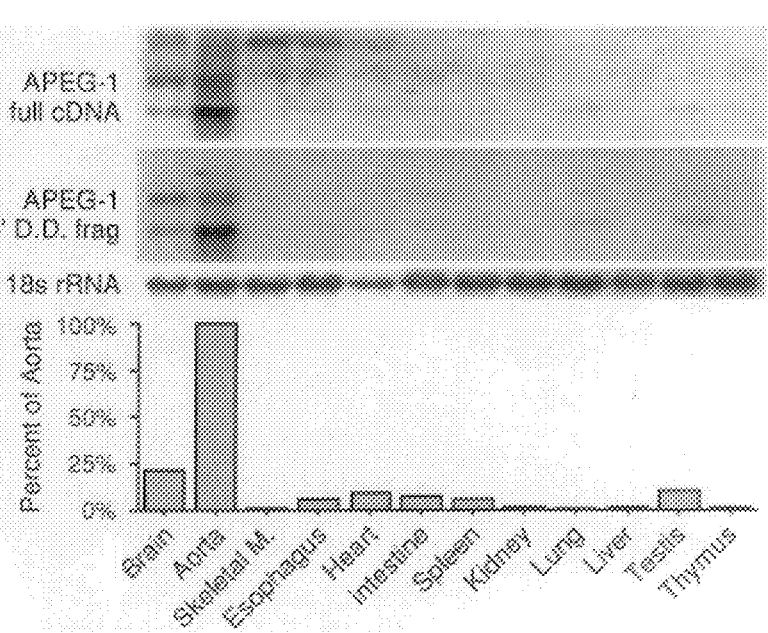
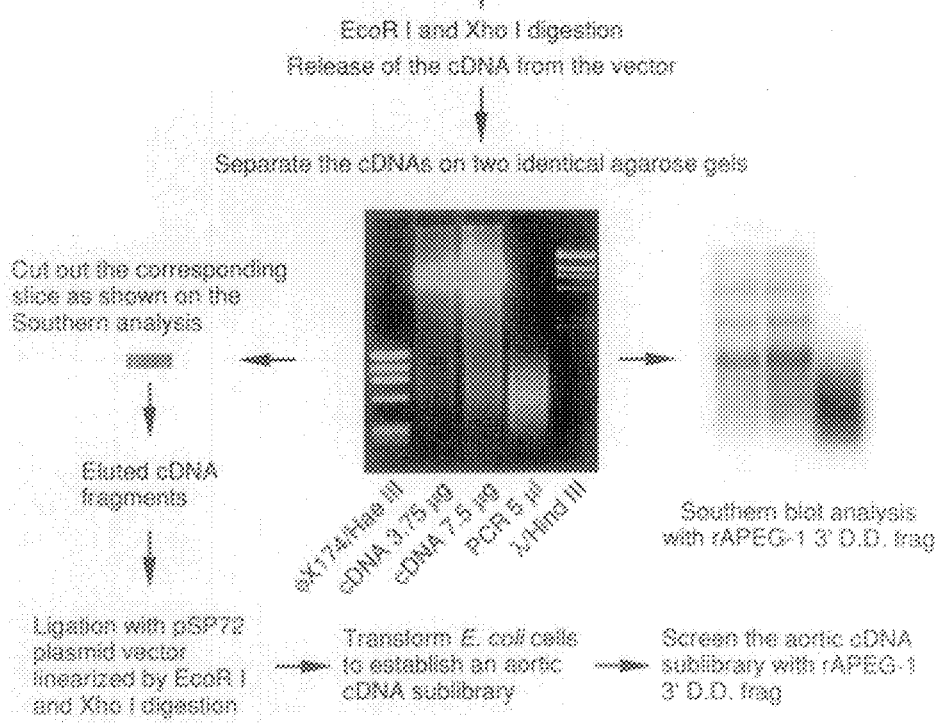
FIG. 4

1     gaattcggcacgagagcagagacttaaggaaggtgcagacgggtccgtttgcacagcctcagggcgcgtcc
71    acatccccttcagcagcccaatcacctctgatgaggagtacctgagccccccagaggagttcccagaac
141   ctggggagacctggtcccgaaCCCtACCAGTCCCAGCCAGGATCGAGATTCCTCTGACTC
211   TTCCTCCAAGGCACCCCCAACCTTCAAGTCTCACTCAGTGACCAATCAGTGAGAGAAGGTCAAGATGTC
281   ATTATGAGCATCCGCGTGCAGGGGAGCCCAAGCCTCTGGTCTCCTGGCTGAGGAATCGGCAGCCTGTGC
351   GCCCAGACCAGCGCGCTTTGCAGAGAGGCCGAGGGGTGGCTCTGCCGGTTGAGGATCCTGGCTGCTGA
421   GAGGGGAGATGCTGGTTTCTACACTTGCAAGGCGGTCAACGAATATGGCGCTCGGCAGTGTGAGGCCCGC
491   CTGGAGGTCCGAGGCGAGTGAgctcaggggccacctgcgctgcctcctcgagctgcaccccc
561   tgtctcagcgcacctcctgactcgctgtgttcactgcccacagaccggctcgccgg
631   cccgacatagcccatgtctcccctccctagcccacagcacccctgggtaaccatcgggcccc
701   tgtggatccctcccccaagtggatatgtggctgtgcagaccaggcccccagaaggactgagtgtt
771   gagaaggatggtcatgagggttgtgacaaggccactgtctgtctctctgtcctgtctgtgacagt
841   aatgcatgtgctatgctgctacaggccactgtctgtctgcctgtctgtgacagt
911   cagggaagaaaaccttCGAGCTGaggtgggataagacagaataagatagaacacagcatctgtgaga
981   tgcagggcccagagggcaggcacagtggcacaacattttattccacatgagaccaaaagctagaggtctgggattaa
1051  agaaatgggttttaaatgcaagcttaggaccaagtggggtaccccttcttcacagacacatccgacacgctctgt
1121  gccctgactgctgagagtagcagactgagcagcaggagcacaggtcatagtgggactgggagtttggaaacact
1191  ctgggaatgagagtagcagactgagcagcaggtcatagtgggactgggagtttggaaacact
1261  atttcgtagctcaataagtccagtttgtacccaaaaaaaaaaaaa    SEQ ID NO:1

FIG. 5

```
  1   ATG AAG CCC AGT CCC AGC CAG GAT CGA GAT TCC TCT GAC TCT TCC AAG
      Met Lys Pro Ser Pro Ser Gln Asp Arg Asp Ser Ser Asp Ser Ser Lys

18   GCA CCC CCA ACC TTC AAG GTC TCA CTC ATG GAC CAA GTG AGA GAA GGT
      Ala Pro Pro Thr Phe Lys Val Ser Leu Met Asp Gln Val Arg Glu Gly

35   CAA GAT GTC ATT ATG AGC ATC CGC GTG CAG CCT GTG CGC CCA AAG GTC
      Gln Asp Val Ile Met Ser Ile Arg Val Gln Pro Val Arg Pro Lys Val

52   TCC TGG CTG AGG AAT CGG CAG CCT GTG CGC CCA GAC CCA AAG CCT GTC
      Ser Trp Leu Arg Asn Arg Gln Pro Val Arg Pro Asp Pro Lys Pro Val

69   GAG GAG GCC GAG GGT GGG GGG CTC TGC CGG TTG AGG ATC CTG GCT GAG AGG
      Glu Glu Ala Glu Gly Gly Gly Leu Cys Arg Leu Arg Ile Leu Ala Glu Arg

86   GGA GAT GCT GGT TTC TAC ACT TGC AAG GCG GTC AAC GAA TAT GGC GCT CGG
      Gly Asp Ala Gly Phe Tyr Thr Cys Lys Ala Val Asn Glu Tyr Gly Ala Arg

103   CAG TGT GAG GCC CGC CTG GAG GCC CGA GGC GAG GTC CGA GGC GAG TGA
      Gln Cys Glu Ala Arg Leu Glu Ala Arg Gly Glu Val Arg Gly Glu ***
```

SEQ ID NO:2
SEQ ID NO:3

FIG. 6

| | | | | | | |
|---|---|---|---|---|---|---|
| ChkTelo | MAMISGMSGR | KASGSSPTSP | INADKVENED | ....AFLEEV | AEEKPHVKPY | FTKTILDMEV |
| ChkMLCK | MAMISGMSGR | KASGSSPTSP | INADKVENED | ....AFLEEV | AEEKPHVKPY | FTKTILDMEV |
| RabTelo | MAMISGLSGR | KSSTGSPTSP | LTAERLETEE | DVSQAFLEAV | AEEKPHVKPY | FSKTIRDLEV |
| RabMLCK | MAMISGLSGR | KSSTGSPTSP | LTAERLETEE | DVSQAFLEAV | AEEKPHVKPY | FSKTIRDLEV |
| APEG-1 | MKPSPSQDR | DSSDSSSKAP | | | ....PT | FKVSLMDQSV |
| Consensus | -----S----R | --S---S----P | ---------- | ---------- | ------P- | F-----D---V |

| | | | | | | |
|---|---|---|---|---|---|---|
| ChkTelo | VEGSAARFDC | KIEGYPDPEV | MWYKDDQPVK | ESRHFQIDYD | EEGNCSLTIS | EVCGDDDAKY |
| ChkMLCK | VEGSAARFDC | KIEGYPDPEV | MWYKDDQPVK | ESRHFQIDYD | EEGNCSLTIS | EVCGDDDAKY |
| RabTelo | VEGSAARFDC | KIEGYPDPEV | VWFKDDQSIR | ESRHFQIDYD | EDGNCSLIIS | DVCGDDDAKY |
| RabMLCK | VEGSAARFDC | KIEGYPDPEV | VWFKDDQSIR | ESRHFQIDYD | EDGNCSLIIS | DVCGDDDAKY |
| APEG-1 | REGQDVIMSI | RVQGEPKPVV | SWLRNRQPVR | PDQRRFAEEA | EGGLCRLRIL | AAERGDAGFY |
| Consensus | -EG------ | ---G-P-P-V | -W-----Q-- | ---------- | E-G-C-L-I- | -----D---Y |

| | | | | | |
|---|---|---|---|---|---|
| ChkTelo | TCKAVNSLGE | ATCTAELLVE | TMGKEGEGEG | EGEEDEEEEE | E | SEQ ID NO:4 |
| ChkMLCK | TCKAVNSLGE | ATCTAELLVE | TMGKEGEGEG | EGEEDEEEEE | E | SEQ ID NO:5 |
| RabTelo | TCKAVNSLGE | ATCTAELIVE | TME.EGEGEG | EEEEEE | | SEQ ID NO:6 |
| RabMLCK | TCKAVNSLGE | ATCTAELIVE | TME.EGEGEG | EEEEEE | | SEQ ID NO:7 |
| APEG-1 | TCKAVNEYGA | RQCEARLEVR | GE | | | SEQ ID NO:8 |
| Consensus | TCKAVN--G- | --C-A-L-V- | ---------- | ---------- | - | SEQ ID NO:9 |

FIG. 8

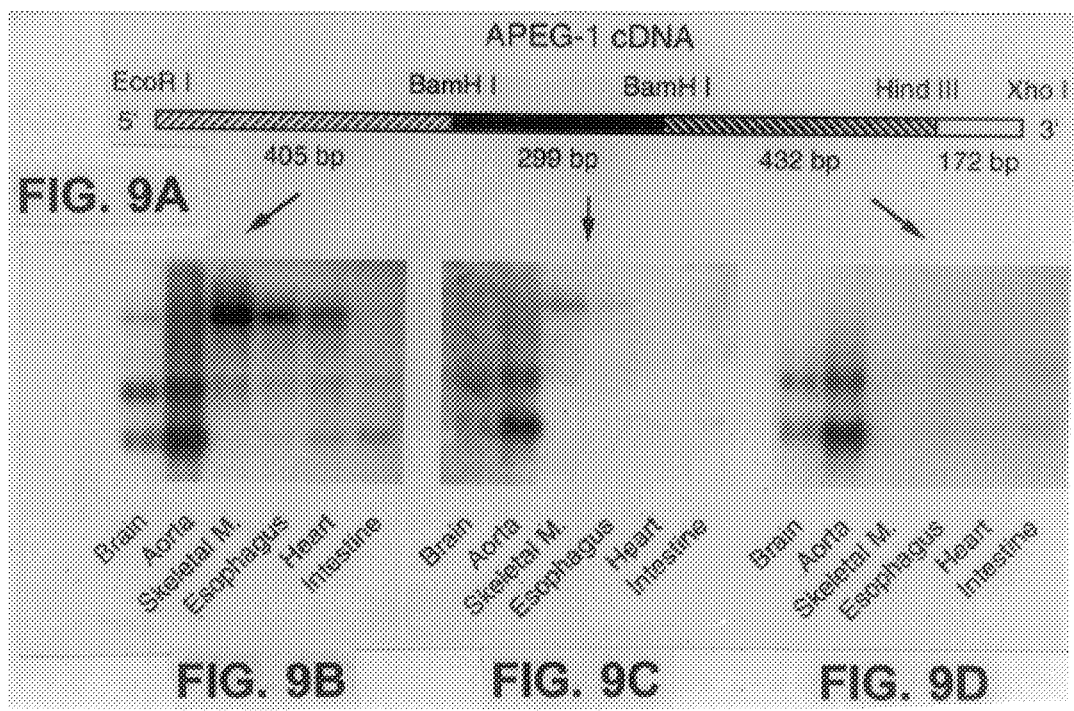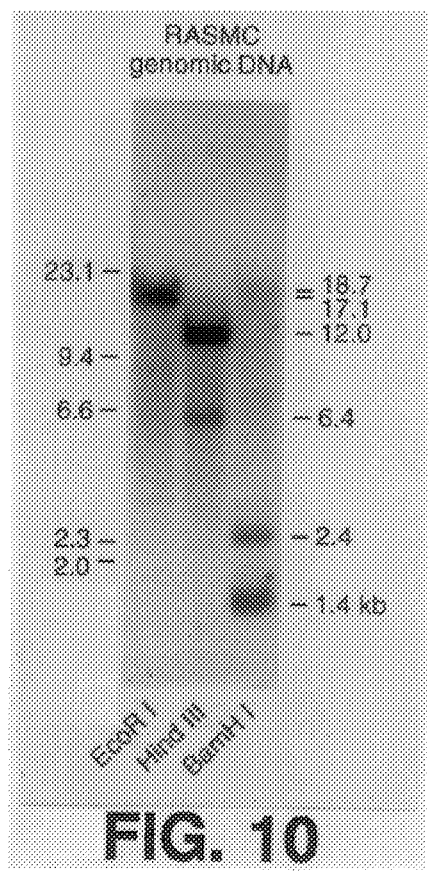

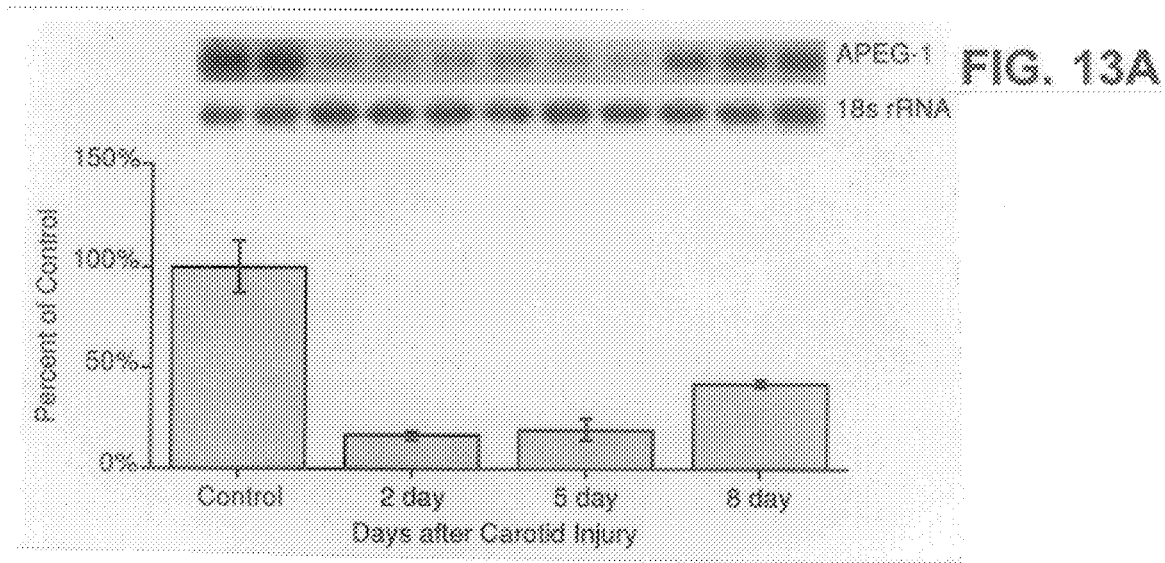
FIG. 13A
FIG. 13B
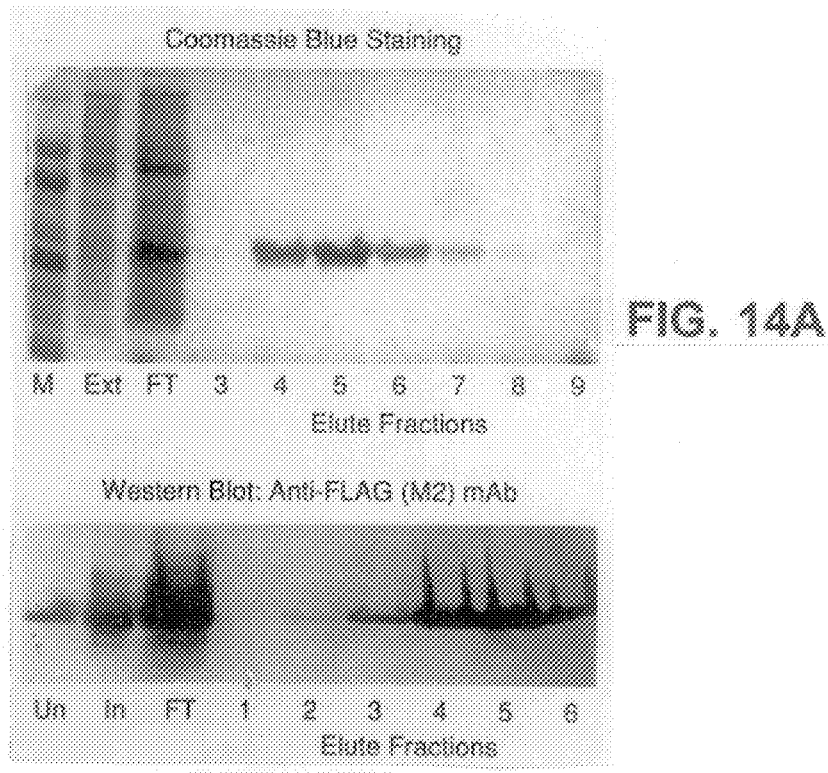
FIG. 14A
FIG. 14B

APEG-1 cDNA Sequence

```
   1  TCACCTCTGA TGAGGAATAC CTGAGCCCCC CAGAGGAGTT CCCAGAGCCT
  51  GGGGAGACCT GGCCGCGAAC CCCCACCATG AAGCCCAGTC CCAGCCAGGA
 101  CCGCCGTTCT TCTGACACTG GCTCCAAGGC ACCCCCCACC TTCAAGGTCT
 151  CACTTATGGA CCAGTCAGTA AGAGAAGGCC AAGATGTCAT CATGAGCATC
 201  CGCGTGCAGG GGGAGCCCAA GCCTGTGGTC TCCTGGCTGA GAAACCGCCA
 251  GCCCGTGCGC CCAGACCAGC GGCGCTTTGC GGAGGAGGCT GAGGGTGGGC
 301  TGTGCCGGCT GCGGATCCTG GCTGCAGAGC GTGGCGATGC TGGTTTCTAC
 351  ACTTGCAAAG CGGTCAATGA GTATGGTGCT CGGCAGTGCG AGGCCCGCTT
 401  GGAGGTCCGA GGCGAGTGAG CTCAGGGGGC CACCTGCGCT CCCCCCGCTA
 451  CCCTCCGAGC CGCGCCCCTG TCTCAGGCAC CTCTCGGACC TCGCTGTGTT
 501  TCACTGCCTC CTGCCCACAG ACCCAGGCCT GCCGGCCCGG ACCCGTCCCA
 551  GCCTCCCCTC CCCACCCCAT GCAGCCCCCA GGGGGATAGC CCATGGGCCC
 601  CTGTGGACAC TCCCTCCCCA AGTGGACACA TGGCTGTGCA GGCCAGGAGG
 651  CCCACAGATG GACTGAGTGC TGGGAAGGGG CGGCTTCGAG GGTATCAAC
 701  CCCCCGAGTC TCTCCCTGAA GGGGAGCACC GGGCGAGTGC ATGTGCTACT
 751  GCTGCTACAG GCCTGTCTAT CTGTTTGTCT GTCTGTGTGT CTGTGACAGT
 801  CAGGGAAGGA TGCCTCGGAG CTGAGGTGGG GTGAGACAGA GTGGGAGAGA
 851  TTACGGCATG GCATGGAGGG GCCCAAGGAG CAGGGGCTGT TGACAAAGGC
 901  CTTACCAGGA AGGGTTAGGA CACTGACCAT TCTAGAAATG GGTTTCGAAT
 951  GGCACAACAC TTTCTATTTC ACAAAAGACC AAAAGCCAGA GGCCCCAGGC
1001  TCTGTGCTGA TGAACAGCCT GGCTGAGCCC TGGCCCTGGC AGGTTTAGGG
1051  CCCATTTGGG GCCCCCTCCT TCTCTGTCAG GGCTGGGGTG CTCTGTCTGG
1101  GAATGAGGGA GTTAACCAAG TTTGGTGCAG GAGCAGGGGC AGGGGGCCAC
1151  TGTAGTGAGC GTGGATGAAA TTTGGANACA CCTATNTCTT AANTCAAATA
1201  AAGTCCAGTT TGTACCTAAA AAAAAAA      SEQ ID NO:11
```

FIG. 16

Predicted Human APEG-1 Peptide Sequence

```
  1  MKPSPSQDRR SSDTGSKAPP TFKVSLMDQS VREGQDVIMS IRVQGEPKPV
 51  VSWLRNRQPV RPDQRRFAEE AEGGLCRLRI LAAERGDAGF YTCKAVNEYG
101  ARQCEARLEV RGE*  SEQ ID NO:12
```

FIG. 17

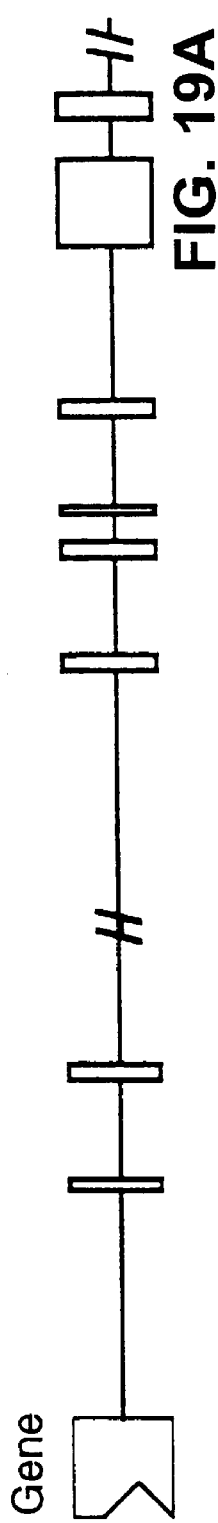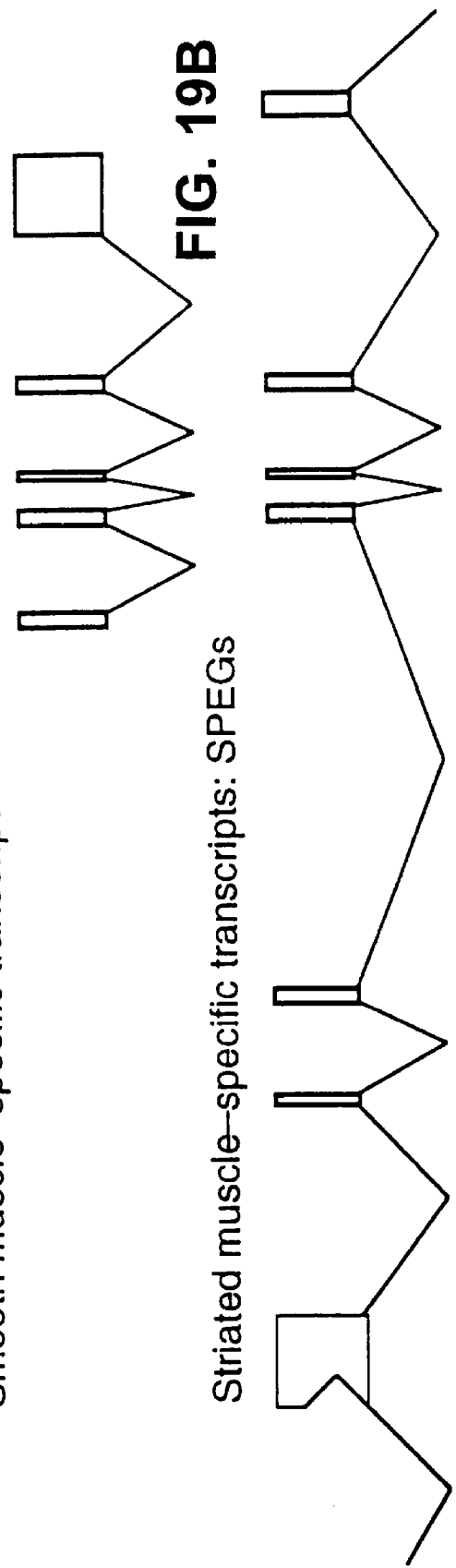
FIG. 19A
FIG. 19B
FIG. 19C
Gene
Smooth muscle-specific transcript: APEG-1
Striated muscle-specific transcripts: SPEGs
☐ Common exons
☐ Vascular smooth muscle-specific exons
☐ Striated muscle-specific exons

```
   1  GAATTCCGGT CCAAATCCGC GCTGCTCCCC CCACCGTCCC CTCGGGTCGG
  51  GAAGCGGTCC CCGCCGGGAC CCCCGGCCCA GCCCGCGGCC ACCCCACGT
 101  CGCCCCACCG TCGCACTCAG GAGCCTGTGC TGCCCGAGGA CACCACCACC
 151  GAAGAGAAGC GAGGGAAGAA GTCCAAGTCG TCCGGGCCCT CCCTGGCGGG
 201  CACCGGGAAT CCCGACCCCA GACGCCACTG AGCGAGGCCT CAGGCCGCCT
 251  GTGGGCGTTG GCCGATCGC CTAGGCTGGT GCGCGCCGGC TCCCGCATCC
 301  TGGACAAGCT GCAGTTCTTC GAGGAGCGAC GGCGCAGCCT GGAGCGCAGC
 351  GACTCGCCGC CGGCGCCCCT GCGGCCCTGG GTGCCCCTGC GCAAGGCCCG
 401  CTCTCTGGAG CAGCCCAAGT CGGAGCGCGG CGCACCGTGG GGCACCCCCG
 451  GGGCCTCGCA GGAAGAACTG CGGGCGCCAG GCAGCGTGGC CGAGCGGCGC
 501  CGCCTGTTCC AGCAGAAAGC GGCCTCGCTG GACGAGCGCA CGCGTCAGCG
 551  CAGCCCGGCC TCAGACCTCG AGCTGCGCTT CGCCCAGGAG CTGGGCCGCA
 601  TCCGCCGCTC CACGTCGCGG GAGGAGCTGG TGCGCTCGCA CGAGTCCCTG
 651  CGCGCCACGC TGCAGCGTGC CCATCCCCT CGAGAGCCCG GCGAGCCCCC
 701  GCTCTTCTCT CGGCCCTCCA CCCCAAGAC ATCGCGGGCC GTGAGCCCCG
 751  CCGCCGCCCA GCCGCCCTCT CCGAGCAGCG CGGAGAAGCC GGGGGACGAG
 801  CCTGGGAGGC CCAGGAGCCG CGGGCCGGCG GGCAGGACAG AGCCGGGGGA
 851  AGGCCCGCAG CAGGAGGTTA GGCGTCGGGA CCAATTCCCG CTGACCCGGA
 901  GCAGAGCCAT CCAGGAGTGC AGGAGCCCTG TGCCGCCCCC CGCCGCCGAT
 951  CCCCCAGAGG CCAGGACGAA AGCACCCCCC GGTCGGAAGC GGGAGCCCCC
1001  GGCGCAGGCC GTGCGCTTCC TGCCCTGGGC CACGCCGGGC CTGGAGGGCG
1051  CTGCTGTACC CCAGACCTTG GAGAAGAACA GGGCGGGGCC TGAGGCAGAG
1101  AAGAGGCTTC GCAGAGGGCC GGAGGAGGAC GGTCCCTGGG GGCCCTGGGA
1151  CCGCCGAGGG GCCCGCAGCC AGGGCAAAGG TCGCCGGGCC CGGCCCACCT
1201  CCCCTGAGCT CGAGTCTTCG GATGACTCCT ACGTGTCCGC TGGAGAAGAG
1251  CCCCTAGAGG CCCCTGTGTT TGAGATCCCC CTGCAGAATG TGGTGGTGGC
1301  ACCAGGGGCA GATGTGCTGC TCAAATGTAT CATCACTGCC AACCCCCGC
1351  CCCAAGTGTC CTGGCACAAG GATGGGTCAG CGCTGCGCAG CGAGGGCCGC
1401  CTCCTCCTCC GGGCTGAGGG TGAGCGGCAC ACCCTGCTGC TCAGGGAGGC
1451  CAGGGCAGCA GATGCCGGGA GCTATATGGC CACCGCCACC AACGAGCTGG
1501  GCCAGGCCAC CTGTGCCGCC TCACTGACCG TGAGACCCGG TGGGTCTACA
1551  TCCCCTTTCA GCAGCCCCAT CACCTCCGAC GAGGAATACC TGAGCCCCCC
1601  AGAGGAGTTC CCAGAGCCTG GGGAGACCTG GCCGCGAACC CCCACCATGA
1651  AGCCCAGTCC CAGCCAGAAC CGCCGTTCTT CTGACACTGG CTCCAAGGCA
1701  CCCCCCACCT TCAAGGTCTC ACTTATGGAC CAGTCAGTAA GAGAAGGCCA
1751  AGATGTCATC ATGAGCATCC GCGTGCAGGG GGAGCCCAAG CCTGTGGTCT
1801  CCTGGCTGAG AAACCGCCAG CCCGTGCGCC CAGACCAGCG GCGCTTTGCG
1851  GAGGAGGCTG AGGGTGGGCT GTGCCGGCTG CGGATCCTGG CTGCAGAGCG
1901  TGGCGATGCT GGTTTCTACA CTTGCAAAGC GGTCAATGAG TATGGTGCTC
1951  GGCAGTGCGA GGCCCGCTTG GAGGTCCGAG CGAGTGAGC TCAGGGGGCC
2001  ACCTGCGCTC CCCCGCTAC CTCCGAGCC GCGCCCTGT CTCAGGCACC
2051  TCTCGGACCT CGCTGTGTTT CACTGCCTCC TGCCCACAGA CCCAGCTGCC
2101  GGCCCGGACC CGTCCCAGCC TCCCCTCCCC ACCCCATGCA GCCCCCAGGG
2151  GGATAGCCCA TGGGCCCCTG TGGACCCTCC CTCCCCAAGT GGACACATGG
```

FIG. 20A

```
2201  CTGTGCAGCC AGGAGGCCCA CAGATGGACT GAGTGCTGGG AAGGGGCGGC
2251  TGCGAGGGGT ATCAACCCCC CGAGTCTCTC CCTGAAGGGG AGCACCGGGC
2301  GAGTGCATGT GCTACTGCTG CTACAGGCCT GTCTATCTGT TTGTCTGTCT
2351  GTGTGTCTGT GACAGTCAGG GAAGGATGCC TCGGAGCTGA GGTGGGGTGA
2401  GACAGAGTGG GAGAGATTAC GGCATGGCAT GGAGGGGCCC AAGGAGCAGG
2451  GGCTGTTGAC AAAGGCCTTA CCAGGAAGGG TTAGGACACT GACCATTCTA
2501  GAAATGGGTT TCGAATGGCA CAACACTTTC TATTTCACAA AAGACCAAAA
2551  GCCAGAGGCC CCAGGCTCTG TGCTGATGAA CAGCCTGGCT GAGCCCTGGC
2601  CCTGGCAGGT TTAGGGCCCA TTTGGGGCCC CCTCCTTCTC TGTCAGGGCT
2651  GGGGTGCTCT GTCTGGGAAT GAGGGAGTTA ACCAAGTTTG GTGCAGGAGC
2701  AGGGCAGGG GGCCACTGTA GTGAGCGTGG AGAAATTTGG AAACACCTAT
2751  TTCTTAACTC AAATAAAGTC CAGTTTGTAC CTAAAAAAAA AAA
      (SEQ ID NO:13)
```

FIG. 20B

```
  1 IPVQIRAAPP TVPSGREAVP AGTPGPARGH PHVAPPSHSG ACAARGHHHR REAREEVQVV
 61 RALPGGHRES RPQTPLSEAS GRLWALGRSP RLVRAGSRIL DKLQFFEERR RSLERSDSPP
121 APLRPWVPLR KARSLEQPKS ERGAPWGTPG ASQEELRAPG SVAERRRLFQ QKAASLDERT
181 RQRSPASDLE LRFAQELGRI RRSTSREELV RSHESLRATL QRAPSPREPG EPPLFSRPST
241 PKTSRAVSPA AAQPPSPSSA EKPGDEPGRP RSRGPAGRTE PGEGPQQEVR RRDQFPLTRS
301 RAIQECRSPV PPPAADPPEA RTKAPPGRKR EPPAQAVRFL PWATPGLEGA AVPQTLEKNR
361 AGPEAEKRLR RGPEEDGPWG PWDRRGARSQ GKGRRARPTS PELESSDDSY VSAGEEPLEA
421 PVFEIPLQNV VVAPGADVLL KCIITANPPP QVSWHKDGSA LRSEGRLLLR AEGERHTLLL
481 REARAADAGS YMATATNELG QATCAASLTV RPGGSTSPFS SPITSDEEYL SPPEEFPEPG
541 ETWPRTPTMK PSPSQNRRSS DTGSKAPPTF KVSLMDQSVR EGQDVIMSIR VQGEPKPVVS
601 WLRNRQPVRP DQRRFAEEAE GGLCRLRILA AERGDAGFYT CKAVNEYGAR QCEARLEVRG
661 E (SEQ ID NO:14)
```

FIG. 21

```
   1  GAATTCCGGC  TGGCGGGCAC  AGTGGAGTCC  CGGCCCCAGA  CGCCACTGAG
  51  CGAGGCTTCG  GGTCGCCTGT  CAGCACTGGG  CCGCTCGCCC  CGGCTGGTGC
 101  GCGCGGGGTC  CCGCATCCTG  GACAAGCTAC  AGTTCTTCGA  AGAGCGGCGA
 151  CGCAGCCTGG  AGCGCAGCGA  CTCGCCGCCA  GCGCCCCTGC  GGCCCTGGGT
 201  GCCCCTGCGC  AAGGCTCGCT  CGCTGGAGCA  GCCGAAGTCC  GAGGGCGGTG
 251  CGGCGTGGGG  CACACCCGAG  GCCTCGCAGG  AGGAGCTGCG  GTCACCTCGG
 301  GGCAGTGTGG  CAGAGCGGCG  TCGCCTGTTC  CAGCAAAAGG  CGGCCTCGTT
 351  GGATGAACGC  ACGCGACAAC  GCAGTGCAAC  CTCGGACCTC  GAACTCCGCT
 401  TCGCCCAGGA  GCTGGGTCGC  ATCCGCCGAT  CTACGTCGCG  GGAGGAGCTG
 451  GTGCGTTCGC  ACGAGTCCCT  GCGTGCCACG  CTGCAGCGCG  CCCCATCCCC
 501  TCGGGAGCCC  GGCGAGCCCC  CACTCTTCTC  CCGGCCTTCC  ACACCCAAGA
 551  CCTCACGGGC  TGTGAGCCCG  GCTGCCACCC  AGCCGCCGCC  TCCTAGTGGT
 601  GCGGGCAAAT  CTGGGGACGA  GCCTGGGAGG  CCCCGAAGCA  GAGGGCCGGT
 651  GGGCAGGACT  GAACCGGGGG  AAGGCCCGCA  GCAGGAGATC  AAGCGTCGGG
 701  ACCAATTCCC  GCTAACCAGG  AGCAGAGCCA  TCCAGGAGTG  CAGGAGCCCT
 751  GTGCCGCCCT  ACACCGCGGA  TCCCCCGGAG  AGCAGGACAA  AAGCCCCTC
 801  CGGTCGCAAG  CGGGAACCCC  CTGCTCAAGC  GGTGCGCTTT  CTGCCCTGGG
 851  CCACTCCGGG  AGTGGAGGAC  TCTGTTCTGC  CCCAAACCTT  GGAGAAGAAT
 901  AGAGCGGGAC  CCGAGGCTGA  GAAGAGGCTT  CGCAGAGGAC  CTGAGGAGGA
 951  TGGCCCCTGG  GGGCCCTGGG  ACCGCAGAGG  GACCCGCAGC  CAAGGCAAAG
1001  GTCGCCGTGC  TCGGCCTACT  TCCCCCGAGC  TCGAGTCCTC  AGACGACTCC
1051  TATGTGTCCG  CTGGGGAAGA  GCCCCTGGAG  GCACCCGTGT  TTGAGATCCC
1101  TCTGCAGAAT  ATGGTGGTGG  CGCCAGGAGC  TGACGTGCTA  CTTAAGTGTA
1151  TCATCACCGC  CAACCCCCCA  CCCCAAGTGT  CCTGGAAAAA  GGATGGGTCC
1201  ATGTTGCACA  GCGAGGGTCG  TCTTCTCATC  CGGGCTGAAG  GTGAACGGCA
1251  CACACTGCTG  CTCAGAGAGG  CCCAGGCTGC  TGATGCTGGG  AGCTACACAG
1301  CCACTGCCAC  CAACGAACTG  GGCCAAGCTA  CCTGTGCTTC  TTCACTGGCT
1351  GTGAGACCTG  GCGGCTCCAC  ATCCCCTTTC  AGCAGCCCCA  TCACCTCTGA
1401  TGAGGAGTAC  CTGAGCCCCC  CAGAGGAGTT  CCCAGAGCCT  GGGGAGACCT
1451  GGCCCCGAAC  CCCTACCATG  AAGCTCAGTC  CCAGCCAGGA  TCATGATTCC
1501  TCCGACTCTT  CTTCCAAGGC  ACCCCAACG   TTCAAGGTCT  CACTCATGGA
1551  CCAATCGGTG  AGAGAAGGTC  AAGATGTCAT  TATGAGCATC  CGTGTGCAGG
1601  GAGAGCCCAA  GCCTGTGGTT  TCCTGGCTGA  GGAATCGACA  GCCCGTGCGC
1651  CCAGACCAGC  GGCGCTTTGC  AGAGGAGGCC  GAGGGTGGGC  TCTGCCGCTT
1701  GAGGATCCTG  GCTGCTGAAC  GGGGCGATGC  TGGTTTCTAC  ACATGCAAGG
1751  CGGTCAACGA  ATATGGCGCT  CGGCAGTGCG  AGGCCCGCCT  GGAGGTCCGA
1801  GGCGAGTGAG  CTCAGGGGGC  CACCTGCGCT  GCCCCGCTA   CCCTCCGAGC
1851  TGCACCCCTG  TCTCAGGCAC  CTCTCGGACC  TCGCTGTGTT  TCACTGCCTC
1901  CTGCCCACAG  ACCCAGCCGG  CTCGCCGGCC  CGGACTTAGC  CCATGCTCCC
1951  CTTCCCTCCC  TAGCCCATAC  AGCACCCTGG  GGTAACCCAC  CGGGCCCCTG
2001  TGGATCCTCC  CTCCCCAAGT  GGATATGTGG  CTGTGCAGAC  CAGGAGGCCC
2051  CCAGAAGGAC  TGAGTGTTGG  GAAGGGATGG  CCATGAGGGG  TGCCAAGCTC
2101  CCTCGGTCTC  CCCATAGGGA  GCATCAGCG   AGTGCATGTG  CTATGCTGCT
2151  ACAGGCCACT  GTCTGTCTAT  CTGTTTGTCC  GTCTGTGTGT  CTGTGACAGT
2201  CAGGGAAGAA  AGCCTTTGAG  CTGAGGTGGG  CTAAGACAGA  ATAAGATGAC
2251  AGAGCACAGC  ATCCATGAGA  TGCAGGGGTT  CAGAGGGGTC  AGGTACAGTG
```

FIG. 22A

```
2301  GATATGAGGC TCTCTGGGAA GGGGCAGGGC ACTGACCATT TCAGAAATGG
2351  GTTTTAAATG GCACAACATT TTTTATTCCA CAAGAGACCA AAAGCTAGAG
2401  GTCTAGGGTT AAGCCCTAGC TGCTGGCAAG ATTAGGACCA AGTGGGGTAC
2451  CCTTCTTTAC AGACACATCC GACACGCGCT GTCTGAGAAT GAGAGAGGTA
2501  GCCAGGCTGA ACACAGGAGC AGGGTCATAG TGGAGGTGGA GATTTGGAAA
2551  CACTATTTCG TAGCTCAAAT AAAGTCCAGT TTGTACCCAA AAAAAAAAA
2601  AAAAAAAAAA AAAA (SEQ ID NO:15)
```

FIG.22B

```
  1 EFRLAGTVES RPQTPLSEAS GRLSALGRSP RLVRAGSRIL DKLQFFEERR RSLERSDSPP
 61 APLRPWVPLR KARSLEQPKS EGGAAWGTPE ASQEELRSPR GSVAERRRLF QQKAASLDER
121 TRQRSATSDL ELRFAQELGR IRRSTSREEL VRSHESLRAT LQRAPSPREP GEPPLFSRPS
181 TPKTSRAVSP AATQPPPPSG AGKSGDEPGR PRSRGPVGRT EPGEGPQQEI KRRDQFPLTR
241 SRAIQECRSP VPPYTADPPE SRTKAPSGRK REPPAQAVRF LPWATPGVED SVLPQTLEKN
301 RAGPEAEKRL RRGPEEDGPW GPWDRRGTRS QGKGRRARPT SPELESSDDS YVSAGEEPLE
361 APVFEIPLQN MVVAPGADVL LKCIITANPP PQVSWKKDGS MLHSEGRLLI RAEGERHTLL
421 LREAQAADAG SYTATATNEL GQATCASSLA VRPGGSTSPF SSPITSDEEY LSPPEEFPEP
481 GETWPRTPTM KLSPSQDHDS SDSSSKAPPT FKVSLMDQSV REGQDVIMSI RVQGEPKPVV
541 SWLRNRQPVR PDQRRFAEEA EGGLCRLRIL AAERGDAGFY TCKAVNEYGA RQCEARLEVR
601 GE (SEQ ID NO:16)
```

FIG. 23

```
   1 GCGATAGATAACCTGGTGATCCAAACCTGTAATCCTAACTACTGTGGAGGCTGAGATAAT
  61 AACTTGCCAGAGATACAGAGTCAGTTCAAGACCACCCTAGGCAACTAAAGAGATCTTGTT
 121 TCAGACTAAGAAAAGAGGCCTAGCAAGGCCCTACATTCAATCCCCCAGAAACAAATGAC
 181 TCAGACAGCCCAAGTCCAGACTGTAAATCAGAGACTACAGGGGACCATACCCCAAAGAAC
 241 TCTCTAGAATTCCTGTGCTCAGAAAACTTTGAAACCCAATCAACCAAACTGGGCAGTGGT
 301 GTCACATGCTTTTAATCCCAGTACTCAGGAGGCAGAGGCAGGCAGATCTCTGAGTTCAAG
 361 TCCAGCCTGATTTACTGATTGAGTCAAGGCTACACAGAGATACCCTGTCTCAAAAAACTA
 421 ACAAGCAAAATACAAAAACAAAAACCAAAAAAAAAAAAAAAAAAAAAAAAAAAATAAGAA
 481 GCCCAACCATATAAGAAGCATTTTGAAAAAAAACTAATGTTTGAAATCGCTGGCATGGGG
 541 TTAAAGATCTAGTTCAAATTGGGAAGCTGGCTGCTGTCATTGGAATCACAAGGGCTGTCG
 601 AACCAGACTTAGGGATTTACAGCCCTGCTCTGAAGTTGAATGGCCAAGAGCTGTGAGATT
 661 CAGTGAAATCACCTCTTAGAGTTCCATCCTCCCATGAGGATTTGCCTAGGTCTCAAAAC
 721 TTCCATGTGCCTAGGGATCTCTAGAGTGCTTTTGAAAAAAAATTACAGTGTTCGACTCCT
 781 CACTTTAGAAAATCAATTCTGTAGGCTGGATAAGGTCTAAGAATCTGTATTTCAAAACAA
 841 GCCCCAAGTGGTACCCGTGTGGGTGGTTCAAGCATCACGCACACAGTCCTGGTGTAGATG
 901 GCCTTGGGTGATGCTATCCGTGTGCTAGAAACTGGGTGTCTGTCGTGAAGAGACTACAGA
 961 CAGCTGGGATGTCAGGCTTGACTGGATATACTGGCCTGGGGGAAATTCCTGCTTGTGGGC
                                             NFkB/GArC
1021 TGTCTAATGCCAGTTCTTATTGAATGATACTGGCCTGAAAGAACTGTCCAAAGGGCAGCT
1081 AGATGAATAGAGTCAGCTCATGGAGAGCTGGGTCAAATGTAATGAAGTGGTCCTTTAATG
                                                         CArG
1141 GGAAGGTTTGGGATCAAAAGAACACTGCCCTTGCTGGTGTTATCTCCCACAGTGAAATCT
1201 GGGTTTGTAGATGGATCAGGCTTGGGATGTTACAAAAAAATGGCTACAAAGTTGCTTTAG
1261 CCCATGCGGTCTGCAGGGCTTGGGATTCTACAGCTTGGTGGTGTACTTTGGGGTTATGGC
1321 TGGAACAGAGGCCACTTCTTTTTCTCAGAGAGGCATTCCATTGGAGCTTGAGCCTGCAGC
1381 CTGACAAGCAATCTCGCCAAGACTCTTGACCTAGGCTTGCTGCTGATTGGCTGGCTAGCA
1441 CCTAGGTTCTATTTCCCTGCTGGCCACCAGGGGTCTCTGAAGCAAACATAGACCTTTGGC
1501 AATTCGAGTTAAATGTTTGCCCCGCCCTCCTTTCCTTAGCCTGGGAGCTTGCCTCAGCAC
                          Sp1
1561 TGTCCAGCCTGGAGGTGACCCTGGAGCCAGGAATCTAAACTCTGTAGAGGGAAAGGAGTC
1621 CCCTCTTCCAAGGGCTGTGCCTATGACCTCAGTATCAGCTGGTGGCCACGCCCCGGCCA
                                                Sp1
1681 CAAATGCCATTCGGATTTCTCTCTCCTCCCCAACCTTGAGACTGCCAGCCTGAAAGTGGG
1741 CTGTCCTCTTGGCCCCCACACTTCTTCATCACTGGCAGTGCTGGGGAACACAGGTCATAG
1801 CTTGGGAATGTGGCCCTGGGTGGAGAGAGGGGATCAAGGAGGGAGAGAGATTTGTGGCCT
1861 CTGCTCAACACCTCTGCTTCTATTATTCTTCCTGAGCCCCTTCCCTACCCACTGGGTGCA
1921 AACGGAAGCTGGGGAGGAGCGACCATTGGGGAGGAGCGGCCCACACTTCCCTAGCTTTGA
1981 GCCCTGGTGGGCTGAGGGGTGAGGGGCAGTTTGCCAGCAGAAATTCAGTAGAACCCATGG
2041 TTGAGCAGGGTGCAGGCCTGTGTCCTGAAGTACCTGCTCTCCTGAACTTGTCTAGGGCAG
2101 GACCTGGGAGTCTGCAGCCATGGGCTCAGTTTCCTTAGGTTGGCAGGGGACAAATCTGGA
2161 AAGGAGGGTCAAGCCCTGACAGTTCTTTGGTTCTCTGTGTCTGAAAAAGCTGGTTGTGGC
2221 CTATTTGGGGGTTTAAGGCTGGCTAGTTATGTATTCCTAGGTCAGGATTCTTCTTGGTTT
    CArG
2281 GGGCAAAGCATGGCGCTTGCTGTGCTGTATGGGTCAACACTTCTGGCCCAGGCAAGGATA
2341 TTAAATGCCGCAGTGCAGTGCCACCCCTTAGACCCCTCTGAGGACCGGGGTCCCCACACC
                                                        E box
2401 TGTAGTCTAGGCCCTACTGATGGGTTCAGCTCTTGTCAGTGTCCCAAGCTGTAAGGAGAG
2461 GAAAGGCAGACAGCTAGCTGCTTGGAATGATCAGAGTCTAAATTCAGCTGGTCTGGGCTC
                                                          Sp1
2521 CGCCCCTCCCCCGTTCCTATTCCACCACTCCAGGGGCTGCTCCCTGTGGTCTCAGCAGGC
2581 ACCACCTTCCCAGCCAGCGCCTGCCTGCTGCCCAGCCTCTTGCTGGCCACCCCACCTCC
2641 TCCTTCCCCCGCTCCTAGGCTCACTTCCCTCCCCCCAGGGCTGGCTCAGTGCGGGCCT
2701 CAGCTGGGTCAGCGAGTGAGTGGGGCTGGCCAGGCTGA  (SEQ ID NO:17)
```

FIG. 25

```
              1                                                                    50
Human.pep     MKPSPSQDRR  SSDTGSKAPP  TFKVSLMDQS  VREGQDVIMS  IRVQGEPKPV
Mouse.pep     MKLSPSQDHD  SSDSSSKAPP  TFKVSLMDQS  VREGQDVIMS  IRVQGEPKPV
Rat.pep       MKPSPSQDRD  SSDSSSKAPP  TFKVSLMDQS  VREGQDVIMS  IRVQGEPKPV
Consensus     MK xSPSQDxx  SSDxxxSKAPP  TFKVSLMDQS  VREGQDVIMS  IRVQGEPKPV 51                                                                   100
Human.pep     VSWLRNRQPV  RPDQRRFAEE  AEGGLCRLRI  LAAERGDAGF  YTCKAVNEYG
Mouse.pep     VSWLRNRQPV  RPDQRRFAEE  AEGGLCRLRI  LAAERGDAGF  YTCKAVNEYG
Rat.pep       VSWLRNRQPV  RPDQRRFAEE  AEGGLCRLRI  LAAERGDAGF  YTCKAVNEYG
Consensus     VSWLRNRQPV  RPDQRRFAEE  AEGGLCRLRI  LAAERGDAGF  YTCKAVNEYG 101         114
Human.pep     ARQCEARLEV  RGE*       (SEQ ID NO:12)
Mouse.pep     ARQCEARLEV  RGE*       (SEQ ID NO:18)
Rat.pep       ARQCEARLEV  RGE*       (SEQ ID NO:13)
Consensus     ARQCEARLEV  RGEx       (SEQ ID NO:19)
```

SINGLE GENE ENCODING AORTIC-SPECIFIC AND STRIATED-SPECIFIC MUSCLE CELL ISOFORMS AND USES THEREOF

This application is a continuation-in-part of U.S. Ser. No. 08/494,577, filed on Jun. 22, 1995.

BACKGROUND OF THE INVENTION

The invention relates to diagnosis and treatment of vascular injury.

Atherosclerosis and its subsequent complications, such as myocardial infarction, stroke, and peripheral vascular diseases, are the major causes of death in developed countries. Vascular endothelial and smooth muscle cells have important roles in the regulation of normal vascular tone. Damage or dysfunction of these cells can lead to vascular diseases, such as atherosclerosis and restenosis.

Atherosclerosis is believed to be a consequence of a response of the vascular wall to injury (Ross, R., 1993, Nature 362:801–9). Upon vascular injury and various other stimuli, cytokines and growth factors from activated vascular cells promote growth and migration of vascular smooth muscle cells in a dedifferentiated status, resulting in the formation of atherosclerotic plaques.

The pathogenesis of atherosclerosis is not fully understood, and an effective therapeutic regime has not been developed to prevent or cure atherosclerosis (Ross, R., The Pathogenesis of Atherosclerosis, in Heart Disease, a textbook of cardiovascular medicine, E. Braunwald, Editor, 1992, W. B. Saunders Company: Philadelphia. pp. 1106–24; and Ross, R.: The Pathogenesis of Atherosclerosis: a Perspective for the 1990s, 1993, Nature 362:801–9). Despite extensive research, the molecular mechanisms responsible for the regulation of gene expression in vascular endothelial and smooth muscle cells are largely unknown. In particular, trans-acting factors and cis-acting elements mediating vascular cell-specific gene expression have not been identified, mainly due to the fact that only a few vascular specific genes have been identified. Furthermore, of the genes that have been characterized as endothelial cell-specific (e.g. von Willebrand factors, VEGF receptor flk-1, VCAM-1, and E-selection (Hunter, J. J., et al., 1993, Hypertension 22:608–17) or smooth muscle cell-specific (e.g., CHIP28, SM22, and gax (Gorski, D. H., et al., 1993, Mol. Cell. Biol. 13(6):3722–33), many have been found in other cell types at various levels.

SUMMARY OF THE INVENTION

The invention is based on the discovery of a novel gene the expression of which gives rise to variant isoforms, one which is specific to aortic cells, and others which are found in striated muscle cells. Accordingly, the invention features an aortic cell-specific gene, and therefore provides a substantially pure DNA (e.g., genomic DNA, cDNA or synthetic DNA) encoding an aortic-preferentially-expressed gene-1 (APEG-1) polypeptide. By "substantially pure DNA" is meant DNA that is free of the genes which, in the naturally-occurring genome of the organism from which the DNA of the invention is derived, flank the APEG-1 gene. The term therefore includes, for example, a recombinant DNA which is incorporated into a vector, into an autonomously replicating plasmid or virus, or into the genomic DNA of a prokaryote or eukaryote at a site other than its natural site; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

Hybridization is carried out using standard techniques such as those described in Ausubel et al., Current Protocols in Molecular Biology, John Wiley & Sons, (1989). "High stringency" refers to DNA hybridization and wash conditions characterized by high temperature and low salt concentration, e.g., wash conditions of 65° C. at a salt concentration of approximately 0.1×SSC. "Low" to "moderate" stringency refers to DNA hybridization and wash conditions characterized by low temperature and high salt concentration, e.g. wash conditions of less than 60° C. at a salt concentration of at least 1.0×SSC. For example, high stringency conditions may include hybridization at about 42° C., and about 50% formamide; a first wash at about 65° C., about 2× SSC, and 1% SDS; followed by a second wash at about 65° C. and about 0.1%×SSC. Lower stringency conditions suitable for detecting DNA sequences having about 50% sequence identity to an APEG-1 gene are detected by, for example, hybridization at about 42° C. in the absence of formamide; a first wash at about 42° C., about 6× SSC, and about 1% SDS; and a second wash at about 50° C., about 6× SSC, and about 1% SDS.

A substantially pure DNA having at least 50% sequence identity (preferably at least 70%, more preferably at least 80%, and most preferably at least 90%) to SEQ ID NO:1, 2, or 11, and encoding a polypeptide having a biological activity of an APEG-1 polypeptide is also within the invention. The percent sequence identity of one DNA to another is determined by standard means, e.g., by the Sequence Analysis Software Package developed by the Genetics Computer Group (University of Wisconsin Biotechnology Center, Madison, Wis.) (or an equivalent program), employing the default parameters thereof. "Biological activity of an APEG-1 polypeptide" is defined as the ability to inhibit the proliferation or migration of smooth muscle cells at the site of vascular injury.

The invention also includes a substantially pure DNA containing a constitutive or inducible, vascular cell-specific promoter, e.g., an APEG-1 promoter which is preferably in a vector into which an heterologous gene may be or has been cloned, and under the control of which the gene may be expressed. The promoter is preferably specific for arterial cells (e.g., cells of the aorta), and most preferably specific for vascular smooth muscle cells. DNA encoding APEG-1 may be operably linked to such regulatory sequences for expression of the APEG-1 polypeptide in vascular cells.

By "promoter" is meant a minimal DNA sequence sufficient to direct transcription. Promoters may be constitutive or inducible, and may be coupled to other regulatory sequences or "elements" which render promoter-dependent gene expression cell-type specific, tissue-specific or inducible by external signals or agents; such elements may be located in the 5' or 3' region of the native gene, or within an intron.

By "operably linked" is meant that a coding sequence and a regulatory sequence(s) are connected in such a way as to permit gene expression when the appropriate molecules (e.g., transcriptional activator proteins) are bound to the regulatory sequence(s).

The invention also provides a method of directing vascular cell-specific expression of a protein by introducing into a vascular cell an isolated DNA containing a sequence encoding the protein operably linked to the vascular cell-specific promoter. A cell containing the DNA or vector of the invention is also within the invention.

The invention also features a substantially pure APEG-1 polypeptide (e.g., rat APEG-1 (SEQ ID NO:3) or human APEG-1 (e.g., human APEG-1 (SEQ ID NO:12)) and an antibody which specifically binds to an APEG-1 polypeptide. By a "substantially pure polypeptide" is meant a polypeptide which is separated from those components (proteins and other naturally-occurring organic molecules) which naturally accompany it. Typically, the polypeptide is substantially pure when it constitutes at least 60%, by weight, of the protein in the preparation. Preferably, the protein in the preparation is at least 75%, more preferably at least 90%, and most preferably at least 99%, by weight, APEG-1 polypeptide. A substantially pure APEG-1 polypeptide may be obtained, for example, by extraction from a natural source (e.g., an aortic cell); by expression of a recombinant nucleic acid encoding an APEG-1 polypeptide; or by chemically synthesizing the protein. Purity can be measured by any appropriate method, e.g., column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include recombinant polypeptides derived from a eukaryote but produced in E. coli or another prokaryote, or in a eukaryote other than that from which the polypeptide was originally derived.

In another aspect, the invention provides a method of detecting injury in a sample of vascular tissue by determining the level of APEG-1 gene expression in the tissue; a decrease in the level of expression detected in the tissue sample compared to that detected in uninjured control vascular tissue indicates the presence of a vascular injury.

The invention also includes a method of inhibiting smooth muscle cell proliferation in an animal by contacting an artery of the animal with an APEG-1 polypeptide or a biologically active fragment thereof or with a compound that stimulates the APEG-1 promoter, e.g., stimulates APEG-1 expression.

In yet another aspect, the invention includes a method of making an APEG-1 polypeptide, e.g., a rat or human APEG-1 polypeptide, involving providing a cell containing DNA encoding an APEG-1 polypeptide and culturing the cell under conditions permitting expression of the APEG-1-encoding DNA, i.e., production of the recombinant APEG-1 by the cell.

The invention further features a substantially pure DNA having an APEG-1 derived promoter/enhancer sequence which regulates vascular smooth muscle cell-specific transcription of a polypeptide-encoding sequence to which it is operably linked. By "promoter/enhancer sequence" is meant a DNA sequence located 5' to the transcriptional start site of the APEG-1 gene and which contains one or more cis-acting elements which regulate transcription, e.g., cell specific transcription. The elements may be contiguous or separated by DNA not involved in the regulation of transcription, e.g., an enhancer element may be in a position immediately adjacent to the promoter element or up to several kilobases upstream or downstream of the transcriptional start site. The promoter/enhancer DNA is preferably derived from the 5' region of a mammalian APEG-1 gene, such as that of the mouse (SEQ ID NO:17), and regulates preferential expression in vascular smooth muscle cells, e.g., aortic smooth muscle cells, of a polypeptide-encoding DNA to which it is operably linked. Preferably, expression of a polypeptide under the control of the APEG promoter/enhancer (e.g., SEQ ID No:17) is at least 50% greater (e.g., as measured in the amount of polypeptide-encoding mRNA transcript), preferably at least 100% greater, more preferably at least 200% greater, and still more preferably at least 400% greater in vascular smooth muscle cells than in non-vascular smooth muscle cells. Most preferably, the APEG-1 promoter/enhancer directs vascular smooth muscle cell-specific polypeptide expression and directs negligible polypeptide expression in non-smooth muscle cell types. The promoter/enhancer sequence may in addition regulate developmental stage-specific expression, e.g., preferential expression in embryonic cells, of a polypeptide-encoding sequence.

The DNA of the invention (promoter/enhancer sequence) may be operably linked to a DNA sequence encoding a polypeptide that is not APEG-1 (i.e., a heterologous polypeptide), and function to regulate vascular smooth muscle cell-specific transcription of the polypeptide-encoding sequence. Examples of such polypeptides include tissue plasminogen activator (tPA), p21 cell cycle inhibitor, nitric oxide synthase, interferon-γ, and atrial natriuretic polypeptide.

The invention also includes a vector containing the promoter/enhancer DNA of the invention (operably linked to a polypeptide-encoding DNA sequence) and a vascular smooth muscle cell containing the vector. Also within the invention is a method of directing vascular smooth cell-specific expression of the polypeptide by introducing the vector into a vascular smooth muscle cell and maintaining the cell under conditions which permit expression of the polypeptide, e.g., introducing the vector into a human patient for gene therapy.

The vector of the invention can be used for gene therapy. For example, the vector can be introduced into a vascular smooth muscle cell to direct vascular smooth muscle cell-specific expression of a polypeptide. The vector of the invention can also be used for directing developmental stage-specific expression, e.g., preferential expression by embryonic cells, of a polypeptide, involving introducing into a vascular smooth muscle cell the vector of the invention.

The invention also features a method of inhibiting proliferation of vascular smooth muscle cells by administering to the cells an APEG-1 polypeptide.

The invention also features a striated muscle cell-specific variant gene product arising from the same genomic DNA encoding APEG-1, and therefore provides a substantially pure DNA (e.g., genomic DNA, cDNA or synthetic DNA) encoding a striated muscle preferentially-expressed gene (SPEG) polypeptide.

The DNA may encode a naturally occurring mammalian SPEG polypeptide such as a human SPEG polypeptide (SEQ ID NO:14) or mouse SPEG polypeptide (SEQ ID NO:16). For example, the invention includes degenerate variants of the human cDNA (SEQ ID NO:13) or the mouse cDNA (SEQ ID NO:15). The invention also includes a substantially pure DNA comprising a strand which hybridizes at high stringency to a DNA having the sequence of SEQ ID NO:13 or 15, or the complements thereof.

A substantially pure DNA having at least 50% sequence identity (preferably at least 70%, more preferably at least 80%, and most preferably at least 90%) to SEQ ID NO:13, or 15, and encoding a polypeptide having a biological activity of a SPEG polypeptide is also within the invention.

The invention also includes a substantially pure DNA containing a constitutive or inducible striated muscle cell-specific promoter, e.g., a SPEG promoter which is preferably in a vector into which an heterologous gene may be or has been cloned, and under the control of which promoter the gene may be expressed. The promoter is preferably specific for striated muscle cells (e.g., cells of skeletal or cardiac muscle). DNA encoding SPEG may be operably linked to such regulatory sequences for expression of the SPEG polypeptide in striated muscle cells.

The invention also provides a method of directing striated muscle cell-specific expression of a protein by introducing into a cell an isolated DNA containing a sequence encoding the protein operably linked to the striated cell-specific promoter. A cell containing the DNA or vector of the invention is also within the invention.

The invention also features a substantially pure SPEG polypeptide (e.g., human (SEQ ID NO:14) or mouse SPEG (SEQ ID NO:16) and an antibody which specifically binds to a SPEG polypeptide.

Other features and advantages of the invention will be apparent from the following description of the preferred embodiments thereof, and from the claims.

DETAILED DESCRIPTION

The drawings will first be described.

FIG. 1. is a flow chart of the differential mRNA display procedure for identifying APEG sequences.

FIG. 2A is a photograph of a differential mRNA display showing APEG-1 preferentially expressed in the rat aorta. The differential expression was tested among 6 rat tissues. Unique bands in the aorta that were eluted and reamplified for subsequent analysis are indicated (●).

FIG. 2B is a photograph of a differential mRNA display showing APEG-2 preferentially expressed in the rat aorta. The differential expression was tested among 6 rat tissues. Unique bands in the aorta that were eluted and reamplified for subsequent analysis are indicated (●).

FIG. 2C is a photograph of a differential mRNA display showing APEG-3 preferentially expressed in the rat aorta. The differential expression was tested among 6 rat tissues. Unique bands in the aorta that were eluted and reamplified for subsequent analysis are indicated (●).

FIG. 2D is photograph of a differential mRNA display showing APEG-4 preferentially expressed in the rat aorta. The differential expression was tested among 6 rat tissues. Unique bands in the aorta that were eluted and reamplified for subsequent analysis are indicated (●).

FIG. 2E is a photograph of a Northern blot analysis showing tissue expression of APEG-1. Ten micrograms of total RNA from each tissue were used in Northern analysis. The loading of each tissue RNA was normalized by comparing 18s rRNA hybridization signals (shown in FIG. 2F).

FIG. 2F is a photograph of a Northern blot analysis showing 18s rRNA.

FIG. 2G is a photograph of a Northern blot analysis showing tissue expression of APEG-2. Ten micrograms of total RNAs from each tissue were used in Northern analysis, and the loading of each tissue RNA was normalized by comparing 18s rRNA hybridization signals.

FIG. 2H is a photograph of a Northern blot analysis showing tissue expression of APEG-3. Ten micrograms of total RNAs from each tissue were used in Northern analysis, and the loading of each tissue RNA was normalized by comparing 18s rRNA hybridization signals.

FIG. 2I is a photograph of a Northern blot analysis showing tissue expression of APEG-4. Ten micrograms of total RNAs from each tissue were used in Northern analysis, and the loading of each tissue RNA was normalized by comparing 18s rRNA hybridization signals.

FIG. 3A is a photograph of a Northern blot analysis using full length cDNA of APEG-1 (APEG-1 full cDNA) as a probe. Samples of RNA from twelve rat organs were analyzed. The respective lanes are labelled in FIG. 3D.

FIG. 3B is a photograph of a Northern blot analysis using a 3' cDNA fragment originally cloned by differential mRNA display (APEG-1 3' D.D. frag.) as a probe. Samples of RNA from twelve rat organs were analyzed.

FIG. 3C is a photograph of a Northern blot showing 18s rRNA bands (18s rRNA) to which RNA loading was normalized.

FIG. 3D is a bar graph showing tissue distribution of APEG-1 gene expression.

FIG. 4 is a flow chart showing the cloning strategy for APEG-1. A rat aortic cDNA library established in the yeast expression vector pcJATA was screened to isolate full length APEG-1 cDNA. Southern analysis was carried out to confirm the presence of APEG-1 in this cDNA library. Restriction enzyme-digested (EcoRI and XhoI) cDNA fragments were separated on an agarose gel and the portions that contained APEG-1 cDNA, as determined by size markers and Southern analysis, were excised to elute the cDNA contents. Eluted cDNAs were ligated with linearized pSP72 vectors, and the ligated DNAs were used to transform competent E. coli DHα5 cells to establish a size-selected aortic cDNA sublibrary. This cDNA sublibrary was screened by the APEG-1 cDNA 3' fragment to obtain its full length cDNA.

FIG. 5 is a diagram of the nucleotide sequence of rat APEG-1 cDNA (SEQ ID NO:1). The longest open reading frame is located from nucleotide 169 to 511 (BOLD UPPERCASE) and the ATG flanking nucleotides that match the Kozak consensus sequence are indicated (UPPERCASE). A very short upstream open reading frame is present from nucleotide 102 to 116 (italic). There is a polyadenylation signal (underline) 21 nucleotides upstream of the poly-A tail. The primer annealing site of the 5' arbitrary primer used in the initial differential display PCR is also indicated (ITALIC UPPERCASE).

FIG. 6 is a diagram of the amino acid sequence (SEQ ID NO:3) deduced from the longest APEG-1 cDNA open reading frame (SEQ ID NO:2). Possible phosphorylation sites of protein kinase C and casein kinase-2 are indicated (bold). An integrin binding site, RGD, is also shown (bold italic). "****" represents a stop codon.

Figures 7A, 7B:
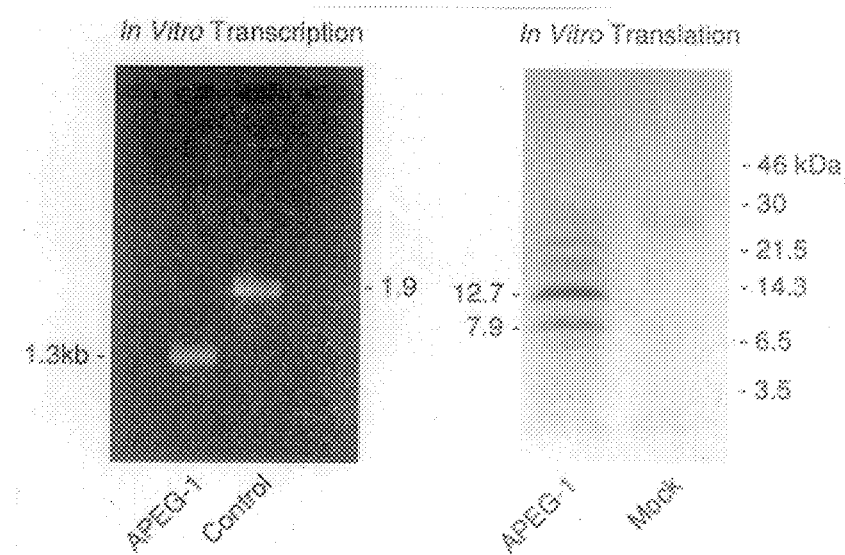

FIG. 7A is a photograph of in vitro transcription products of the APEG-1 gene. The 1.3 kb APEG-1 cDNA and a positive control DNA template were transcribed by T7 RNA polymerase. 1 µl of the 20 µl RNA products were resolved on a 1.2% denaturing agarose gel.

FIG. 7B is a photograph of in vitro translation products of the APEG-1 gene. In vitro transcribed APEG-1 mRNA was translated by wheat germ extract in the presence of [$^{35}$S]-methionine, and separated on a 10% tricine-SDS-polyacrylamide gel. In the mock reaction, mRNA template was absent.

FIG. 8 is an alignment of amino acid sequences of APEG-1 (SEQ ID NO:8), the myosin light chain kinase of chicken (ChkMLCK; SEQ ID NO:5) and of rabbit (RabMLCK; SEQ ID NO:7), and telokin of chicken (ChkTelo; SEQ ID NO:4) and of rabbit (RabTelo; SEQ ID NO:6). A consensus sequence (SEQ ID NO:9) is also shown to indicate the amino acid residues that are identical among these proteins. The conserved serine residue that is phosphorylated by cAMP-dependent protein kinase is marked by an asterisk (*).

FIG. 9A is a diagram of APEG-1 cDNA. APEG-1 cDNA was divided into four fragments by EcoR I, BamHI, Hind III, and XhoI restriction enzyme digestion. The three large fragments (405, 299, and 432 bp) were used to probe six rat tissue RNAs to show their different hybridization patterns.

FIG. 9B is a photograph of a Northern analysis using the 405 bp fragment of APEG-1 cDNA as a probe.

FIG. 9C is a photograph of a Northern analysis using the 299 bp fragment of APEG-1 cDNA as a probe.

FIG. 9D is a photograph of a Northern analysis using the 432 bp fragment of APEG-1 cDNA as a probe.

FIG. 10 is a photograph of a genomic Southern analysis of the APEG-1 gene. Genomic DNA from cultured rat aortic smooth muscle cells was harvested and digested with EcoRI, HindIII, or BamHI. APEG-1 full length cDNA was used as probe in the Southern analysis. The size of each band (indicated on the right) was determined according to the size markers (indicated on the left).

Figures 11A, 11B:
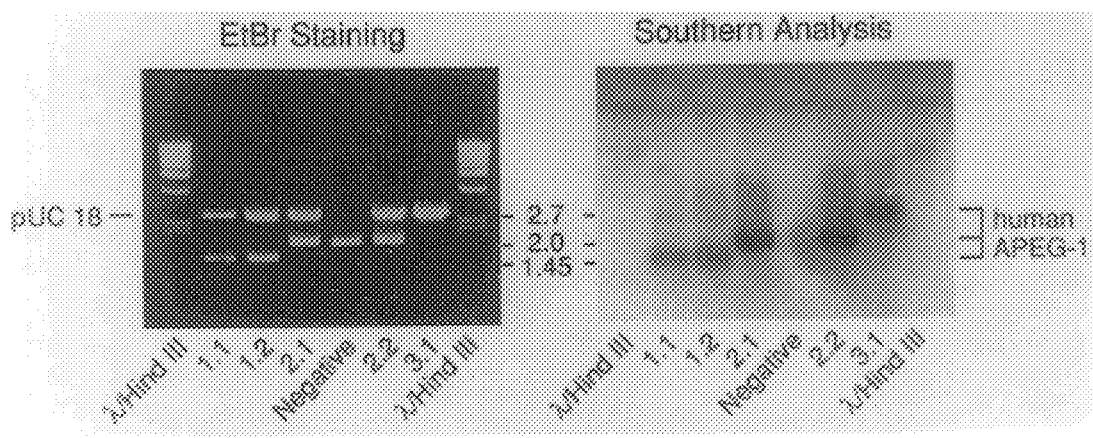

FIG. 11A is a photograph of ethidium bromide staining of the 3 clones of human homologues of rat APEG-1. Clone 1 (1.1, 1.2), clone 2 (2.1, 2.2), and clone 3 (3.1) were 1.45, 2.0, and 2.7 kb in size, respectively.

FIG. 11B is a photograph of a Southern analysis showing hybridization of these human homologues with a rat APEG-1 cDNA probe.

Figure 12:
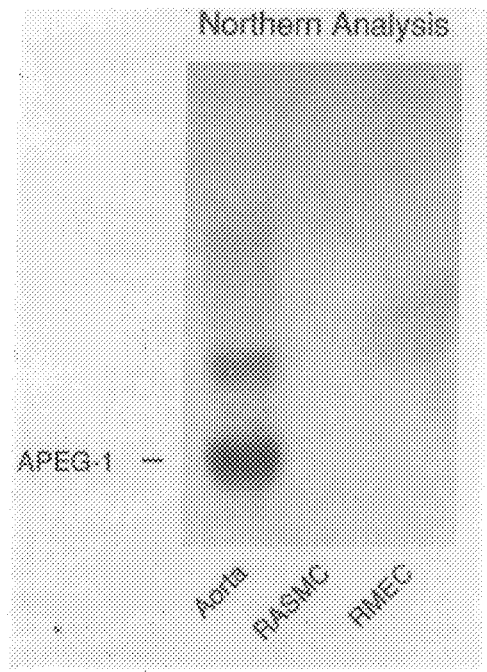

FIG. 12 is a photograph of a Northern analysis of APEG-1 expression in vitro. RNAs from rat aortic smooth muscle cells (RASMC) and from microvascular endothelial cells (RMEC) were purified and separated on a 1.2% denaturing agarose gel. RNA from normal rat aorta was used as a positive control. APEG-1 cDNA was used as probe in Northern analysis to examine its expression in these two cell types.

FIG. 13A is a photograph of a Northern analysis showing expression of APEG-1 in rat carotid artery during balloon injury. RNAs were purified from rat carotid arteries 2, 5, 8 days after balloon injury. Three injured rats were used in each time point and two uninjured rats were used as control. The APEG-1 cDNA was used in Northern analysis and the band intensities were normalized by 18s rRNA signal.

FIG. 13B is a bar graph showing expression of APEG-1 in rat carotid artery during balloon injury. Each column represents the mean expression of APEG-1 in the Northern analysis bands shown in FIG. 13A, expressed as a percent of control±one standard error.

FIG. 14A is a photograph of a Coomassie blue stained 10% tricine-SDS-PAGE gel showing the purified FLAG-APEG-1 fusion protein. M, protein size marker. Ext, induced bacterial cell extracts. FT, cell extract that flowed through the FLAG peptide affinity column.

FIG. 14B is a photograph of a Western analysis of the purified fusion protein. A monoclonal anti-FLAG peptide antibody, M2 (IBI), was used to identify the purity of the fusion protein. Un, uninduced bacterial cell extracts. In, induced bacterial cell extracts. FT, cell extract that flowed through the FLAG peptide affinity column.

Figure 15:
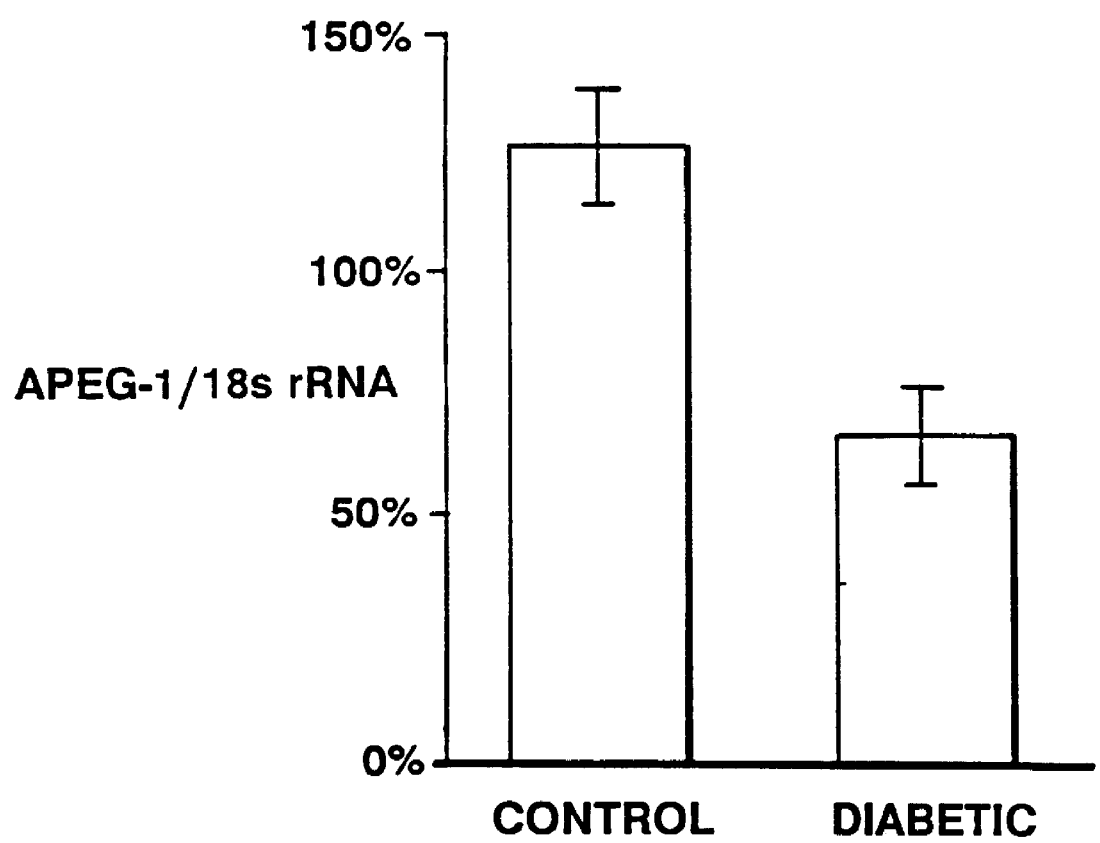

FIG. 15 is a bar graph comparing APEG-1 expression in diabetic rats and control rats. APEG-1 expression was decreased in diabetic rats (unpaired T test: $T_{10}$=3.284, p value=0.0033).

FIG. 16 is a diagram showing the cDNA sequence of human APEG-1 (SEQ ID NO:11).

FIG. 17 is a diagram showing the amino acid sequence of human APEG-1 (SEQ ID NO:12). "*" represents a stop codon.

Figures 18A, 18B:
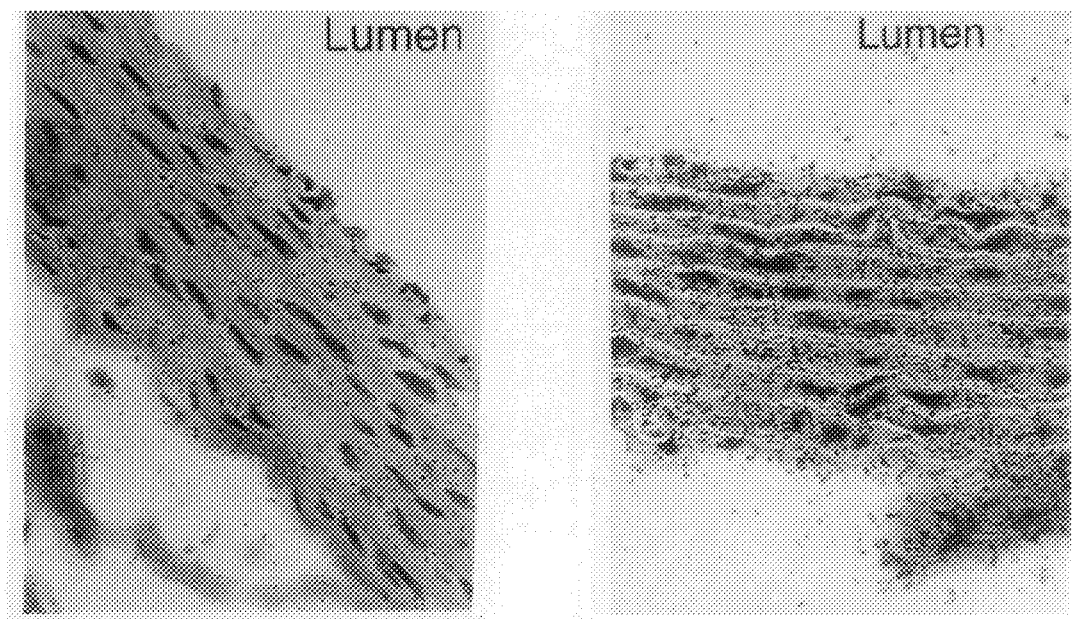

FIG. 18A is a photograph showing the results of an in situ hybridization experiment. The lumen of a rat aorta was sectioned and hybridization carried out using a rat APEG-1 sense strand DNA probe as a control.

FIG. 18B is a photograph showing APEG-1 mRNA expression in the lumen of a rat aorta. In situ hybridization was carried out using a rat antisense strand DNA probe to measure rat APEG-1 expression in aortic tissue.

FIGS. 19A–C are diagrams showing the pattern of exon usage in the APEG-1 and SPEG transcripts. FIG. 19A is a diagram showing the intron/exon arrangement of the APEG/SPEG locus. FIG. 19B is a diagram showing APEG-1 exon usage. FIG. 19C is a diagram showing SPEG exon usage.

FIG. 20 is a diagram showing the cDNA sequence of human SPEG (SEQ ID NO:13).

FIG. 21 is a diagram showing the amino acid sequence of human SPEG (SEQ ID NO:14).

FIG. 22 is a diagram showing the cDNA sequence of mouse SPEG (SEQ ID NO:15).

FIG. 23 is a diagram showing the amino acid sequence of mouse SPEG (SEQ ID NO:16).

Figure 24A:
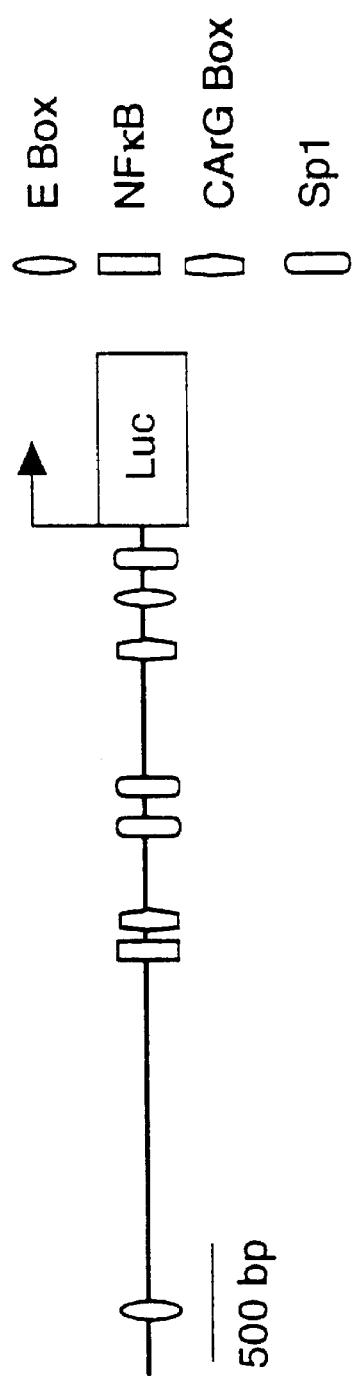

FIG. 24A is a diagram showing the PGL-3 construct.

Figure 24B:
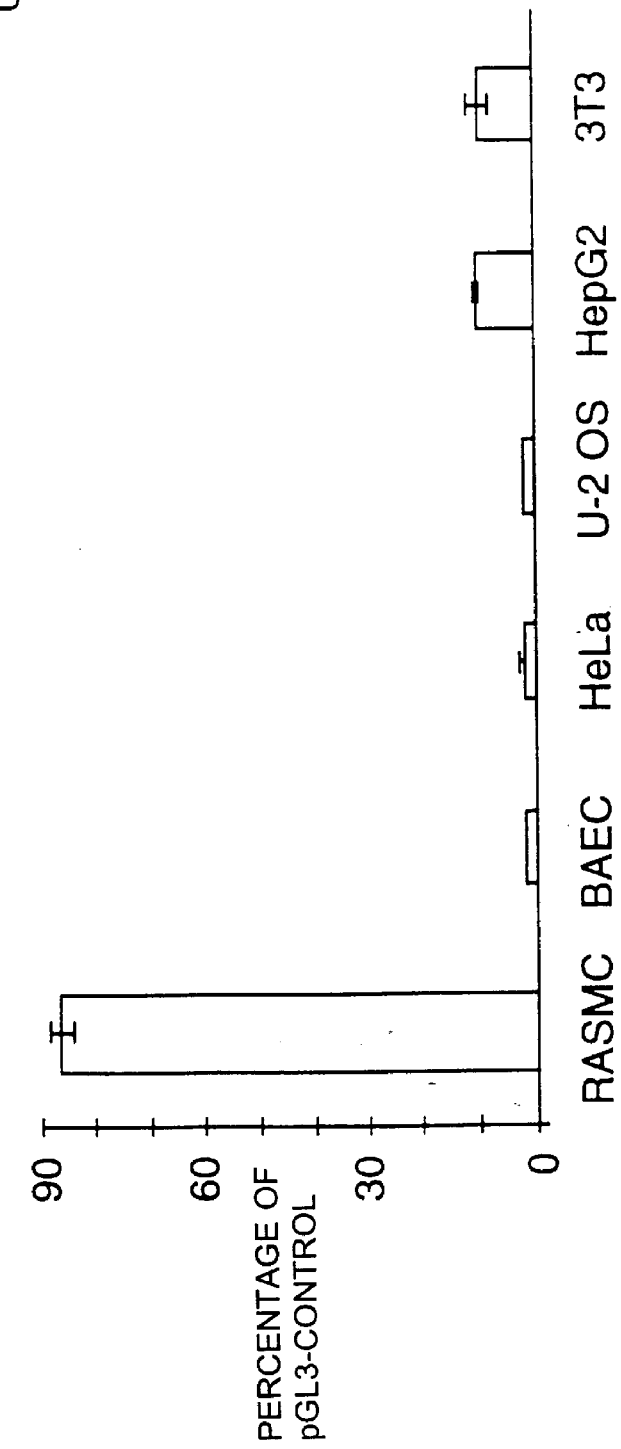

FIG. 24B is a bar graph showing the results of reporter transfection assays using 3.3 kb of APEG-1 5' sequence. Cell lines used: RASMC, rat aortic smooth muscle cells; BAEC, bovine aortic endothelial cells; HeLa, human epidermoid carcinoma cell line; U-2 OS, human osteosarcoma cells; HepG2, human hepatoma cells; NIH 3T3 mouse fibroblasts.

FIG. 25 is a diagram showing the sequence of a 2.7 kb fragment containing the APEG-1 5' vascular smooth muscle cell-specific promoter activity (SEQ ID NO:17).

FIG. 26 is a diagram showing a comparison of the full-length APEG-1 amino acid sequences of the human, mouse and rat.

Figure 27:
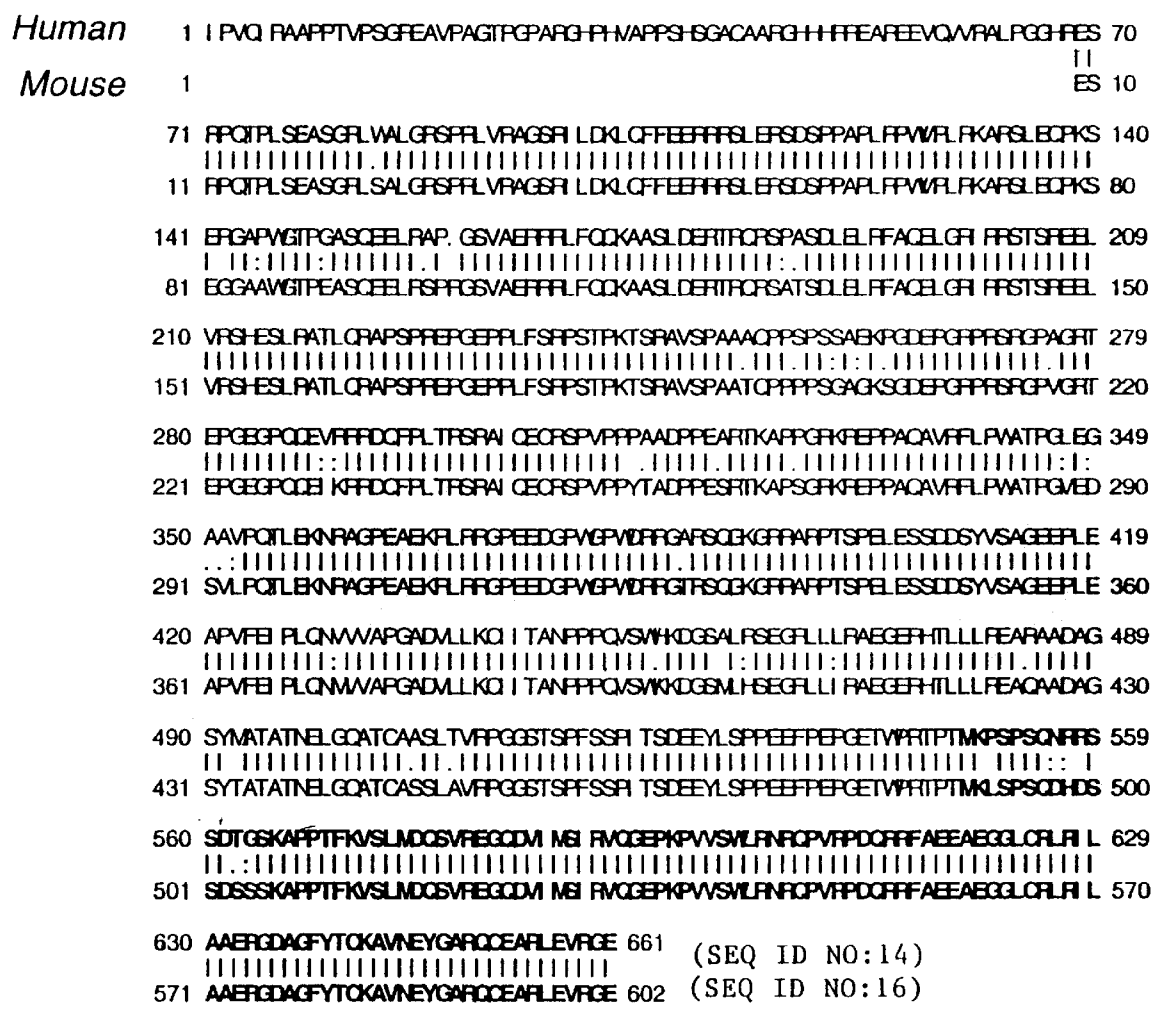

FIG. 27 is a diagram showing a comparison of partial SPEG amino acid sequences in human and mouse. "*" represents a stop codon.

PURIFICATION OF TOTAL RNAS

Total RNA was harvested from male Sprague-Dawley rat organs. The dissected organs were washed in phosphate buffered saline and snap-frozen in liquid nitrogen. The adventitia of the aorta was stripped, and the contents of the small intestine were removed before freezing. The frozen organs were homogenized and RNAs were harvested by acid guanidinium thiocyanate-phenol-chloroform extraction (Chomczynski, P. et al., 1987, Anal. Biochem. 162(1):156–9). Mouse embryo RNA was harvested from whole embryos. The cell culture RNAs were purified by guanidinium/CsCl ultracentrifugation.

Differential mRNA Display

Fifty micrograms of total RNA were treated with DNase I (Boehringer Mannheim) to remove contaminating genomic DNA in the presence of RNase inhibitor RNasin (Promega). After phenol/chloroform extraction and ethanol precipitation, the RNA concentration was adjusted to 0.1 μg/ml in DEPC-treated dH$_2$O. First strand cDNA was synthesized using MMLV reverse transcriptase (GIBCO, BRL) with the 3' poly-A-anchoring primer $T_{12}VG$ (5'-

TTTTTTTTTTTTVG-3') (SEQ ID NO:10). Subsequently the reaction was heated at 95° C. to inactivate reverse transcriptase, and the cDNA products were stored at −20° C. Two microliters of the cDNA were used in 20 μl PCR reactions (2 μl cDNA, 0.2 μM 5' arbitrary primer, 1 μM 3' $T_{12}VG$ primer, 1.5 mM $Mg^{2+}$, 2.5 μM dNTP, 12.5 μCi $^{35}$S-dATP, 1 unit Taq DNA polymerase; 94° C. for 15 sec, the thermal cycling was 40° C. for 30 sec and 72° C. for 30 sec; the thermal cycling was repeated for 40 cycles) following the reverse transcription. Sample loading buffer (98% formamide, 0.05% bromophenol blue, and 0.05% xylene cyanol) was added, and the samples were heated at 95° C. before loading onto a 6% sequencing gel. Overnight exposure of the dried sequencing gels to X-OMAT films (Kodak) was usually sufficient to display the differential mRNA patterns.

Reamplification of eluted cDNAs

Bands of interest on the dried gel were excised, soaked in 200 μl dH$_2$O for 10 minutes at room temperature, and eluted by heating at 95° C. for 15 minutes. After a brief centrifugation, the supernatants were transferred into fresh tubes, and the eluted DNAs were ethanol-precipitated at −20° C. in the presence of 20 μg glycogen and 300 mM sodium acetate. The precipitated DNAs were collected by centrifugation and washed with 70% ethanol. Dried DNA pellets were resuspended in 10 μl dH$_2$O and nonradioactively reamplified by PCR with the same initial PCR primers and condition, except that the reaction volume was scaled up to 100 μl with 25 μM dNTP. Reamplified cDNAs were resolved on 1% agarose gel to determine their sizes and amounts.

RNA gel electrophoresis and Northern blotting

Ten micrograms of total RNA were heat-denatured and loaded on a denaturing agarose gel (1.2% agarose, 1.1% formaldehyde, 0.5 μg/ml ethidium bromide in MOPS buffer). Electrophoresis was carried out at 10 V/cm for three to four hours. A photograph of the ethidium bromide staining pattern of the RNAs was taken under UV light illumination. The RNAs were then transferred onto a Nitropure membrane (Micron Separation Inc.) by standard blotting procedure (Ausubel, F. M., et al., ed. Current Protocols in Molecular Biology. ed. K. Janssen., 1994, Vol. 1., Current Protocols:4.9.1-14).

DNA gel electrophoresis and Southern blotting

DNAs were loaded and separated on a 1% agarose gel, followed by standard Southern blotting (Ausubel, F. M., et al., ed. Current Protocols in Molecular Biology. ed. K. Janssen., 1994, Vol. 1, Current Protocols: 2.9.1-15). The DNAs in the gel were denatured in denaturation buffer (1.5M NaCl, 0.5N NaOH), then neutralized in neutralization buffer (1.5M NaCl, 1M TrisCl, pH 7.4) prior to being transferred onto a Nitropure membrane in 20×SSC solution overnight.

Random priming and hybridization

Radioactive DNA probes were generated by random priming (Boehringer Mannheim) with 25 to 50 ng of the DNA fragment. Hybridization to the DNA or RNA blots was carried out in QuikHyb solution (Stratagene) with 1×10$^6$ cpm/ml of radioactive probes and 0.2 mg/ml herring sperm DNA (Boehringer Mannheim) at 68° C. for one to two hours. The blots were washed and exposed to X-ray films for permanent records.

Quantitation of hybridization signals

To quantitate the hybridization signals, DNA and RNA blots were exposed to phosphor screens (Molecular Dynamics) overnight. The phosphor screens were then scanned by a PhosphoImager scanner (Molecular Dynamics) operated by the ImageQuant program (Molecular Dynamics) running on a PC-DOS/MS Windows computer system (Compaq). Intensities of the signals were quantified by the same ImageQuant program following the manufacturer's instructions.

DNA sequencing and sequence analysis

Dideoxynucleotide chain termination DNA sequencing method was used to sequence DNAs. One microliter of DMSO was always included to reduce the DNA template secondary structures that may interfere with the Sequenase (USB) enzymatic activity. The sequences were resolved on 8% sequencing gel (National Diagnostics). The DNA sequences were stored into a local computer mainframe (mbcrr.harvard.edu), and analyzed by a sequence analysis software package (Genetics Computer Group).

Fusion protein expression and purification

Rat APEG-1 cDNA was cloned into pFLAG-2 vector, then transformed into E. coli BL21 cells. Transformed BL21 cells were grown in large scale to an optical density (OD$_{595}$) of 1.75. The cell pellet was resuspended in extraction buffer (20 mM TrisCl, pH 7.4, 0.2 mM EDTA, 1M NaCl, 1 mM PMSF, 1 mM DTT) and sonicated on ice, after which the extract was frozen and thawed three times in liquid nitrogen and a 42° C. water bath. The soluble cell extract was collected by centrifugation (12,000×g, 4° C., 20 minutes) and used in purification of the fusion protein by affinity chromatography with a M2 anti-FLAG peptide mAb affinity column. The column, loaded twice with the soluble cell extract, was washed sequentially with 50 ml of each of the following solutions, TE/NaCl/NP-40 buffer (20 mM TrisCl pH 7.4, 0.2 mM EDTA, 150 mM NaCl, 0.5% NP-40), TE/NaCl buffer (20 mM TrisCl pH 7.4, 0.2 mM EDTA, 150 mM NaCl), and TE buffer (20 mM TrisCl pH 7.4, 0.2 mM EDTA). The FLAG-APEG-1 fusion protein was eluted with 10 ml glycine buffer (0.1M glycine, pH 3.0) and the eluates were slowly collected in 0.8 ml fractions into microfuge tubes containing 50 μl 1M TrisCl, pH 8.0, and 150 μl 5M NaCl solutions. The purity of the purified fusion proteins was assayed by protein electrophoresis and Coomassie blue staining as well as western blotting with anti-FLAG mAb.

Protein gel electrophoresis and western blotting

A 10% tricine-SDS-polyacrylamide gel system was used to separate bacterial-expressed pFLAG-APEG-1 fusion protein (Schägger, H. et al., 1987, Anal. Biochem. 166:368–79). This system was used because a 10% tricine-SDS-polyacrylamide gel has superior resolution for proteins less than approximately 14 kDa compared to a standard glycine-SDS-polyacrylamide gel. After electrophoresis, the protein gel was assembled in a semi-dry transfer apparatus (Hoefer) and the protein samples were transferred onto a PVDF membrane (Millipore) in transferring buffer (25 mM Tris base, 200 mM glycine, 20% methanol) at 125 mA for one hour.

In vitro transcription and translation

Rat APEG-1 cDNA was cloned into the pSP72 vector and linearized so that RNA could be transcribed from its upstream T7 promoter with the T7 RNA polymerase. Transcription was carried out in a large-scale T7 transcription system (Novagen) in the presence of 7-$^{me}$GpppGTP to produce capped mRNA. The in vitro transcribed mRNA was translated in an in vitro translation system of wheat germ extract (Promega) with the [$^{35}$S]-methionine to produce radiolabeled proteins.

Cellular localization

The expression plasmid c-myc-rAPEG-1/pCR3 was constructed by adding in frame a DNA sequence encoding a c-Myc peptide tag (EQKLISEED) to the rat APEG-1 open reading frame at the 5' end by PCR techniques known in the art (any other detectable peptide can be used as a tag to localize APEG-1). This hybrid DNA fragment was then cloned in to the eukaryotic expression vector pCR3 (Invitrogen, San Diego, Calif.). COS-7 cells were transiently transfected with the c-myc-rAPEG-1 expressing plasmid by a standard DEAE-dextran method (e.g., the method described in Tan et al., 1994, Kidney Intern. 46:690). The U-2 OS cells were transiently transfected by the calcium phosphate method known in the art. Twenty-four hours after transfection, cells were transferred to two-well chamber slides. The cells were fixed with 4% paraformaldehyde in PBS after growing for an additional twenty-four hours. Immunostaining was performed with an anti-c-Myc monoclonal antibody (9E10, Oncogene, Cambridge, Mass.) followed by a rhodamine-conjugated goat anti-mouse IgG secondary antibody (Sigma, St. Louis, Mo.). Nuclear DNA counterstaining was performed with Hoechst 33258 at a concentration of 1 $\mu$/ml.

Cell culture

Primary rat aortic smooth muscle cells were maintained in DMEM medium supplied with 10% fetal calf serum, 4 mM L-glutamine, 10 mM HEPES, 100 U/ml penicillin and 100 ng/ml streptomycin. Primary rat microvascular endothelial cells were maintained in DMEM medium supplied with 20% fetal calf serum, 4 mM L-glutamine, 100 U/ml penicillin and 100 ng/ml streptomycin.

BAEC were isolated and cultured in Dulbecco's modified Eagle's medium (JRH Biosciences, Lenexa, Kans.) supplemented with 10% fetal calf serum (HyClone, Logan, Utah), 600 $\mu$pg of glutamine/ml, 100 units of penicillin/ml, and 100 $\mu$pg of streptomycin/ml.

HepG2 human hepatoma cells (ATCC HB-8065), U-2 OS human osteosarcoma cells (ATCC HTB-96), HeLa human epidermoid carcinoma cells (ATCC CRL-7923), HepG2 human hepatoma cells (ATCC HB-8065), and NIH 3T3 mouse fibroblasts (ATCC CRL-1658) are available from the American Type Culture Collection.

Plasmid DNA purification

The mini- (<20 $\mu$g) and midiscale (<200 $\mu$g) preparations of plasmid DNA were purified by DNA-affinity chromatography (Qiagen). Large scale purification of plasmid DNA was carried out according to the alkaline lysis/CsCl ultracentrifugation methods (Ausubel, F. M., et al., ed. Current Protocols in Molecular Biology. ed. K. Janssen., 1994, Vol. 1, Current Protocols: 1.7.1-11).

Purification of recombinant $\lambda$qt11 DNA

Single positive plaques were picked and soaked in the suspension medium (0.1M NaCl, 10 mM $MgSO_4$, 50 mM TrisCl, pH 7.5, and 0.01% gelatin) with one drop of $CHCl_3$. Freshly prepared E. coli strain Y1090 competent cells were mixed and incubated briefly with the resuspended phage. The infected cells were grown overnight in LB medium with 10 mM $MgSO_4$ and 0.2% maltose. The next morning one drop of chloroform was added into the medium to lyse the bacterial cells for 15 minutes. Bacterial debris was collected by centrifugation, and to the clear supernatant 100 U DNase I and 100 ng RNase A were added to digest E. coli genomic DNA and RNA. The solutions of EDTA, TrisCl (pH 8.0), NaCl, and proteinase K were added subsequently to final concentrations of 50 mM, 100 mM, 200 mM, and 100 ng/ml, respectively. The mixture was incubated at 42° C. for 30 minutes. Phage DNA was then phenol/chloroform extracted once and precipitated by adding 0.6× volume of isopropanol in the presence of 300 mM NaOAc. Precipitated phage DNA was recovered by centrifugation and washed with 70% ethanol, air dried, then dissolved in 250 $\mu$l TE buffer (10 mM TrisCl, pH 8.0, 1 mM EDTA).

Cloning APEG-1 genes

Figure 1:
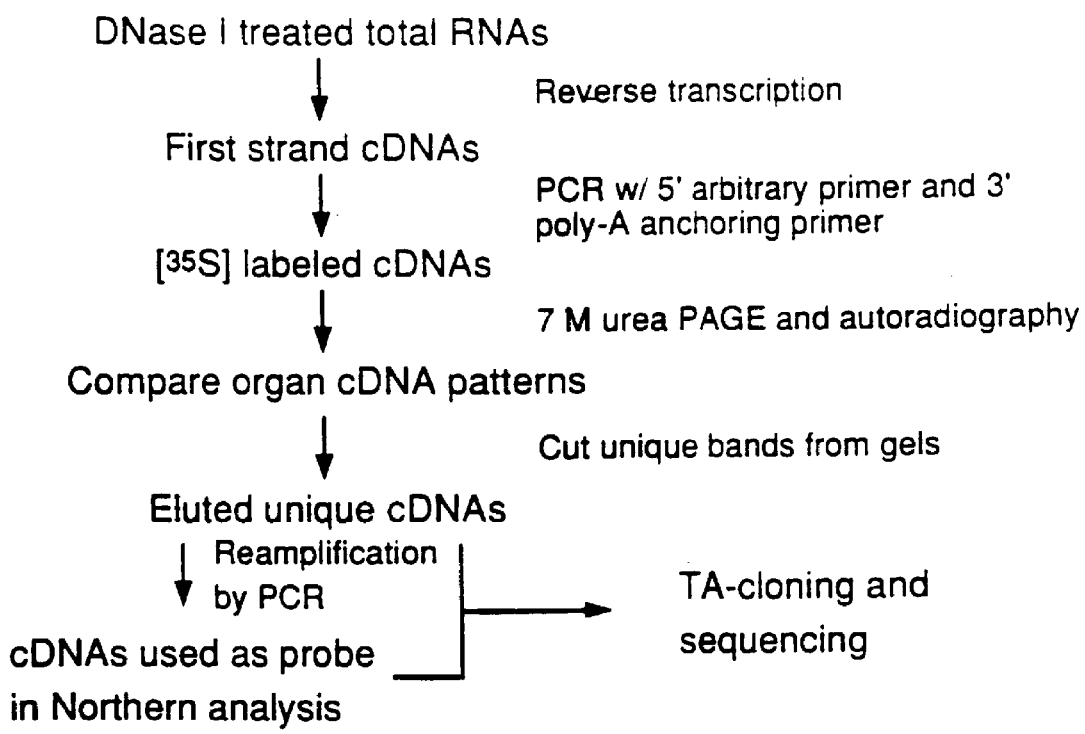

To clone genes that are preferentially expressed in the aorta, total organ RNA was prepared from rat aorta with the adventitia removed, and from brain, skeletal muscle, esophagus, heart, and intestine. Using the differential mRNA display technique, a technique that systematically amplifies mRNAs by means of RT-PCR with different sets of 5' arbitrary primers and 3' oligo-dT anchoring primers, the mRNA patterns of different organs were compared. The PCR products were resolved on a denaturing polyacrylamide sequencing gel to display mRNA patterns that distinguish one organ from another. The bands that were separated by gel electrophoresis represent the 3'-termini of the cDNAs. Therefore, a band that is present in one organ but not in the others suggests that the gene is only expressed in that particular organ (FIG. 1). Specific mRNAs that were present solely in the aorta were identified and cloned.

The organ RNAs were screened with thirty-three 5' arbitrary primers in combination with a $T_{12}VG$ 3' oligo-dT anchoring primer. This initial screening covered 21 percent of the 160 primer combinations needed to screen all possible mRNAs to be displayed by this technique. This estimate is based on the assumption that one primer combination displays about 100 different mRNAs from approximately 15,000 different mRNA species present in each cell.

From the initial screening, seventeen bands that were present solely in the aorta were identified. These bands were cut from the gel and the cDNA fragments eluted and reamplified by PCR with the same primers that were used in their original RT-PCRs. These reamplified cDNAs were $^{32}$P-labeled, then used in Northern blot analyses to confirm their aortic specificity. Four cDNA fragments were found to be aorta-specific (FIGS. 2A–2I). After cloning these four cDNA fragments by TA-cloning methods, the clones were designated APEG-1, APEG-2, APEG-3, and APEG-4. Their DNA sequences were determined by the dideoxynucleotide chain termination method and compared to known DNA sequences listed in the GENBANK® database. APEG-2 showed identical sequences to the rat SM22 gene (Shanahan, C. M., et al., 1993, Circ. Res. 73(1):193–204), a smooth muscle cell specific gene. APEG-4 was found to have a near-identical sequence to chicken and mouse TIMP-3 genes (tissue inhibitor of metalloproteinase-3) (Sun, Y., et al., 1994, Cancer Res. 54:1139–44; Leco, K. J., et al., 1994, J. Biol. Chem. 269(12):9352–60). APEG-1 and APEG-3 did not match any known genes. Further examination of the tissue distribution of expression showed that APEG-3 was also expressed in the lung, a result not seen in the initial Northern blot analysis. In contrast, APEG-1 showed the highest expression in the aorta among twelve rat organs (FIGS. 3A–3D), thus confirming the specificity of tissue expression.

Cloning and sequence analysis of rat APEG-1 cDNA

The APEG-1 3' cDNA fragment, derived from differential mRNA display, was used to screen a rat aortic cDNA library (FIG. 4). The cloned APEG-1 cDNA was determined to be 1,308 base pairs, consistent with the size of the message seen in Northern blot analysis. Sequences of both cDNA strands were determined by dideoxynucleotide chain termination sequencing with fragment-subcloning and oligonucleotide-walking strategies. The complete cDNA sequence had no homologous counterpart in the GENBANK® database.

The rat APEG-1 cDNA can then be used to screen a genomic library to obtain the vascular cell-specific promoter sequences which regulate expression cell-specific expression of APEG-1.

To analyze the protein encoded in APEG-1 cDNA, the sequence was searched for possible ATG initiation codons for translation from the 5' end of the sequence. The longest open reading frame in the rat APEG-1 cDNA (SEQ ID NO:1) spans from 169 to 511 nucleotides (SEQ ID NO:2) downstream of the 5' end of the cDNA. Another ATG sequence was found at nucleotide 102 to 104 (FIG. 5), but the possible translation from this preceding ATG codon is terminated after four amino acid residues, thus making it unlikely to be the initiation codon used in vivo. The longest open reading frame has a Kozak consensus sequence (Kozak, M., 1987, J. Mol. Biol. 196:947–50) and encodes a protein of 113 amino acids (SEQ ID NO:3) with a predicted molecular weight of 12,667 daltons and an estimated pI of 9.125 (FIG. 6). This predicted translation product was confirmed by in vitro transcription and in vitro translation of the APEG-1 cDNA, which yielded a major translation product of 12.7 kDa as predicted by the deduced amino acid sequence from the longest open reading frame (FIGS. 7A–7B). Comparison of the APEG-1 deduced amino acid sequence to the SwissProt protein database again showed no identical protein sequence. However, a region was identified that is homologous to proteins of the myosin light chain kinase family, which includes myosin light chain kinases and telokin (FIG. 8).

The myosin light chain kinases (MLCKs), present in all eukaryotic cells, are members of the $Ca^{2+}$-calmodulin-dependent protein kinases. They phosphorylate the 20 kDa light chain subunit of myosin, a protein that is important in regulating contraction of smooth muscle cells, secretory vesicle movement, cellular locomotion, and changes in cellular morphology (Gallagher, P. J., et al., 1991, J. Biol. Chem. 266(35):23945–52). The structure of MLCKs is highly conserved and composed of several modular domains. The MLCK carboxyl terminus is the calmodulin-binding domain and has a regulatory function mediated by two specific serines residues which become phosphorylated by cAMP-dependent protein kinase. Phosphorylation at these two sites downregulates MLCK kinase activity by decreasing the affinity of MLCK for $Ca^{2+}$-calmodulin. One of the two phosphorylated serine residues in the MLCK C-terminus is conserved in APEG-1 (Ser12), suggesting a regulatory site of APEG-1.

Telokin, originally purified as an acidic protein from turkey gizzard, is a protein that has the same peptide sequence as the carboxyl terminal domain of MLCKs. Its mRNA transcription initiates from a promoter that is located in one of the MLCK introns. Telokin transcription regulation is independent from that of MLCK despite having a sequence identical to the MLCK carboxyl terminal domain. Telokin has been proposed to be a calmodulin-binding protein (Holden, H. M., et al., 1992, J. Mol. Biol. 227:840–51), and it is expressed in almost every smooth muscle cell, except in the aortic smooth muscle cell. It is not expressed in any non-muscle cells (Gallagher, P. J., et al., supra).

When the APEG-1 polypeptide sequence was compared with those of MLCKs, there was a 33% identity at the amino acid level. However, several lines of evidence indicate that APEG-1 is not a rat homologue of a MLCK. First, peptide sequence comparison of APEG-1 to rat smooth muscle MLCK has only 24% identity, significantly less than the identity between APEG-1 and rabbit or chicken MLCKs. Second, the APEG-1 protein is predicted to be a basic protein, whereas the telokin protein is acidic. Third, rabbit telokin is not expressed in the aorta, in contrast to the specific expression pattern of APEG-1.

When the APEG-1 protein was analyzed to identify sequence motifs, several residues were identified as capable of being phosphorylated by protein kinase C and casein kinase-2. An arg-gly-asp (RGD) peptide sequence was found at position 90–92. This motif is present in many proteins involved in cell adhesion as well as signaling, and it interacts with its cell surface receptor, an integrin (Hynes, R. O., 1992, Cell 69:11–25, Ruoslahti, E., et al., 1987, Science 238:491–6). This observation suggests that APEG-1 protein plays role in cell signaling. The motif of two cysteine residues, four residues upstream and six residues downstream of the integrin-binding RGD sequence, are also conserved in the disintegrins, a family of platelet aggregation inhibitors found in snake venom (Blobel, C. P., et al., 1992, Curr. Opin. Cell. Biol. 4:760–5). The cysteine residue 6 residues downstream of the RGD sequence was also found to be present in the APEG-1 protein.

Cloning of mouse APEG-1

The mouse cDNA encoding an APEG-1 open reading frame was first amplified from mouse aortic RNA by reverse transcription polymerase chain reaction (RT-PCR) with primers conserved between the rat and human sequences. Using nested primers designed according to the open reading frame of mAPEG-1, the 3' end of the mouse cDNA was obtained by 3' RACE. Both strands of the entire mouse APEG-1 cDNA were sequenced at least once by the dideoxy chain termination sequencing method.

Northern and Genomic Southern Analyses of APEG-1

The APEG-1 full length cDNA was used as the probe to hybridize a 12-organ RNA Northern blot. In addition to the 1.3 kb message that appeared in the aorta, two other much larger messages (10–20 kb) were observed in skeletal muscle, esophagus, and heart. These two large messages were not initially identified by the APEG-1 3'-probe; therefore, it is likely the 5' sequence of APEG-1 cDNA hybridized to these new signals. To test this possibility further, three different probes from the 5', the middle, and the 3' portions of the APEG-1 cDNA sequence were used in Northern analysis (FIG. 9A). The result indicated that these 10–20 kb messages were recognized by the 5' but not by the 3' portion of the APEG-1 cDNA (FIGS. 9B–9D).

To determine the relationship of the 1.3 kb aortic transcript and the larger transcripts, a series of probes spanning the APEG-1 gene was used in Northern blot hybridization analyses of RNA isolated from rat aorta, heart, and skeletal muscle. This analysis revealed that the APEG-1 gene defines a muscle cell-specific protein family that encodes both smooth muscle cell-specific proteins and striated muscle cell-specific proteins. The APEG-1 transcripts were detected only in aortic RNA. The large transcripts correspond to variant isoforms, which have been named SPEGs. SPEGs are detected in striated muscle RNA (skeletal and cardiac tissue) but were not seen in aortic RNA.

The patterns of exon usage in APEG-1 and SPEGs are shown in FIGS. 19A–C. The APEG-1 gene spans 4.5 kb and is composed of five exons and four introns. SPEG-specific probes detect transcripts 10 and 12 kb in size that are composed of at least seven exons. Three of these exons are shared with the APEG-1 gene, while at least four are unique. The first exon of APEG-1 is separated from the closest upstream SPEG exon by 7 kb. The differential tissue expression patterns of APEG-1 and SPEG arise from utilization of different promoters, alternative splicing, or a combination of the two mechanisms.

The partial nucleotide and amino acid sequences of human SPEG are shown in FIG. 20 and FIG. 21, respectively. The partial nucleotide and amino acid sequences of mouse SPEG are shown in FIGS. 22 and 23, respectively. A comparison of the human and mouse partial SPEG amino acid sequences is shown in FIG. 27.

To determine whether a smooth muscle cell specific promoter exists 5' to the first APEG-1 exon, a 3.3 kb APEG-1 5' flanking sequence was used in a reporter gene transfection analysis using the luciferase reporter plasmid pGL3-C. As shown in FIGS. 24A–B, a high level of promoter activity directed by the APEG-1 5' flanking sequence was detected in both rat aortic smooth muscle cells human aortic smooth muscle cells. In contrast, as shown in FIG. 24A–B, minimal activity was detected in five non-smooth muscle cell types, including human cell lines HeLa, HepG2, and U-2 OS.

The sequences responsible for directing a high level of promoter activity have been further localized within the 3.3 kb fragment to the 2.7 kb sequence shown in FIG. 25.

If desired, sequences responsible for conferring smooth muscle cell-specificity in the 5' APEG-1 region can be localized more precisely within the 5' region using methods well-known in the art, e.g., by constructing plasmids containing successively smaller portions of the 2.7 kb 5' fragment placed upstream of a luciferase reporter gene (or any of the many reporter genes known in the art) in a construct such as pGL3, transfecting the construct into arterial smooth muscle cells, and determining if the upstream sequence directs expression of the reporter gene. Increased expression of the reporter gene in arterial smooth muscle cells compared to other cell types (i.e., non-smooth muscle cells) indicates that the DNA directs polypeptide expression in a cell specific manner.

Sequences capable of directing striated muscle specific expression of the SPEGs exons are determined by performing the above-described cell transfection assays using sequences 5' to the first SPEG exon.

Expression of APEG-1 and SPEG in mouse development

The full-length APEG-1 cDNA was used to probe RNA isolated from mouse embryos at different times in embryonic development. RNA was isolated from the entire embryo for these experiments. The APEG-1 probe hybridized to a 1.3 kb RNA from embryos beginning 9.5 days post-coitus (p.c.) and continuing to 20 days p.c. Strong hybridization was observed to RNA from embryos 11.5 to 20 days p.c.

APEG-1 transcript levels were also examined post-natally in RNA isolated from rat heart tissue. Hybridization to the APEG-1 probe was detectable in RNA from two-day old rats, but only faint hybridization was detected in RNA from rats aged 14 and 28 days. In situ hybridization experiments of post-natal heart tissue using the APEG-1 probe also revealed a decreased level of APEG-1 RNA. Interestingly, as APEG-1 RNA levels decreased, the levels of SPEG RNAs in striated muscle increased.

When considered with the tissue specific expression data, these results suggest that APEG-1 transcript levels are high during embryonic development, particularly at day 11.5 p.c. and thereafter. Post-natally, APEG-1 transcript levels, e.g., in cardiac muscle. was generally found to decrease. As global APEG-1 levels decreased, SPEG transcript levels in striated muscle cells increased.

Southern blot analysis suggested that APEG-1 has a single copy in the rat genome, because there was only one 17.1 kb band in the EcoR I-digested rat genomic DNA (FIG. 10). This result further indicated that the large messages are unlikely to be products of other genes, unless these other genes are closely linked with APEG-1 without any intervening EcoR I sites. From the APEG-1 cDNA sequence two BamH I and one Hind III site were located (FIG. 9A). This correlated with the Southern analysis data in that three bands (18.7, 2.4, and 1.4 kb) in BamH I- and two bands (12.0 and 6.4 kb) in HindIII-digested genomic DNA were identified.

Cloning of the human APEG-1 cDNA

The APEG-1 cDNA probe was used to screen a human λgt11 aortic 5'-stretch cDNA library (Clontech). Four positive clones were purified, and the insert cDNA was sized by EcoRI digestion of the phage DNA and sequenced. The sequence of the human APEG-1 cDNA and the predicted amino acid sequence of the open reading frame encoding human APEG-1 are shown in FIG. 16 and FIG. 17, respectively.

The human APEG-1 cDNA can then be used to screen a genomic library to obtain the vascular cell-specific promoter sequences which regulate expression cell-specific expression of APEG-1.

Comparison of the human, mouse, and rat APEG-1 peptide sequences

FIG. 26 shows the aligned human, mouse, and rat APEG-1 peptide sequences, along with a derived consensus sequence (SEQ ID NO:12, 18, 13, and 19). A comparison of the human and rat open reading frames revealed 90% identity at the cDNA level and 97% identity at the amino acid level. Comparison of the open reading frames of mouse and rat APEG-1 revealed 95% identity at the cDNA level and 98% identity at the amino acid level. Thus, APEG-1 is highly conserved across species.

Deposit

A plasmid containing DNA encoding rat APEG-1 (rat APEG-1 cDNA in pSP72 vector) has been deposited with the American Type Culture Collection (ATCC) under the terms of the Budapest Treaty on the International Recognition of the Deposit of Microorganisms for the Purpose of Patent Procedure on Mar. 3, 1995, and bears the accession number ATCC 97071. A plasmid containing DNA encoding human APEG-1 (human APEG-1 cDNA in pUC18 vector) was deposited with the American Type Culture Collection under the terms of the Budapest Treaty on Jun. 1, 1995, and bears the accession number ATCC 97180. A deposit of a plasmid clone containing 2.7 kb of 5' flanking sequence of the mouse APEG-1 gene was deposited with the ATCC. on Feb. 5, 1997. Applicants' assignee, President and Fellows of Harvard College, acknowledges its duty to replace the deposit should the depository be unable to furnish a sample when requested due to the condition of the deposit before the end of the term of a patent issued hereon, and its responsibility to notify the ATCC of the issuance of such a patent, at which time the deposit will be made available to the public. Prior to that time, the deposit will be made available to the Commissioner of Patents under the terms of CFR §1.14 and 35 U.S.C. §112.

The absence of APEG-1 expression in primary culture cells

As discussed above, APEG-1 was initially identified in adventitia-removed aortic tissue, a tissue composed of smooth muscle cells and endothelial cells. To identify which of these two cell types express APEG-1 gene, total RNAs were harvested from primary cultured rat aortic smooth muscle cells and microvascular endothelial cells, both at the second passage, and these RNAs were used in Northern analysis. APEG-1 message was not detected in these cell types (FIG. 12). It is likely that the in vivo expression of APEG-1 was lost during in vitro cell culture. These data suggest that APEG-1 expression is strictly growth-regulated, such that its expression is downregulated when cells are growing in vitro, as has been observed with respect to gas1 gene expression (Sal, G. D., et al., 1992, Cell 70:595–607). Alternatively, since cultured smooth muscle cells are believed to exhibit a dedifferentiated phenotype (Pauly, R. R., et al., 1992, Circulation 86 (suppl III):III-68–73), APEG-1 may be expressed solely in fully differentiated endothelial or smooth muscle cells. Consistent with a role in maintaining a differentiated phenotype, which is characterized by the absence of cell division, microinjected APEG-1 inhibited BrdU uptake in rat arterial smooth muscle cells. APEG-1 expression in vivo was found to be vascular smooth muscle cell-specific, as shown in FIGS. 18A and 18B.

APEG-1 expression in the balloon injury animal model

Since APEG-1 gene expression in vitro is different from that in vivo, APEG-1 expression in vivo was studied. A balloon injury model of the rat carotid artery, which has been used extensively to study vascular smooth muscle cells in atherogenesis and vascular remodeling (Clowes, A. W., et al., 1983, Lab. Invest. 49(2):208–15, Clowes, A. W. et al., 1985, Circ. Res. 56:139–45), was used to study the expression modulation of APEG-1. In this animal model, the rat left carotid artery was injured by a 2F balloon catheter, intimal arterial endothelial cells completely removed, and the medial smooth muscle cell layer distended. After the carotid injury, formation of the neointima was initiated. This involves smooth muscle cells proliferating and migrating from the media. With this model, medial and neointimal smooth muscle cells reach their respective highest rates of proliferation two days and four days after the balloon injury, declining rapidly thereafter. The total number of smooth muscle cells approaches a maximum and remains constant after two weeks (Clowes, A. W. et al., 1985, supra).

Total RNAs from rat carotid arteries 2, 5, and 8 days after balloon injury were collected and used in Northern analysis with an APEG-1 cDNA probe. The results showed that APEG-1 is downregulated to 15%–20% of non-injured carotid arteries after 2 and 5 days; the expression recovered to 40% of control after 8 days (FIGS. 13A and 13B). These data suggest that APEG-1 expression is involved in the regulation of smooth muscle cell proliferation and/or migration, and expression has to be suppressed for either or both events to occur.

Production and purification of recombinant APEG-1

Recombinant APEG-1 was expressed as a fusion protein and purified by the pFLAG expression system (IBI) and subsequently injected into rabbit to produce antiserum. The rat APEG-1 cDNA was cloned into pFLAG-2 expression vector and used to transform the E. coli BL21 cells. The transformed cells were grown and induced by IPTG (isopropyl-β-D-thio-galactopyroside) to express the vector-encoded fusion protein. The FLAG-APEG-1 fusion protein was then purified by anti-FLAG monoclonal antibody affinity chromatography from soluble cell extract, and the purity was monitored by both Coomassie blue staining (FIG. 14A) and Western analysis (FIG. 14B).

APEG-1 cellular localization

To determine the cellular localization of APEG-1, a plasmid was generated, c-myc-rAPEG-1/pCR3, that would express a fusion protein of APEG-1 with an N-terminal c-Myc tag. COS-7 cells were then transiently transfected with the c-myc-rAPEG-1/pCR3 plasmid and immunostained with a monoclonal anti-c-Myc antibody, 9E10. The c-Myc-tagged protein was expressed predominantly in the nuclei of transfected COS-7 cells. The same result was obtained when U-2 OS cells were used as the host cells.

Methods of Diagnosis

The invention includes a method of detecting injury in a sample of vascular tissue. A depressed level of APEG-1 would predict a high degree of smooth muscle cell proliferation indicative of vascular tissue injury, e.g., restenosis. The diagnostic method of the invention is carried out by determining the level of APEG-1 gene expression in a tissue, e.g, a vascular biopsy obtained at atherectomy. The level of gene expression may be measured using methods known in the art, e.g., in situ hybridization, Northern blot analysis, or Western blot analysis using APEG-1-specific monoclonal or polyclonal antibodies. A decrease in the level of APEG-1 expression per cell in the test sample of tissue compared to the level per cell in uninjured control vascular tissue indicates the presence of a vascular injury in the test sample. For example, tissue obtained at atherectomy could be tested for APEG-1 expression, e.g., the level of APEG-1 transcript or protein. A depressed level of APEG-1 (compared to normal tissue) correlates with a high degree of smooth muscle cell proliferation indicating a high probability of restenosis. Such diagnostic procedures are useful to identify patients in need of therapeutic intervention to reduce or prevent restenosis.

Methods of Detecting Specific Types of Muscle Cells

Because APEG-1 and SPEG mRNAs are enriched in vascular smooth muscle cells and in striated muscle cells, respectively, the APEG-1 and SPEG nucleic acid sequences can be used as probes to identify these cell types. For example, an APEG-1 specific nucleic acid sequence, e.g., a probe corresponding to an APEG-1 specific exon, is hybridized, using methods well known in the art, to RNA sequences in Northern blot hybridization studies or using in situ hybridization assays. Reactivity to an APEG-1 specific probe is indicative of a vascular smooth muscle cell tissue. Similarly, a SPEG-specific nucleic acid sequence, e.g., a probe corresponding to a SPEG-specific exon, is used to identify striated muscle cells.

APEG-1 and SPEG DNA sequences can also be used to make recombinant APEG-1 and SPEG polypeptides, or fragments thereof. Monoclonal or polyclonal antibodies are then raised to the recombinant polypeptides using methods well-known in the art. The anti-SPEG antibodies are then used, e.g., in western or immunofluorescence experiments, to identify vascular smooth muscle cells, in the case of APEG-1, or striated muscle cells in the case of SPEG.

Methods of Therapy

Upon vascular injury and other stimuli, cytokines and growth factors from activated vascular cells promote growth and migration of dedifferentiated vascular smooth muscle cells, resulting in atherosclerotic plaques and restenosis. Administration of APEG-1 polypeptide to vascular smooth muscle cells in vitro (by microinjection) resulted in a decrease in DNA synthesis, indicative of a decrease in cellular proliferation. Vascular injury such as that caused during surgery or balloon angioplasty can be treated by administering APEG-1 polypeptides or DNA encoding APEG-1 polypeptides operably linked to appropriate expression control sequences. Other vascular conditions, e.g., atherosclerosis, transplant arteriosclerosis, and diabetes, which are characterized by a decrease in APEG-1 expression (FIG. 15) may be treated in a similar manner. APEG-1 polypeptide, DNA encoding an APEG-1 polypeptide, or compositions which stimulate the APEG-1 promoter may administered to increase the level of APEG-1 polypeptide in the injured vascular tissue and thus inhibit the growth of smooth muscle cells.

APEG-1 polypeptides may be administered to the patient intravenously in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 μmoles of the polypeptide of the invention would be administered per kg of body weight per day. The compositions of the invention are useful for parenteral administration, such as intravenous, subcutaneous, intramuscular, and intraperitoneal.

DNA (e.g., APEG-1-encoding DNA, vascular cell-specific promoters (e.g., SEQ ID NO:17), SPEG-encoding DNA, and striated muscle cell-specific promoters) and vectors of the invention may be introduced into target cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others. For example, the DNA under encoding an APEG-1 or SPEG polypeptide under the control of a strong constitutive promoter may be administered locally to a blood vessel during balloon angioplasty using an adenovirus delivery system.

A vascular cell-specific promoter or promoter/enhancer sequence derived from the APEG-1 gene (e.g., SEQ ID NO:17) may be used to direct the expression of APEG-1 or genes other than APEG-1. Thus, vascular diseases may be treated by administering a vascular cell-specific promoter/enhancer sequence of the invention operably linked to a sequence encoding a heterologous polypeptide, e.g., an APEG-1 promoter linked to DNA encoding a growth inhibitor gene such as Rb, p21 or p18.

The DNA may encode a naturally occurring mammalian APEG-1 polypeptide such as a rat APEG-1 polypeptide (SEQ ID NO:3) or human APEG-1 polypeptide (SEQ ID NO:12). For example, the invention includes degenerate variants of SEQ ID NO:2 or SEQ ID NO:11. The invention also includes a substantially pure DNA comprising a strand which hybridizes at high stringency to a DNA having the sequence of SEQ ID NO:1, 2, or 11, or the complements thereof.

Similarly, a striated muscle cell specific-promoter may be used to direct expression of SPEG or genes other than SPEG. Thus, striated muscle diseases may be treated by administering a striated muscle cell-specific promoter of the invention operably linked to a sequence encoding a heterologous polypeptide, e.g., a SPEG promoter linked to DNA encoding a therapeutic gene, e.g., dystrophin to treat Duchenne's or Becker's muscular dystrophy, or a growth inhibitor gene such as Rb, p21, or p18, to reduce undesirable proliferation of striated muscle cells.

The DNA of the invention may be administered in a pharmaceutically acceptable carrier. The therapeutic composition may also include a gene delivery system as described above. Pharmaceutically acceptable carriers are biologically compatible vehicles which are suitable for administration to an animal e.g., physiological saline. A therapeutically effective amount is an amount of the nucleic acid of the invention which is capable of producing a medically desirable result in a treated animal.

As is well known in the medical arts, dosage for any given patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule. Determination of optimal dosage is well within the abilities of a pharmacologist of ordinary skill.

Drugs which stimulate the APEG-1 promoter may also be administered as described above to increase the level of expression APEG-1 in vascular tissue. Such drugs can be identified by contacting the APEG-1 promoter linked to a reporter gene with a candidate compound and measuring the level of expression of the reporter gene in the presence and absence of the compound. An increased level of expression in the presence of the compound compared to that in its absence indicates that the compound stimulates the APEG-1 promoter.

The invention also includes cells transfected with the DNA of the invention. Standard methods for transfecting cells with isolated nucleic acid are well known to those skilled in the art of molecular biology. Preferably, the cells are vascular smooth muscle cells, and they express an APEG-1 polypeptide of the invention encoded by the nucleic acid of the invention. Cells of the invention may be administered to an animal locally or systemically using intravenous, subcutaneous, intramuscular, and intraperitoneal delivery methods. Alternatively, prokaryotic or eukaryotic cells in culture can be transfected with the DNA of the invention operably linked to expression control sequences appropriate for high-level expression in the cell. Such cells are useful for producing large amounts of the APEG-1 polypeptide, which can be purified and used, e.g., as a therapeutic or for raising anti-APEG-1 antibodies.

Other embodiments are within the following claims.

What is claimed is:

1. A substantially pure DNA comprising an APEG-1 promoter/enhancer sequence, wherein said promoter/enhancer sequence is operably linked to a polypeptide-encoding sequence and regulates vascular smooth muscle cell-specific transcription of said polypeptide-encoding sequence.

2. The DNA of claim 1, wherein said promoter/enhancer sequence comprises SEQ ID NO:17.

3. The DNA of claim 1, wherein said promoter/enhancer sequence regulates developmental stage-specific expression of said polypeptide-encoding sequence.

4. The DNA of claim 1, wherein said polypeptide-encoding sequence does not encode APEG-1.

5. A vector comprising the DNA of claim 4.

6. A method of directing vascular smooth muscle cell-specific expression of a polypeptide, comprising introducing into a vascular smooth muscle cell the vector of claim 5; and expressing the polypeptide-encoding sequence.

7. A method of directing developmental stage-specific expression of a polypeptide, comprising introducing into a vascular smooth muscle cell the vector of claim 5; and expressing the polypeptide-encoding sequence.

8. The DNA of claim 1, wherein said polypeptide is chosen from the group consisting of tissue plasminogen activator, p21 cell cycle inhibitor, nitric oxide synthase, interferon-γ, and atrial natriuretic polypeptide.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 1308 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:1:

```
GAATTCGGCA  CGAGCAGAGA  CTTAAGGAAG  GTGCAGACGG  GGTCCGTTTG  CACAGCCTCA        60

GGGCGCGTCC  ACATCCCCCT  TCAGCAGCCC  AATCACCTCT  GATGAGGAGT  ACCTGAGCCC       120
```

| | | | | | | |
|---|---|---|---|---|---|---|
|CCCAGAGGAG|TTCCCAGAAC|CTGGGGAGAC|CTGGTCCCGA|ACCCCTACCA|TGAAGCCCAG|180|
|TCCCAGCCAG|GATCGAGATT|CCTCTGACTC|TTCCTCCAAG|GCACCCCCAA|CCTTCAAGGT|240|
|CTCACTCATG|GACCAATCAG|TGAGAGAAGG|TCAAGATGTC|ATTATGAGCA|TCCGCGTGCA|300|
|GGGGGAGCCC|AAGCCTGTGG|TCTCCTGGCT|GAGGAATCGG|CAGCCTGTGC|GCCCAGACCA|360|
|GCGGCGCTTT|GCAGAGGAGG|CCGAGGGTGG|GCTCTGCCGG|TTGAGGATCC|TGGCTGCTGA|420|
|GAGGGGAGAT|GCTGGTTTCT|ACACTTGCAA|GGCGGTCAAC|GAATATGGCG|CTCGGCAGTG|480|
|TGAGGCCCGC|CTGGAGGTCC|GAGGCGAGTG|AGCTCAGGGG|GCCACCTGCG|CTGCCCCGC|540|
|TACCCTCCGA|GCTGCACCCC|TGTCTCAGGC|ACCTCCTGGA|CCTCGCTGTG|TTTCACTGCC|600|
|TCCTGCCCAC|AGACCCAGCC|GGCTCGCCGG|CCCGGACATA|GCCATGCTC|CCCTTCCCTC|660|
|CCTAGCCCAT|ACAGCACCCT|GGGGTAACCC|ATCGGGCCCC|TGTGGATCCT|CCCTCCCCAA|720|
|GTGGATATGT|GGCTGTGCAG|ACCAGGAGGC|CCCCAGAAGG|ACTGAGTGTT|GAGAAGGGAT|780|
|GGCCATGAGG|TTGTGACAAG|CTCCCCCCGT|CCCCAGCCTC|CATGTAGGGA|GCATCCAGCG|840|
|AATGCATGTG|CTATGCTGCT|ACAGGCCACT|GTCTGTCTCT|CTGTCTGTCT|GCCTGTGTGT|900|
|CTGTGACAGT|CAGGGAAGAA|AACCTTCGAG|CTGAGGTGGG|ATAAGACAGA|ATAAGATGAT|960|
|AGAACACAGC|ATCTGTGAGA|TGCAGGGGCC|CAGAGGGGCA|GGCACAGTGG|ATAGGAGACT|1020|
|CTCTGGGAAG|GGTAGGGCAC|TGACCATTGC|AGAAATGGGT|TTTAAATGGC|ACAACATTTT|1080|
|TTATTCCACA|TGAGACCAAA|AGCTAGAGGT|CTGGGATTAA|GCCCTGACTG|CTGGCAAGCT|1140|
|TAGGACCAAG|TGGGGTACCC|TTCTTCACAG|ACACATCCGA|CACGCTCTGT|CTGGGAATGA|1200|
|GAGAGTAGCC|AGACTGAGCA|CAGGAGCAGG|TCATAGTGGG|ACTGGAGGTT|TGGAAACACT|1260|
|ATTTCGTAGC|TCAAATAAAG|TCCAGTTTGT|ACCCAAAAAA|AAAAAAA| |1308|

( 2 ) INFORMATION FOR SEQ ID NO:2:

( i ) SEQUENCE CHARACTERISTICS:
        ( A ) LENGTH: 342 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:2:

| | | | | | | |
|---|---|---|---|---|---|---|
|ATGAAGCCCA|GTCCCAGCCA|GGATCGAGAT|TCCTCTGACT|CTTCCTCCAA|GGCACCCCA|60|
|ACCTTCAAGG|TCTCACTCAT|GGACCAATCA|GTGAGAGAAG|GTCAAGATGT|CATTATGAGC|120|
|ATCCGCGTGC|AGGGGGAGCC|CAAGCCTGTG|GTCTCCTGGC|TGAGGAATCG|GCAGCCTGTG|180|
|CGCCCAGACC|AGCGGCGCTT|TGCAGAGGAG|GCCGAGGGTG|GGCTCTGCCG|GTTGAGGATC|240|
|CTGGCTGCTG|AGAGGGGAGA|TGCTGGTTTC|TACACTTGCA|AGGCGGTCAA|CGAATATGGC|300|
|GCTCGGCAGT|GTGAGGCCCG|CCTGGAGGTC|CGAGGCGAGT|GA| |342|

( 2 ) INFORMATION FOR SEQ ID NO:3:

( i ) SEQUENCE CHARACTERISTICS:
        ( A ) LENGTH: 113 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:3:

Met   Lys   Pro   Ser   Pro   Ser   Gln   Asp   Arg   Asp   Ser   Ser   Asp   Ser   Ser   Ser

```
  1               5                    10                   15
Lys Ala Pro Pro Thr Phe Lys Val Ser Leu Met Asp Gln Ser Val Arg
            20                  25                  30
Glu Gly Gln Asp Val Ile Met Ser Ile Arg Val Gln Gly Glu Pro Lys
            35                  40                  45
Pro Val Val Ser Trp Leu Arg Asn Arg Gln Pro Val Arg Pro Asp Gln
            50                  55                  60
Arg Arg Phe Ala Glu Glu Ala Glu Gly Gly Leu Cys Arg Leu Arg Ile
65                      70                  75                  80
Leu Ala Ala Glu Arg Gly Asp Ala Gly Phe Tyr Thr Cys Lys Ala Val
                85                  90                  95
Asn Glu Tyr Gly Ala Arg Gln Cys Glu Ala Arg Leu Glu Val Arg Gly
            100                 105                 110
Glu
```

( 2 ) INFORMATION FOR SEQ ID NO:4:

( i ) SEQUENCE CHARACTERISTICS:
        ( A ) LENGTH: 157 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:4:

```
Met Ala Met Ile Ser Gly Met Ser Gly Arg Lys Ala Gly Gly Ser Ser
1                   5                   10                  15
Pro Thr Ser Pro Ile Asn Ala Asp Lys Val Glu Asn Glu Asp Ala Phe
            20                  25                  30
Leu Glu Glu Val Ala Glu Glu Lys Pro His Val Lys Pro Tyr Phe Thr
            35                  40                  45
Lys Thr Ile Leu Asp Met Glu Val Val Glu Gly Ser Ala Ala Arg Phe
            50                  55                  60
Asp Cys Lys Ile Glu Gly Tyr Pro Asp Pro Glu Val Met Trp Tyr Lys
65                      70                  75                  80
Asp Asp Gln Pro Val Lys Glu Ser Arg His Phe Gln Ile Asp Tyr Asp
                85                  90                  95
Glu Glu Gly Asn Cys Ser Leu Thr Ile Ser Glu Val Cys Gly Asp Asp
            100                 105                 110
Asp Ala Lys Tyr Thr Cys Lys Ala Val Asn Ser Leu Gly Glu Ala Thr
                115                 120                 125
Cys Thr Ala Glu Leu Leu Val Glu Thr Met Gly Lys Glu Gly Glu Gly
    130                 135                 140
Glu Gly Glu Gly Glu Glu Asp Glu Glu Glu Glu Glu Glu
145                 150                 155
```

( 2 ) INFORMATION FOR SEQ ID NO:5:

( i ) SEQUENCE CHARACTERISTICS:
        ( A ) LENGTH: 157 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:5:

```
Met Ala Met Ile Ser Gly Met Ser Gly Arg Lys Ala Ser Gly Ser Ser
1                   5                   10                  15
```

-continued

```
Pro Thr Ser Pro Ile Asn Ala Asp Lys Val Glu Asn Glu Asp Ala Phe
            20              25              30

Leu Glu Glu Val Ala Glu Glu Lys Pro His Val Lys Pro Tyr Phe Thr
        35              40              45

Lys Thr Ile Leu Asp Met Glu Val Val Glu Gly Ser Ala Ala Arg Phe
    50              55              60

Asp Cys Lys Ile Glu Gly Tyr Pro Asp Pro Glu Val Met Trp Tyr Lys
65              70              75                          80

Asp Asp Gln Pro Val Lys Glu Ser Arg His Phe Gln Ile Asp Tyr Asp
            85              90                      95

Glu Glu Gly Asn Cys Ser Leu Thr Ile Ser Glu Val Cys Gly Asp Asp
            100             105             110

Asp Ala Lys Tyr Thr Cys Lys Ala Val Asn Ser Leu Gly Glu Ala Thr
        115             120             125

Cys Thr Ala Glu Leu Leu Val Glu Thr Met Gly Lys Glu Gly Glu Gly
    130             135             140

Glu Gly Glu Gly Glu Glu Asp Glu Glu Glu Glu Glu
145             150             155
```

(2) INFORMATION FOR SEQ ID NO:6:

(i) SEQUENCE CHARACTERISTICS:
        (A) LENGTH: 155 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

```
Met Ala Met Ile Ser Gly Leu Ser Gly Arg Lys Ser Ser Thr Gly Ser
1               5               10              15

Pro Thr Ser Pro Leu Thr Ala Glu Arg Leu Glu Thr Glu Glu Asp Val
            20              25              30

Ser Gln Ala Phe Leu Glu Ala Val Ala Glu Glu Lys Pro His Val Lys
        35              40              45

Pro Tyr Phe Ser Lys Thr Ile Arg Asp Leu Glu Val Val Glu Gly Ser
    50              55              60

Ala Ala Arg Phe Asp Cys Lys Ile Glu Gly Tyr Pro Asp Pro Glu Val
65              70              75                          80

Val Trp Phe Lys Asp Asp Gln Ser Ile Arg Glu Ser Arg His Phe Gln
            85              90                      95

Ile Asp Tyr Asp Glu Asp Gly Asn Cys Ser Leu Ile Ile Ser Asp Val
            100             105             110

Cys Gly Asp Asp Asp Ala Lys Tyr Thr Cys Lys Ala Val Asn Ser Leu
        115             120             125

Gly Glu Ala Thr Cys Thr Ala Glu Leu Ile Val Glu Thr Met Glu Glu
    130             135             140

Gly Glu Gly Glu Gly Glu Glu Glu Glu Glu Glu
145             150             155
```

(2) INFORMATION FOR SEQ ID NO:7:

(i) SEQUENCE CHARACTERISTICS:
        (A) LENGTH: 155 amino acids
        (B) TYPE: amino acid
        (C) STRANDEDNESS: Not Relevant
        (D) TOPOLOGY: linear (i) MOLECULE TYPE: protein (xi) SEQUENCE DESCRIPTION: SEQ ID NO:7:

| Met | Ala | Met | Ile | Ser | Gly | Leu | Ser | Gly | Arg | Lys | Ser | Ser | Thr | Gly | Ser |
|---|---|---|---|---|---|---|---|---|---|---|---|---|---|---|---|
| 1 | | | | 5 | | | | | 10 | | | | | 15 | |
| Pro | Thr | Ser | Pro | Leu | Thr | Ala | Glu | Arg | Leu | Glu | Thr | Glu | Glu | Asp | Val |
| | | | 20 | | | | | 25 | | | | | 30 | | |
| Ser | Gln | Ala | Phe | Leu | Glu | Ala | Val | Ala | Glu | Glu | Lys | Pro | His | Val | Lys |
| | | 35 | | | | | 40 | | | | | 45 | | | |
| Pro | Tyr | Phe | Ser | Lys | Thr | Ile | Arg | Asp | Leu | Glu | Val | Val | Glu | Gly | Ser |
| | 50 | | | | | 55 | | | | | | 60 | | | |
| Ala | Ala | Arg | Phe | Asp | Cys | Lys | Ile | Glu | Gly | Tyr | Pro | Asp | Pro | Glu | Val |
| 65 | | | | | 70 | | | | | 75 | | | | | 80 |
| Val | Trp | Phe | Lys | Asp | Asp | Gln | Ser | Ile | Arg | Glu | Ser | Arg | His | Phe | Gln |
| | | | | 85 | | | | | 90 | | | | | 95 | |
| Ile | Asp | Tyr | Asp | Glu | Asp | Gly | Asn | Cys | Ser | Leu | Ile | Ile | Ser | Asp | Val |
| | | | 100 | | | | | 105 | | | | | 110 | | |
| Cys | Gly | Asp | Asp | Asp | Ala | Lys | Tyr | Thr | Cys | Lys | Ala | Val | Asn | Ser | Leu |
| | | | 115 | | | | | 120 | | | | | 125 | | |
| Gly | Glu | Ala | Thr | Cys | Thr | Ala | Glu | Leu | Ile | Val | Glu | Thr | Met | Glu | Glu |
| | | | 130 | | | | | 135 | | | | | 140 | | |
| Gly | Glu | Gly | Glu | Gly | Glu | Glu | Glu | Glu | Glu |
| 145 | | | | | 150 | | | | 155 |

(2) INFORMATION FOR SEQ ID NO:8:

(i) SEQUENCE CHARACTERISTICS:
(A) LENGTH: 113 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:8:

| Met | Lys | Pro | Ser | Pro | Ser | Gln | Asp | Arg | Asp | Ser | Ser | Asp | Ser | Ser | Ser |
|---|---|---|---|---|---|---|---|---|---|---|---|---|---|---|---|
| 1 | | | | 5 | | | | | 10 | | | | | 15 | |
| Lys | Ala | Pro | Pro | Thr | Phe | Lys | Val | Ser | Leu | Met | Asp | Gln | Ser | Val | Arg |
| | | | 20 | | | | | 25 | | | | | 30 | | |
| Glu | Gly | Gln | Asp | Val | Ile | Met | Ser | Ile | Arg | Val | Gln | Gly | Glu | Pro | Lys |
| | | 35 | | | | | 40 | | | | | 45 | | | |
| Pro | Val | Val | Ser | Trp | Leu | Arg | Asn | Arg | Gln | Pro | Val | Arg | Pro | Asp | Gln |
| | 50 | | | | | 55 | | | | | | 60 | | | |
| Arg | Arg | Phe | Ala | Glu | Glu | Ala | Glu | Gly | Gly | Leu | Cys | Arg | Leu | Arg | Ile |
| 65 | | | | | 70 | | | | | 75 | | | | | 80 |
| Leu | Ala | Ala | Glu | Arg | Gly | Asp | Ala | Gly | Phe | Tyr | Thr | Cys | Lys | Ala | Val |
| | | | | 85 | | | | | 90 | | | | | 95 | |
| Asn | Glu | Tyr | Gly | Ala | Arg | Gln | Cys | Glu | Ala | Arg | Leu | Glu | Val | Arg | Gly |
| | | | 100 | | | | | 105 | | | | | 110 | | |
| Glu |

(2) INFORMATION FOR SEQ ID NO:9:

(i) SEQUENCE CHARACTERISTICS:
(A) LENGTH: 35 amino acids
(B) TYPE: amino acid
(C) STRANDEDNESS: Not Relevant
(D) TOPOLOGY: linear (ii) MOLECULE TYPE: protein ( x i ) SEQUENCE DESCRIPTION: SEQ ID NO:9:

```
Ser  Arg  Ser  Ser  Pro  Pro  Phe  Asp  Val  Glu  Gly  Gly  Pro  Pro  Val  Trp
 1              5                        10                      15

Gln  Glu  Gly  Cys  Leu  Ile  Asp  Tyr  Thr  Cys  Lys  Ala  Val  Asn  Gly  Cys
              20                        25                      30

Ala  Leu  Val
         35
```

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TTTTTTTTTT TTVG    14

( 2 ) INFORMATION FOR SEQ ID NO:11:

( i ) SEQUENCE CHARACTERISTICS:
        ( A ) LENGTH: 1238 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:11:

| | | | | | |
|---|---|---|---|---|---|
| TCACCTCTGA | TGAGGAATAC | CTGAGCCCCC | CAGAGGAGTT | CCCAGAGCCT | GGGGAGACCT | 60
| GGGGAGACCT | GGCCGCGAAC | CCCCACCATG | AAGCCCAGTC | CAGCCAGGA | CCGCCGTTCT | 120
| TCTGACACTG | GCTCCAAGGC | ACCCCCACC | TTCAAGGTCT | CACTTATGGA | CCAGTCAGTA | 180
| AGAGAAGGCC | AAGATGTCAT | CATGAGCATC | CGCGTGCAGG | GGGAGCCCAA | GCCTGTGGTC | 240
| TCCTGGCTGA | GAAACCGCCA | GCCCGTGCGC | CCAGACCAGC | GGCGCTTTGC | GGAGGAGGCT | 300
| GAGGGTGGGC | TGTGCCGGCT | GCGGATCCTG | GCTGCAGAGC | GTGGCGATGC | TGGTTTCTAC | 360
| ACTTGCAAAG | CGGTCAATGA | GTATGGTGCT | CGGCAGTGCG | AGGCCCGCTT | GGAGGTCCGA | 420
| GGCGAGTGAG | CTCAGGGGGC | CACCTGCGCT | CCCCCCGCTA | CCCTCCGAGC | CGCGCCCCTG | 480
| TCTCAGGCAC | CTCTCGGACC | TCGCTGTGTT | TCACTGCCTC | CTGCCCACAG | ACCCAGGCCT | 540
| GCCGGCCCGG | ACCCGTCCCA | GCCTCCCCTC | CCCACCCCAT | GCAGCCCCCA | GGGGGATAGC | 600
| CCATGGGCCC | CTGTGGACAC | TCCCTCCCCA | AGTGGACACA | TGGCTGTGCA | GGCCAGGAGG | 660
| CCCACAGATG | GACTGAGTGC | TGGGAAGGGG | CGGCTTCGAG | GGGTATCAAC | CCCCCGAGTC | 720
| TCTCCCTGAA | GGGGAGCACC | GGGCGAGTGC | ATGTGCTACT | GCTGCTACAG | GCCTGTCTAT | 780
| CTGTTTGTCT | GTCTGTGTGT | CTGTGACAGT | CAGGGAAGGA | TGCCTCGGAG | CTGAGGTGGG | 840
| GTGAGACAGA | GTGGGAGAGA | TTACGGCATG | GCATGGAGGG | GCCCAAGGAG | CAGGGCTGT | 900
| TGACAAAGGC | CTTACCAGGA | AGGGTTAGGA | CACTGACCAT | TCTAGAAATG | GGTTTCGAAT | 960
| GGCACAACAC | TTTCTATTTC | ACAAAAGACC | AAAAGCCAGA | GGCCCCAGGC | TCTGTGCTGA | 1020
| TGAACAGCCT | GGCTGAGCCC | TGGCCCTGGC | AGGTTTAGGG | CCCATTTGGG | GCCCCCTCCT | 1080
| TCTCTGTCAG | GGCTGGGGTG | CTCTGTCTGG | GAATGAGGGA | GTTAACCAAG | TTTGGTGCAG | 1140
| GAGCAGGGGC | AGGGGGCCAC | TGTAGTGAGC | GTGGATGAAA | TTTGGANACA | CCTATNTCTT | 1200

AANTCAAATA AAGTCCAGTT TGTACCTAAA AAAAAAAA 1238

( 2 ) INFORMATION FOR SEQ ID NO:12:

( i ) SEQUENCE CHARACTERISTICS:
        ( A ) LENGTH: 113 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:12:

```
Met Lys Pro Ser Pro Ser Gln Asp Arg Arg Ser Ser Asp Thr Gly Ser
 1               5                  10                  15

Lys Ala Pro Pro Thr Phe Lys Val Ser Leu Met Asp Gln Ser Val Arg
             20                  25                  30

Glu Gly Gln Asp Val Ile Met Ser Ile Arg Val Gln Gly Glu Pro Lys
             35                  40                  45

Pro Val Val Ser Trp Leu Arg Asn Arg Gln Pro Val Arg Pro Asp Gln
         50                  55                  60

Arg Arg Phe Ala Glu Glu Ala Glu Gly Gly Leu Cys Arg Leu Arg Ile
 65                  70                  75                  80

Leu Ala Ala Glu Arg Gly Asp Ala Gly Phe Tyr Thr Cys Lys Ala Val
                 85                  90                  95

Asn Glu Tyr Gly Ala Arg Gln Cys Glu Ala Arg Leu Glu Val Arg Gly
                100                 105                 110

Glu
```

( 2 ) INFORMATION FOR SEQ ID NO:13:

( i ) SEQUENCE CHARACTERISTICS:
        ( A ) LENGTH: 2793 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: Coding Sequence
        ( B ) LOCATION: 3...1983
        ( D ) OTHER INFORMATION:

( x i ) SEQUENCE DESCRIPTION: SEQ ID NO:13:

```
GA  ATT  CCG  GTC  CAA  ATC  CGC  GCT  GCT  CCC  CCC  ACC  GTC  CCC  TCG  GGT       47
    Ile  Pro  Val  Gln  Ile  Arg  Ala  Ala  Pro  Pro  Thr  Val  Pro  Ser  Gly
     1                    5                      10                     15

CGG  GAA  GCG  GTC  CCC  GCC  GGG  ACC  CCC  GGC  CCA  GCC  CGC  GGC  CAC  CCC       95
Arg  Glu  Ala  Val  Pro  Ala  Gly  Thr  Pro  Gly  Pro  Ala  Arg  Gly  His  Pro
                    20                      25                      30

CAC  GTC  GCC  CCA  CCG  TCG  CAC  TCA  GGA  GCC  TGT  GCT  GCC  CGA  GGA  CAC      143
His  Val  Ala  Pro  Pro  Ser  His  Ser  Gly  Ala  Cys  Ala  Ala  Arg  Gly  His
                         35                      40                      45

CAC  CAC  CGA  AGA  GAA  GCG  AGG  GAA  GAA  GTC  CAA  GTC  GTC  CGG  GCC  CTC      191
His  His  Arg  Arg  Glu  Ala  Arg  Glu  Glu  Val  Gln  Val  Val  Arg  Ala  Leu
               50                       55                      60

CCT  GGC  GGG  CAC  CGG  GAA  TCC  CGA  CCC  CAG  ACG  CCA  CTG  AGC  GAG  GCC      239
Pro  Gly  Gly  His  Arg  Glu  Ser  Arg  Pro  Gln  Thr  Pro  Leu  Ser  Glu  Ala
      65                       70                      75

TCA  GGC  CGC  CTG  TGG  GCG  TTG  GGC  CGA  TCG  CCT  AGG  CTG  GTG  CGC  GCC      287
Ser  Gly  Arg  Leu  Trp  Ala  Leu  Gly  Arg  Ser  Pro  Arg  Leu  Val  Arg  Ala
 80                       85                      90                      95
```

-continued

| | | | | | | | | | | | | | | | | |
|---|---|---|---|---|---|---|---|---|---|---|---|---|---|---|---|---|
| GGC | TCC | CGC | ATC | CTG | GAC | AAG | CTG | CAG | TTC | TTC | GAG | GAG | CGA | CGG | CGC | 335 |
| Gly | Ser | Arg | Ile | Leu | Asp | Lys | Leu | Gln | Phe | Phe | Glu | Glu | Arg | Arg | Arg | |
| | | | 100 | | | | | 105 | | | | | | 110 | | |
| AGC | CTG | GAG | CGC | AGC | GAC | TCG | CCG | CCG | GCG | CCC | CTG | CGG | CCC | TGG | GTG | 383 |
| Ser | Leu | Glu | Arg | Ser | Asp | Ser | Pro | Pro | Ala | Pro | Leu | Arg | Pro | Trp | Val | |
| | | | 115 | | | | | 120 | | | | | | 125 | | |
| CCC | CTG | CGC | AAG | GCC | CGC | TCT | CTG | GAG | CAG | CCC | AAG | TCG | GAG | CGC | GGC | 431 |
| Pro | Leu | Arg | Lys | Ala | Arg | Ser | Leu | Glu | Gln | Pro | Lys | Ser | Glu | Arg | Gly | |
| | | 130 | | | | | 135 | | | | | 140 | | | | |
| GCA | CCG | TGG | GGC | ACC | CCC | GGG | GCC | TCG | CAG | GAA | GAA | CTG | CGG | GCG | CCA | 479 |
| Ala | Pro | Trp | Gly | Thr | Pro | Gly | Ala | Ser | Gln | Glu | Glu | Leu | Arg | Ala | Pro | |
| | 145 | | | | | 150 | | | | | 155 | | | | | |
| GGC | AGC | GTG | GCC | GAG | CGG | CGC | CGC | CTG | TTC | CAG | CAG | AAA | GCG | GCC | TCG | 527 |
| Gly | Ser | Val | Ala | Glu | Arg | Arg | Arg | Leu | Phe | Gln | Gln | Lys | Ala | Ala | Ser | |
| 160 | | | | | 165 | | | | | 170 | | | | | 175 | |
| CTG | GAC | GAG | CGC | ACG | CGT | CAG | CGC | AGC | CCG | GCC | TCA | GAC | CTC | GAG | CTG | 575 |
| Leu | Asp | Glu | Arg | Thr | Arg | Gln | Arg | Ser | Pro | Ala | Ser | Asp | Leu | Glu | Leu | |
| | | | | 180 | | | | | 185 | | | | | 190 | | |
| CGC | TTC | GCC | CAG | GAG | CTG | GGC | CGC | ATC | CGC | CGC | TCC | ACG | TCG | CGG | GAG | 623 |
| Arg | Phe | Ala | Gln | Glu | Leu | Gly | Arg | Ile | Arg | Arg | Ser | Thr | Ser | Arg | Glu | |
| | | | 195 | | | | | 200 | | | | | 205 | | | |
| GAG | CTG | GTG | CGC | TCG | CAC | GAG | TCC | CTG | CGC | GCC | ACG | CTG | CAG | CGT | GCC | 671 |
| Glu | Leu | Val | Arg | Ser | His | Glu | Ser | Leu | Arg | Ala | Thr | Leu | Gln | Arg | Ala | |
| | | 210 | | | | | 215 | | | | | 220 | | | | |
| CCA | TCC | CCT | CGA | GAG | CCC | GGC | GAG | CCC | CCG | CTC | TTC | TCT | CGG | CCC | TCC | 719 |
| Pro | Ser | Pro | Arg | Glu | Pro | Gly | Glu | Pro | Pro | Leu | Phe | Ser | Arg | Pro | Ser | |
| | 225 | | | | | 230 | | | | | 235 | | | | | |
| ACC | CCC | AAG | ACA | TCG | CGG | GCC | GTG | AGC | CCC | GCC | GCC | GCC | CAG | CCG | CCC | 767 |
| Thr | Pro | Lys | Thr | Ser | Arg | Ala | Val | Ser | Pro | Ala | Ala | Ala | Gln | Pro | Pro | |
| 240 | | | | | 245 | | | | | 250 | | | | | 255 | |
| TCT | CCG | AGC | AGC | GCG | GAG | AAG | CCG | GGG | GAC | GAG | CCT | GGG | AGG | CCC | AGG | 815 |
| Ser | Pro | Ser | Ser | Ala | Glu | Lys | Pro | Gly | Asp | Glu | Pro | Gly | Arg | Pro | Arg | |
| | | | | 260 | | | | | 265 | | | | | 270 | | |
| AGC | CGC | GGG | CCG | GCG | GGC | AGG | ACA | GAG | CCG | GGG | GAA | GGC | CCG | CAG | CAG | 863 |
| Ser | Arg | Gly | Pro | Ala | Gly | Arg | Thr | Glu | Pro | Gly | Glu | Gly | Pro | Gln | Gln | |
| | | | 275 | | | | | 280 | | | | | 285 | | | |
| GAG | GTT | AGG | CGT | CGG | GAC | CAA | TTC | CCG | CTG | ACC | CGG | AGC | AGA | GCC | ATC | 911 |
| Glu | Val | Arg | Arg | Arg | Asp | Gln | Phe | Pro | Leu | Thr | Arg | Ser | Arg | Ala | Ile | |
| | | 290 | | | | | 295 | | | | | 300 | | | | |
| CAG | GAG | TGC | AGG | AGC | CCT | GTG | CCG | CCC | CCC | GCC | GCC | GAT | CCC | CCA | GAG | 959 |
| Gln | Glu | Cys | Arg | Ser | Pro | Val | Pro | Pro | Pro | Ala | Ala | Asp | Pro | Pro | Glu | |
| | 305 | | | | | 310 | | | | | 315 | | | | | |
| GCC | AGG | ACG | AAA | GCA | CCC | CCC | GGT | CGG | AAG | CGG | GAG | CCC | CCG | GCG | CAG | 1007 |
| Ala | Arg | Thr | Lys | Ala | Pro | Pro | Gly | Arg | Lys | Arg | Glu | Pro | Pro | Ala | Gln | |
| 320 | | | | | 325 | | | | | 330 | | | | | 335 | |
| GCC | GTG | CGC | TTC | CTG | CCC | TGG | GCC | ACG | CCG | GGC | CTG | GAG | GGC | GCT | GCT | 1055 |
| Ala | Val | Arg | Phe | Leu | Pro | Trp | Ala | Thr | Pro | Gly | Leu | Glu | Gly | Ala | Ala | |
| | | | | 340 | | | | | 345 | | | | | 350 | | |
| GTA | CCC | CAG | ACC | TTG | GAG | AAG | AAC | AGG | GCG | GGG | CCT | GAG | GCA | GAG | AAG | 1103 |
| Val | Pro | Gln | Thr | Leu | Glu | Lys | Asn | Arg | Ala | Gly | Pro | Glu | Ala | Glu | Lys | |
| | | | 355 | | | | | 360 | | | | | 365 | | | |
| AGG | CTT | CGC | AGA | GGG | CCG | GAG | GAG | GAC | GGT | CCC | TGG | GGG | CCC | TGG | GAC | 1151 |
| Arg | Leu | Arg | Arg | Gly | Pro | Glu | Glu | Asp | Gly | Pro | Trp | Gly | Pro | Trp | Asp | |
| | | 370 | | | | | 375 | | | | | 380 | | | | |
| CGC | CGA | GGG | GCC | CGC | AGC | CAG | GGC | AAA | GGT | CGC | CGG | GCC | CGG | CCC | ACC | 1199 |
| Arg | Arg | Gly | Ala | Arg | Ser | Gln | Gly | Lys | Gly | Arg | Arg | Ala | Arg | Pro | Thr | |
| | 385 | | | | | 390 | | | | | 395 | | | | | |
| TCC | CCT | GAG | CTC | GAG | TCT | TCG | GAT | GAC | TCC | TAC | GTG | TCC | GCT | GGA | GAA | 1247 |
| Ser | Pro | Glu | Leu | Glu | Ser | Ser | Asp | Asp | Ser | Tyr | Val | Ser | Ala | Gly | Glu | |
| 400 | | | | | 405 | | | | | 410 | | | | | 415 | |

| | | | | | | | | | | | | | | | |
|---|---|---|---|---|---|---|---|---|---|---|---|---|---|---|---|
| GAG | CCC | CTA | GAG | GCC | CCT | GTG | TTT | GAG | ATC | CCC | CTG | CAG | AAT | GTG | GTG | 1295
| Glu | Pro | Leu | Glu | Ala | Pro | Val | Phe | Glu | Ile | Pro | Leu | Gln | Asn | Val | Val |
|  |  |  |  | 420 |  |  |  | 425 |  |  |  |  |  | 430 |  |
| GTG | GCA | CCA | GGG | GCA | GAT | GTG | CTG | CTC | AAA | TGT | ATC | ATC | ACT | GCC | AAC | 1343
| Val | Ala | Pro | Gly | Ala | Asp | Val | Leu | Leu | Lys | Cys | Ile | Ile | Thr | Ala | Asn |
|  |  |  | 435 |  |  |  |  | 440 |  |  |  |  | 445 |  |  |
| CCC | CCG | CCC | CAA | GTG | TCC | TGG | CAC | AAG | GAT | GGG | TCA | GCG | CTG | CGC | AGC | 1391
| Pro | Pro | Pro | Gln | Val | Ser | Trp | His | Lys | Asp | Gly | Ser | Ala | Leu | Arg | Ser |
|  |  | 450 |  |  |  |  | 455 |  |  |  |  | 460 |  |  |  |
| GAG | GGC | CGC | CTC | CTC | CTC | CGG | GCT | GAG | GGT | GAG | CGG | CAC | ACC | CTG | CTG | 1439
| Glu | Gly | Arg | Leu | Leu | Leu | Arg | Ala | Glu | Gly | Glu | Arg | His | Thr | Leu | Leu |
|  | 465 |  |  |  |  | 470 |  |  |  |  | 475 |  |  |  |  |
| CTC | AGG | GAG | GCC | AGG | GCA | GCA | GAT | GCC | GGG | AGC | TAT | ATG | GCC | ACC | GCC | 1487
| Leu | Arg | Glu | Ala | Arg | Ala | Ala | Asp | Ala | Gly | Ser | Tyr | Met | Ala | Thr | Ala |
| 480 |  |  |  |  | 485 |  |  |  |  | 490 |  |  |  |  | 495 |
| ACC | AAC | GAG | CTG | GGC | CAG | GCC | ACC | TGT | GCC | GCC | TCA | CTG | ACC | GTG | AGA | 1535
| Thr | Asn | Glu | Leu | Gly | Gln | Ala | Thr | Cys | Ala | Ala | Ser | Leu | Thr | Val | Arg |
|  |  |  |  | 500 |  |  |  | 505 |  |  |  |  | 510 |  |  |
| CCC | GGT | GGG | TCT | ACA | TCC | CCT | TTC | AGC | AGC | CCC | ATC | ACC | TCC | GAC | GAG | 1583
| Pro | Gly | Gly | Ser | Thr | Ser | Pro | Phe | Ser | Ser | Pro | Ile | Thr | Ser | Asp | Glu |
|  |  |  | 515 |  |  |  | 520 |  |  |  |  | 525 |  |  |  |
| GAA | TAC | CTG | AGC | CCC | CCA | GAG | GAG | TTC | CCA | GAG | CCT | GGG | GAG | ACC | TGG | 1631
| Glu | Tyr | Leu | Ser | Pro | Pro | Glu | Glu | Phe | Pro | Glu | Pro | Gly | Glu | Thr | Trp |
|  |  | 530 |  |  |  | 535 |  |  |  |  | 540 |  |  |  |  |
| CCG | CGA | ACC | CCC | ACC | ATG | AAG | CCC | AGT | CCC | AGC | CAG | AAC | CGC | CGT | TCT | 1679
| Pro | Arg | Thr | Pro | Thr | Met | Lys | Pro | Ser | Pro | Ser | Gln | Asn | Arg | Arg | Ser |
|  | 545 |  |  |  |  | 550 |  |  |  |  | 555 |  |  |  |  |
| TCT | GAC | ACT | GGC | TCC | AAG | GCA | CCC | CCC | ACC | TTC | AAG | GTC | TCA | CTT | ATG | 1727
| Ser | Asp | Thr | Gly | Ser | Lys | Ala | Pro | Pro | Thr | Phe | Lys | Val | Ser | Leu | Met |
| 560 |  |  |  |  | 565 |  |  |  |  | 570 |  |  |  |  | 575 |
| GAC | CAG | TCA | GTA | AGA | GAA | GGC | CAA | GAT | GTC | ATC | ATG | AGC | ATC | CGC | GTG | 1775
| Asp | Gln | Ser | Val | Arg | Glu | Gly | Gln | Asp | Val | Ile | Met | Ser | Ile | Arg | Val |
|  |  |  |  | 580 |  |  |  | 585 |  |  |  |  | 590 |  |  |
| CAG | GGG | GAG | CCC | AAG | CCT | GTG | GTC | TCC | TGG | CTG | AGA | AAC | CGC | CAG | CCC | 1823
| Gln | Gly | Glu | Pro | Lys | Pro | Val | Val | Ser | Trp | Leu | Arg | Asn | Arg | Gln | Pro |
|  |  |  | 595 |  |  |  |  | 600 |  |  |  |  | 605 |  |  |
| GTG | CGC | CCA | GAC | CAG | CGG | CGC | TTT | GCG | GAG | GAG | GCT | GAG | GGT | GGG | CTG | 1871
| Val | Arg | Pro | Asp | Gln | Arg | Arg | Phe | Ala | Glu | Glu | Ala | Glu | Gly | Gly | Leu |
|  |  | 610 |  |  |  |  | 615 |  |  |  |  | 620 |  |  |  |
| TGC | CGG | CTG | CGG | ATC | CTG | GCT | GCA | GAG | CGT | GGC | GAT | GCT | GGT | TTC | TAC | 1919
| Cys | Arg | Leu | Arg | Ile | Leu | Ala | Ala | Glu | Arg | Gly | Asp | Ala | Gly | Phe | Tyr |
|  | 625 |  |  |  |  | 630 |  |  |  |  | 635 |  |  |  |  |
| ACT | TGC | AAA | GCG | GTC | AAT | GAG | TAT | GGT | GCT | CGG | CAG | TGC | GAG | GCC | CGC | 1967
| Thr | Cys | Lys | Ala | Val | Asn | Glu | Tyr | Gly | Ala | Arg | Gln | Cys | Glu | Ala | Arg |
| 640 |  |  |  |  | 645 |  |  |  |  | 650 |  |  |  |  | 655 |
| TTG | GAG | GTC | CGA | GGC | G | AGTGAGCTCA | GGGGGCCACC | TGCGCTCCCC | CCGCTACCCT | | | | | | | 2023
| Leu | Glu | Val | Arg | Gly | Glu |
|  |  |  |  | 660 |  |

| | | | | |
|---|---|---|---|---|
| CCGAGCCGCG | CCCCTGTCTC | AGGCACCTCT | CGGACCTCGC | TGTGTTTCAC | TGCCTCCTGC | 2083
| CCACAGACCC | AGCTGCCGGC | CCGGACCCGT | CCAGCCTCC | CCTCCCCACC | CCATGCAGCC | 2143
| CCCAGGGGGA | TAGCCCATGG | GCCCCTGTGG | ACCCTCCCTC | CCAAGTGGA | CACATGGCTG | 2203
| TGCAGCCAGG | AGGCCCACAG | ATGGACTGAG | TGCTGGGAAG | GGGCGGCTGC | GAGGGGTATC | 2263
| AACCCCCCGA | GTCTCTCCCT | GAAGGGGAGC | ACCGGGCGAG | TGCATGTGCT | ACTGCTGCTA | 2323
| CAGGCCTGTC | TATCTGTTTG | TCTGTCTGTG | TGTCTGTGAC | AGTCAGGGAA | GGATGCCTCG | 2383
| GAGCTGAGGT | GGGGTGAGAC | AGAGTGGGAG | AGATTACGGC | ATGGCATGGA | GGGGCCCAAG | 2443
| GAGCAGGGGC | TGTTGACAAA | GGCCTTACCA | GGAAGGGTTA | GGACACTGAC | CATTCTAGAA | 2503

```
ATGGGTTTCG  AATGGCACAA  CACTTTCTAT  TTCACAAAAG  ACCAAAAGCC  AGAGGCCCCA    2563

GGCTCTGTGC  TGATGAACAG  CCTGGCTGAG  CCCTGGCCCT  GGCAGGTTTA  GGGCCCATTT    2623

GGGGCCCCCT  CCTTCTCTGT  CAGGGCTGGG  GTGCTCTGTC  TGGGAATGAG  GGAGTTAACC    2683

AAGTTTGGTG  CAGGAGCAGG  GGCAGGGGGC  CACTGTAGTG  AGCGTGGAGA  AATTTGGAAA    2743

CACCTATTTC  TTAACTCAAA  TAAAGTCCAG  TTTGTACCTA  AAAAAAAAA                 2793
```

( 2 ) INFORMATION FOR SEQ ID NO:14:

( i ) SEQUENCE CHARACTERISTICS:
( A ) LENGTH: 661 amino acids
( B ) TYPE: amino acid
( C ) STRANDEDNESS: Not Relevant
( D ) TOPOLOGY: linear ( i i ) MOLECULE TYPE: protein ( v ) FRAGMENT TYPE: internal ( x i ) SEQUENCE DESCRIPTION: SEQ ID NO:14:

```
Ile  Pro  Val  Gln  Ile  Arg  Ala  Ala  Pro  Pro  Thr  Val  Pro  Ser  Gly  Arg
 1              5                        10                       15

Glu  Ala  Val  Pro  Ala  Gly  Thr  Pro  Gly  Pro  Ala  Arg  Gly  His  Pro  His
              20                        25                       30

Val  Ala  Pro  Pro  Ser  His  Ser  Gly  Ala  Cys  Ala  Ala  Arg  Gly  His  His
         35                        40                       45

His  Arg  Arg  Glu  Ala  Arg  Glu  Glu  Val  Gln  Val  Val  Arg  Ala  Leu  Pro
     50                        55                       60

Gly  Gly  His  Arg  Glu  Ser  Arg  Pro  Gln  Thr  Pro  Leu  Ser  Glu  Ala  Ser
65                       70                       75                        80

Gly  Arg  Leu  Trp  Ala  Leu  Gly  Arg  Ser  Pro  Arg  Leu  Val  Arg  Ala  Gly
                    85                        90                       95

Ser  Arg  Ile  Leu  Asp  Lys  Leu  Gln  Phe  Phe  Glu  Glu  Arg  Arg  Arg  Ser
               100                       105                      110

Leu  Glu  Arg  Ser  Asp  Ser  Pro  Pro  Ala  Pro  Leu  Arg  Pro  Trp  Val  Pro
          115                       120                      125

Leu  Arg  Lys  Ala  Arg  Ser  Leu  Glu  Gln  Pro  Lys  Ser  Glu  Arg  Gly  Ala
     130                       135                      140

Pro  Trp  Gly  Thr  Pro  Gly  Ala  Ser  Gln  Glu  Glu  Leu  Arg  Ala  Pro  Gly
145                      150                       155                      160

Ser  Val  Ala  Glu  Arg  Arg  Arg  Leu  Phe  Gln  Gln  Lys  Ala  Ala  Ser  Leu
                    165                       170                      175

Asp  Glu  Arg  Thr  Arg  Gln  Arg  Ser  Pro  Ala  Ser  Asp  Leu  Glu  Leu  Arg
               180                       185                      190

Phe  Ala  Gln  Glu  Leu  Gly  Arg  Ile  Arg  Arg  Ser  Thr  Ser  Arg  Glu  Glu
          195                       200                      205

Leu  Val  Arg  Ser  His  Glu  Ser  Leu  Arg  Ala  Thr  Leu  Gln  Arg  Ala  Pro
     210                       215                      220

Ser  Pro  Arg  Glu  Pro  Gly  Glu  Pro  Pro  Leu  Phe  Ser  Arg  Pro  Ser  Thr
225                      230                       235                      240

Pro  Lys  Thr  Ser  Arg  Ala  Val  Ser  Pro  Ala  Ala  Ala  Gln  Pro  Pro  Ser
                    245                       250                      255

Pro  Ser  Ser  Ala  Glu  Lys  Pro  Gly  Asp  Glu  Pro  Gly  Arg  Pro  Arg  Ser
               260                       265                      270

Arg  Gly  Pro  Ala  Gly  Arg  Thr  Glu  Pro  Gly  Glu  Gly  Pro  Gln  Gln  Glu
          275                       280                      285

Val  Arg  Arg  Arg  Asp  Gln  Phe  Pro  Leu  Thr  Arg  Ser  Arg  Ala  Ile  Gln
```

|     |     |     | 290 |     |     | 295 |     |     | 300 |     |     |     |
|---|---|---|---|---|---|---|---|---|---|---|---|---|

Glu Cys Arg Ser Pro Val Pro Pro Pro Ala Ala Asp Pro Pro Glu Ala
305                     310                     315                     320

Arg Thr Lys Ala Pro Pro Gly Arg Lys Arg Glu Pro Pro Ala Gln Ala
                        325                     330                     335

Val Arg Phe Leu Pro Trp Ala Thr Pro Gly Leu Glu Gly Ala Ala Val
                340                     345                     350

Pro Gln Thr Leu Glu Lys Asn Arg Ala Gly Pro Glu Ala Glu Lys Arg
            355                     360                     365

Leu Arg Arg Gly Pro Glu Glu Asp Gly Pro Trp Gly Pro Trp Asp Arg
370                     375                     380

Arg Gly Ala Arg Ser Gln Gly Lys Gly Arg Arg Ala Arg Pro Thr Ser
385                     390                     395                     400

Pro Glu Leu Glu Ser Ser Asp Asp Ser Tyr Val Ser Ala Gly Glu Glu
                405                     410                     415

Pro Leu Glu Ala Pro Val Phe Glu Ile Pro Leu Gln Asn Val Val
                420                     425                     430

Ala Pro Gly Ala Asp Val Leu Leu Lys Cys Ile Ile Thr Ala Asn Pro
                435                     440                     445

Pro Pro Gln Val Ser Trp His Lys Asp Gly Ser Ala Leu Arg Ser Glu
    450                     455                     460

Gly Arg Leu Leu Leu Arg Ala Glu Gly Glu Arg His Thr Leu Leu Leu
465                     470                     475                     480

Arg Glu Ala Arg Ala Ala Asp Ala Gly Ser Tyr Met Ala Thr Ala Thr
                485                     490                     495

Asn Glu Leu Gly Gln Ala Thr Cys Ala Ala Ser Leu Thr Val Arg Pro
            500                     505                     510

Gly Gly Ser Thr Ser Pro Phe Ser Ser Pro Ile Thr Ser Asp Glu Glu
            515                     520                     525

Tyr Leu Ser Pro Pro Glu Glu Phe Pro Glu Pro Gly Glu Thr Trp Pro
        530                     535                     540

Arg Thr Pro Thr Met Lys Pro Ser Pro Ser Gln Asn Arg Arg Ser Ser
545                     550                     555                     560

Asp Thr Gly Ser Lys Ala Pro Pro Thr Phe Lys Val Ser Leu Met Asp
                565                     570                     575

Gln Ser Val Arg Glu Gly Gln Asp Val Ile Met Ser Ile Arg Val Gln
            580                     585                     590

Gly Glu Pro Lys Pro Val Val Ser Trp Leu Arg Asn Arg Gln Pro Val
        595                     600                     605

Arg Pro Asp Gln Arg Arg Phe Ala Glu Glu Ala Glu Gly Gly Leu Cys
610                     615                     620

Arg Leu Arg Ile Leu Ala Ala Glu Arg Gly Asp Ala Gly Phe Tyr Thr
625                     630                     635                     640

Cys Lys Ala Val Asn Glu Tyr Gly Ala Arg Gln Cys Glu Ala Arg Leu
                645                     650                     655

Glu Val Arg Gly Glu
                660

( 2 ) INFORMATION FOR SEQ ID NO:15:

( i ) SEQUENCE CHARACTERISTICS:
        ( A ) LENGTH: 2614 base pairs
        ( B ) TYPE: nucleic acid
        ( C ) STRANDEDNESS: double
        ( D ) TOPOLOGY: linear (i i) MOLECULE TYPE: DNA (i x) FEATURE:
    (A) NAME/KEY: Coding Sequence
    (B) LOCATION: 1...1803
    (D) OTHER INFORMATION:

(x i) SEQUENCE DESCRIPTION: SEQ ID NO:15:

```
GAA  TTC  CGG  CTG  GCG  GGC  ACA  GTG  GAG  TCC  CGG  CCC  CAG  ACG  CCA  CTG     48
Glu  Phe  Arg  Leu  Ala  Gly  Thr  Val  Glu  Ser  Arg  Pro  Gln  Thr  Pro  Leu
 1              5                        10                       15

AGC  GAG  GCT  TCG  GGT  CGC  CTG  TCA  GCA  CTG  GGC  CGC  TCG  CCC  CGG  CTG     96
Ser  Glu  Ala  Ser  Gly  Arg  Leu  Ser  Ala  Leu  Gly  Arg  Ser  Pro  Arg  Leu
               20                       25                       30

GTG  CGC  GCG  GGG  TCC  CGC  ATC  CTG  GAC  AAG  CTA  CAG  TTC  TTC  GAA  GAG    144
Val  Arg  Ala  Gly  Ser  Arg  Ile  Leu  Asp  Lys  Leu  Gln  Phe  Phe  Glu  Glu
                    35                   40                       45

CGG  CGA  CGC  AGC  CTG  GAG  CGC  AGC  GAC  TCG  CCG  CCA  GCG  CCC  CTG  CGG    192
Arg  Arg  Arg  Ser  Leu  Glu  Arg  Ser  Asp  Ser  Pro  Pro  Ala  Pro  Leu  Arg
     50                        55                        60

CCC  TGG  GTG  CCC  CTG  CGC  AAG  GCT  CGC  TCG  CTG  GAG  CAG  CCG  AAG  TCC    240
Pro  Trp  Val  Pro  Leu  Arg  Lys  Ala  Arg  Ser  Leu  Glu  Gln  Pro  Lys  Ser
 65                       70                        75                       80

GAG  GGC  GGT  GCG  GCG  TGG  GGC  ACA  CCC  GAG  GCC  TCG  CAG  GAG  GAG  CTG    288
Glu  Gly  Gly  Ala  Ala  Trp  Gly  Thr  Pro  Glu  Ala  Ser  Gln  Glu  Glu  Leu
                         85                        90                       95

CGG  TCA  CCT  CGG  GGC  AGT  GTG  GCA  GAG  CGG  CGT  CGC  CTG  TTC  CAG  CAA    336
Arg  Ser  Pro  Arg  Gly  Ser  Val  Ala  Glu  Arg  Arg  Arg  Leu  Phe  Gln  Gln
                    100                  105                      110

AAG  GCG  GCC  TCG  TTG  GAT  GAA  CGC  ACG  CGA  CAA  CGC  AGT  GCA  ACC  TCG    384
Lys  Ala  Ala  Ser  Leu  Asp  Glu  Arg  Thr  Arg  Gln  Arg  Ser  Ala  Thr  Ser
               115                       120                      125

GAC  CTC  GAA  CTC  CGC  TTC  GCC  CAG  GAG  CTG  GGT  CGC  ATC  CGC  CGA  TCT    432
Asp  Leu  Glu  Leu  Arg  Phe  Ala  Gln  Glu  Leu  Gly  Arg  Ile  Arg  Arg  Ser
     130                      135                       140

ACG  TCG  CGG  GAG  GAG  CTG  GTG  CGT  TCG  CAC  GAG  TCC  CTG  CGT  GCC  ACG    480
Thr  Ser  Arg  Glu  Glu  Leu  Val  Arg  Ser  His  Glu  Ser  Leu  Arg  Ala  Thr
145                       150                       155                      160

CTG  CAG  CGC  GCC  CCA  TCC  CCT  CGG  GAG  CCC  GGC  GAG  CCC  CCA  CTC  TTC    528
Leu  Gln  Arg  Ala  Pro  Ser  Pro  Arg  Glu  Pro  Gly  Glu  Pro  Pro  Leu  Phe
                    165                       170                      175

TCC  CGG  CCT  TCC  ACA  CCC  AAG  ACC  TCA  CGG  GCT  GTG  AGC  CCG  GCT  GCC    576
Ser  Arg  Pro  Ser  Thr  Pro  Lys  Thr  Ser  Arg  Ala  Val  Ser  Pro  Ala  Ala
               180                       185                      190

ACC  CAG  CCG  CCG  CCT  CCT  AGT  GGT  GCG  GGC  AAA  TCT  GGG  GAC  GAG  CCT    624
Thr  Gln  Pro  Pro  Pro  Pro  Ser  Gly  Ala  Gly  Lys  Ser  Gly  Asp  Glu  Pro
          195                       200                       205

GGG  AGG  CCC  CGA  AGC  AGA  GGG  CCG  GTG  GGC  AGG  ACT  GAA  CCG  GGG  GAA    672
Gly  Arg  Pro  Arg  Ser  Arg  Gly  Pro  Val  Gly  Arg  Thr  Glu  Pro  Gly  Glu
     210                      215                       220

GGC  CCG  CAG  CAG  GAG  ATC  AAG  CGT  CGG  GAC  CAA  TTC  CCG  CTA  ACC  AGG    720
Gly  Pro  Gln  Gln  Glu  Ile  Lys  Arg  Arg  Asp  Gln  Phe  Pro  Leu  Thr  Arg
225                       230                       235                      240

AGC  AGA  GCC  ATC  CAG  GAG  TGC  AGG  AGC  CCT  GTG  CCG  CCC  TAC  ACC  GCG    768
Ser  Arg  Ala  Ile  Gln  Glu  Cys  Arg  Ser  Pro  Val  Pro  Pro  Tyr  Thr  Ala
                    245                       250                      255

GAT  CCC  CCG  GAG  AGC  AGG  ACA  AAA  GCC  CCC  TCC  GGT  CGC  AAG  CGG  GAA    816
Asp  Pro  Pro  Glu  Ser  Arg  Thr  Lys  Ala  Pro  Ser  Gly  Arg  Lys  Arg  Glu
               260                       265                      270

CCC  CCT  GCT  CAA  GCG  GTG  CGC  TTT  CTG  CCC  TGG  GCC  ACT  CCG  GGA  GTG    864
Pro  Pro  Ala  Gln  Ala  Val  Arg  Phe  Leu  Pro  Trp  Ala  Thr  Pro  Gly  Val
          275                       280                       285
```

```
GAG GAC TCT GTT CTG CCC CAA ACC TTG GAG AAG AAT AGA GCG GGA CCC         912
Glu Asp Ser Val Leu Pro Gln Thr Leu Glu Lys Asn Arg Ala Gly Pro
        290                 295                 300

GAG GCT GAG AAG AGG CTT CGC AGA GGA CCT GAG GAG GAT GGC CCC TGG         960
Glu Ala Glu Lys Arg Leu Arg Arg Gly Pro Glu Glu Asp Gly Pro Trp
305                 310                 315                 320

GGG CCC TGG GAC CGC AGA GGG ACC CGC AGC CAA GGC AAA GGT CGC CGT        1008
Gly Pro Trp Asp Arg Arg Gly Thr Arg Ser Gln Gly Lys Gly Arg Arg
                    325                 330                 335

GCT CGG CCT ACT TCC CCC GAG CTC GAG TCC TCA GAC GAC TCC TAT GTG        1056
Ala Arg Pro Thr Ser Pro Glu Leu Glu Ser Ser Asp Asp Ser Tyr Val
                340                 345                 350

TCC GCT GGG GAA GAG CCC CTG GAG GCA CCC GTG TTT GAG ATC CCT CTG        1104
Ser Ala Gly Glu Glu Pro Leu Glu Ala Pro Val Phe Glu Ile Pro Leu
            355                 360                 365

CAG AAT ATG GTG GTG GCG CCA GGA GCT GAC GTG CTA CTT AAG TGT ATC        1152
Gln Asn Met Val Val Ala Pro Gly Ala Asp Val Leu Leu Lys Cys Ile
        370                 375                 380

ATC ACC GCC AAC CCC CCA CCC CAA GTG TCC TGG AAA AAG GAT GGG TCC        1200
Ile Thr Ala Asn Pro Pro Pro Gln Val Ser Trp Lys Lys Asp Gly Ser
385                 390                 395                 400

ATG TTG CAC AGC GAG GGT CGT CTT CTC ATC CGG GCT GAA GGT GAA CGG        1248
Met Leu His Ser Glu Gly Arg Leu Leu Ile Arg Ala Glu Gly Glu Arg
                    405                 410                 415

CAC ACA CTG CTG CTC AGA GAG GCC CAG GCT GCT GAT GCT GGG AGC TAC        1296
His Thr Leu Leu Leu Arg Glu Ala Gln Ala Ala Asp Ala Gly Ser Tyr
                420                 425                 430

ACA GCC ACT GCC ACC AAC GAA CTG GGC CAA GCT ACC TGT GCT TCT TCA        1344
Thr Ala Thr Ala Thr Asn Glu Leu Gly Gln Ala Thr Cys Ala Ser Ser
            435                 440                 445

CTG GCT GTG AGA CCT GGC GGC TCC ACA TCC CCT TTC AGC AGC CCC ATC        1392
Leu Ala Val Arg Pro Gly Gly Ser Thr Ser Pro Phe Ser Ser Pro Ile
450                 455                 460

ACC TCT GAT GAG GAG TAC CTG AGC CCC CCA GAG GAG TTC CCA GAG CCT        1440
Thr Ser Asp Glu Glu Tyr Leu Ser Pro Pro Glu Glu Phe Pro Glu Pro
465                 470                 475                 480

GGG GAG ACC TGG CCC CGA ACC CCT ACC ATG AAG CTC AGT CCC AGC CAG        1488
Gly Glu Thr Trp Pro Arg Thr Pro Thr Met Lys Leu Ser Pro Ser Gln
                    485                 490                 495

GAT CAT GAT TCC TCC GAC TCT TCT TCC AAG GCA CCC CCA ACG TTC AAG        1536
Asp His Asp Ser Ser Asp Ser Ser Ser Lys Ala Pro Pro Thr Phe Lys
                500                 505                 510

GTC TCA CTC ATG GAC CAA TCG GTG AGA GAA GGT CAA GAT GTC ATT ATG        1584
Val Ser Leu Met Asp Gln Ser Val Arg Glu Gly Gln Asp Val Ile Met
            515                 520                 525

AGC ATC CGT GTG CAG GGA GAG CCC AAG CCT GTG GTT TCC TGG CTG AGG        1632
Ser Ile Arg Val Gln Gly Glu Pro Lys Pro Val Val Ser Trp Leu Arg
530                 535                 540

AAT CGA CAG CCC GTG CGC CCA GAC CAG CGG CGC TTT GCA GAG GAG GCC        1680
Asn Arg Gln Pro Val Arg Pro Asp Gln Arg Arg Phe Ala Glu Glu Ala
545                 550                 555                 560

GAG GGT GGG CTC TGC CGC TTG AGG ATC CTG GCT GCT GAA CGG GGC GAT        1728
Glu Gly Gly Leu Cys Arg Leu Arg Ile Leu Ala Ala Glu Arg Gly Asp
                    565                 570                 575

GCT GGT TTC TAC ACA TGC AAG GCG GTC AAC GAA TAT GGC GCT CGG CAG        1776
Ala Gly Phe Tyr Thr Cys Lys Ala Val Asn Glu Tyr Gly Ala Arg Gln
                580                 585                 590

TGC GAG GCC CGC CTG GAG GTC CGA GGC GAGTGAGCTC AGGGGGCCAC CTGCGCT      1830
Cys Glu Ala Arg Leu Glu Val Arg Gly
            595                 600
```

```
GCCCCCGCTA  CCCTCCGAGC  TGCACCCCTG  TCTCAGGCAC  CTCTCGGACC  TCGCTGTGTT   1890

TCACTGCCTC  CTGCCCACAG  ACCCAGCCGG  CTCGCCGGCC  CGGACTTAGC  CCATGCTCCC   1950

CTTCCCTCCC  TAGCCCATAC  AGCACCCTGG  GGTAACCCAC  CGGGCCCCTG  TGGATCCTCC   2010

CTCCCCAAGT  GGATATGTGG  CTGTGCAGAC  CAGGAGGCCC  CCAGAAGGAC  TGAGTGTTGG   2070

GAAGGGATGG  CCATGAGGGG  TGCCAAGCTC  CCTCGGTCTC  CCCATAGGGA  GCATCCAGCG   2130

AGTGCATGTG  CTATGCTGCT  ACAGGCCACT  GTCTGTCTAT  CTGTTTGTCC  GTCTGTGTGT   2190

CTGTGACAGT  CAGGGAAGAA  AGCCTTTGAG  CTGAGGTGGG  CTAAGACAGA  ATAAGATGAC   2250

AGAGCACAGC  ATCCATGAGA  TGCAGGGGTT  CAGAGGGGTC  AGGTACAGTG  GATATGAGGC   2310

TCTCTGGGAA  GGGGCAGGGC  ACTGACCATT  TCAGAAATGG  GTTTTAAATG  GCACAACATT   2370

TTTTATTCCA  CAAGAGACCA  AAAGCTAGAG  GTCTAGGGTT  AAGCCCTAGC  TGCTGGCAAG   2430

ATTAGGACCA  AGTGGGGTAC  CCTTCTTTAC  AGACACATCC  GACACGCGCT  GTCTGAGAAT   2490

GAGAGAGGTA  GCCAGGCTGA  ACACAGGAGC  AGGGTCATAG  TGGAGGTGGA  GATTTGGAAA   2550

CACTATTTCG  TAGCTCAAAT  AAAGTCCAGT  TTGTACCCAA  AAAAAAAAA  AAAAAAAAA   2610

AAAA                                                                    2614
```

( 2 ) INFORMATION FOR SEQ ID NO:16:

( i ) SEQUENCE CHARACTERISTICS:
        ( A ) LENGTH: 601 amino acids
        ( B ) TYPE: amino acid
        ( C ) STRANDEDNESS: Not Relevant
        ( D ) TOPOLOGY: linear ( i i ) MOLECULE TYPE: protein ( v ) FRAGMENT TYPE: internal ( x i ) SEQUENCE DESCRIPTION: SEQ ID NO:16:

```
Glu  Phe  Arg  Leu  Ala  Gly  Thr  Val  Glu  Ser  Arg  Pro  Gln  Thr  Pro  Leu
 1              5                    10                       15

Ser  Glu  Ala  Ser  Gly  Arg  Leu  Ser  Ala  Leu  Gly  Arg  Ser  Pro  Arg  Leu
                20                       25                       30

Val  Arg  Ala  Gly  Ser  Arg  Ile  Leu  Asp  Lys  Leu  Gln  Phe  Phe  Glu  Glu
               35                   40                       45

Arg  Arg  Arg  Ser  Leu  Glu  Arg  Ser  Asp  Ser  Pro  Pro  Ala  Pro  Leu  Arg
     50                        55                      60

Pro  Trp  Val  Pro  Leu  Arg  Lys  Ala  Arg  Ser  Leu  Glu  Gln  Pro  Lys  Ser
65                        70                       75                       80

Glu  Gly  Gly  Ala  Ala  Trp  Gly  Thr  Pro  Glu  Ala  Ser  Gln  Glu  Glu  Leu
                     85                       90                       95

Arg  Ser  Pro  Arg  Gly  Ser  Val  Ala  Glu  Arg  Arg  Arg  Leu  Phe  Gln  Gln
                    100                      105                      110

Lys  Ala  Ala  Ser  Leu  Asp  Glu  Arg  Thr  Arg  Gln  Arg  Ser  Ala  Thr  Ser
               115                      120                      125

Asp  Leu  Glu  Leu  Arg  Phe  Ala  Gln  Glu  Leu  Gly  Arg  Ile  Arg  Arg  Ser
          130                      135                      140

Thr  Ser  Arg  Glu  Glu  Leu  Val  Arg  Ser  His  Glu  Ser  Leu  Arg  Ala  Thr
145                      150                      155                      160

Leu  Gln  Arg  Ala  Pro  Ser  Pro  Arg  Glu  Pro  Gly  Glu  Pro  Pro  Leu  Phe
                    165                      170                      175

Ser  Arg  Pro  Ser  Thr  Pro  Lys  Thr  Ser  Arg  Ala  Val  Ser  Pro  Ala  Ala
                    180                      185                      190
```

| | | | | | | | | | | | | | | |
|---|---|---|---|---|---|---|---|---|---|---|---|---|---|---|
|Thr|Gln|Pro|Pro|Pro|Pro|Ser|Gly|Ala|Gly|Lys|Ser|Gly|Asp|Glu|Pro|
| |195| | | |200| | | | |205| | | | |
|Gly|Arg|Pro|Arg|Ser|Arg|Gly|Pro|Val|Gly|Arg|Thr|Glu|Pro|Gly|Glu|
| |210| | | |215| | | | |220| | | | |
|Gly|Pro|Gln|Gln|Glu|Ile|Lys|Arg|Arg|Asp|Gln|Phe|Pro|Leu|Thr|Arg|
|225| | | | |230| | | | |235| | | | |240|
|Ser|Arg|Ala|Ile|Gln|Glu|Cys|Arg|Ser|Pro|Val|Pro|Pro|Tyr|Thr|Ala|
| | | | |245| | | | |250| | | | |255| |
|Asp|Pro|Pro|Glu|Ser|Arg|Thr|Lys|Ala|Pro|Ser|Gly|Arg|Lys|Arg|Glu|
| | | |260| | | | |265| | | | |270| | |
|Pro|Pro|Ala|Gln|Ala|Val|Arg|Phe|Leu|Pro|Trp|Ala|Thr|Pro|Gly|Val|
| | |275| | | | |280| | | | |285| | | |
|Glu|Asp|Ser|Val|Leu|Pro|Gln|Thr|Leu|Glu|Lys|Asn|Arg|Ala|Gly|Pro|
| |290| | | | |295| | | | |300| | | | |
|Glu|Ala|Glu|Lys|Arg|Leu|Arg|Arg|Gly|Pro|Glu|Glu|Asp|Gly|Pro|Trp|
|305| | | | |310| | | | |315| | | | |320|
|Gly|Pro|Trp|Asp|Arg|Arg|Gly|Thr|Arg|Ser|Gln|Gly|Lys|Gly|Arg|Arg|
| | | | |325| | | | |330| | | | |335| |
|Ala|Arg|Pro|Thr|Ser|Pro|Glu|Leu|Glu|Ser|Ser|Asp|Asp|Ser|Tyr|Val|
| | | |340| | | | |345| | | | |350| | |
|Ser|Ala|Gly|Glu|Glu|Pro|Leu|Glu|Ala|Pro|Val|Phe|Glu|Ile|Pro|Leu|
| | |355| | | | |360| | | | |365| | | |
|Gln|Asn|Met|Val|Val|Ala|Pro|Gly|Ala|Asp|Val|Leu|Leu|Lys|Cys|Ile|
| |370| | | | |375| | | | |380| | | | |
|Ile|Thr|Ala|Asn|Pro|Pro|Pro|Gln|Val|Ser|Trp|Lys|Lys|Asp|Gly|Ser|
|385| | | | |390| | | | |395| | | | |400|
|Met|Leu|His|Ser|Glu|Gly|Arg|Leu|Leu|Ile|Arg|Ala|Glu|Gly|Glu|Arg|
| | | | |405| | | | |410| | | | |415| |
|His|Thr|Leu|Leu|Leu|Arg|Glu|Ala|Gln|Ala|Ala|Asp|Ala|Gly|Ser|Tyr|
| | | |420| | | | |425| | | | |430| | |
|Thr|Ala|Thr|Ala|Thr|Asn|Glu|Leu|Gly|Gln|Ala|Thr|Cys|Ala|Ser|Ser|
| | |435| | | | |440| | | | |445| | | |
|Leu|Ala|Val|Arg|Pro|Gly|Gly|Ser|Thr|Ser|Pro|Phe|Ser|Ser|Pro|Ile|
| |450| | | | |455| | | | |460| | | | |
|Thr|Ser|Asp|Glu|Glu|Tyr|Leu|Ser|Pro|Pro|Glu|Glu|Phe|Pro|Glu|Pro|
|465| | | | |470| | | | |475| | | | |480|
|Gly|Glu|Thr|Trp|Pro|Arg|Thr|Pro|Thr|Met|Lys|Leu|Ser|Pro|Ser|Gln|
| | | | |485| | | | |490| | | | |495| |
|Asp|His|Asp|Ser|Ser|Asp|Ser|Ser|Ser|Lys|Ala|Pro|Pro|Thr|Phe|Lys|
| | | |500| | | | |505| | | | |510| | |
|Val|Ser|Leu|Met|Asp|Gln|Ser|Val|Arg|Glu|Gly|Gln|Asp|Val|Ile|Met|
| | |515| | | | |520| | | | |525| | | |
|Ser|Ile|Arg|Val|Gln|Gly|Glu|Pro|Lys|Pro|Val|Val|Ser|Trp|Leu|Arg|
| |530| | | | |535| | | | |540| | | | |
|Asn|Arg|Gln|Pro|Val|Arg|Pro|Asp|Gln|Arg|Arg|Phe|Ala|Glu|Glu|Ala|
|545| | | | |550| | | | |555| | | | |560|
|Glu|Gly|Gly|Leu|Cys|Arg|Leu|Arg|Ile|Leu|Ala|Ala|Glu|Arg|Gly|Asp|
| | | | |565| | | | |570| | | | |575| |
|Ala|Gly|Phe|Tyr|Thr|Cys|Lys|Ala|Val|Asn|Glu|Tyr|Gly|Ala|Arg|Gln|
| | | |580| | | | |585| | | | |590| | |
|Cys|Glu|Ala|Arg|Leu|Glu|Val|Arg|Gly| | | | | | | |
| | | |595| | | |600| | | | | | | | |

( 2 ) INFORMATION FOR SEQ ID NO:17:

( i ) SEQUENCE CHARACTERISTICS:
    ( A ) LENGTH: 2738 base pairs
    ( B ) TYPE: nucleic acid
    ( C ) STRANDEDNESS: double
    ( D ) TOPOLOGY: linear ( i i ) MOLECULE TYPE: DNA ( x i ) SEQUENCE DESCRIPTION: SEQ ID NO:17:

```
GCGATAGATA   ACCTGGTGAT   CCAAACCTGT   AATCCTAACT   ACTGTGGAGG   CTGAGATAAT     60
AACTTGCCAG   AGATACAGAG   TCAGTTCAAG   ACCACCCTAG   GCAACTAAAG   AGATCTTGTT    120
TCAGACTAAG   AAAAGAGGC    CTAGCAAGGC   CCTACATTCA   ATCCCCAGA    AACAAATGAC    180
TCAGACAGCC   CAAGTCCAGA   CTGTAAATCA   GAGACTACAG   GGACCATAC    CCCAAAGAAC    240
TCTCTAGAAT   TCCTGTGCTC   AGAAAACTTT   GAAACCCAAT   CAACCAAACT   GGGCAGTGGT    300
GTCACATGCT   TTTAATCCCA   GTACTCAGGA   GGCAGAGGCA   GGCAGATCTC   TGAGTTCAAG    360
TCCAGCCTGA   TTTACTGATT   GAGTCAAGGC   TACACAGAGA   TACCCTGTCT   CAAAAAACTA    420
ACAAGCAAAA   TACAAAAACA   AAACCAAAA    AAAAAAAAA    AAAAAAAAA    AAAATAAGAA    480
GCCCAACCAT   ATAAGAAGCA   TTTTGAAAAA   AAACTAATGT   TTGAAATCGC   TGGCATGGGG    540
TTAAAGATCT   AGTTCAAATT   GGGAAGCTGG   CTGCTGTCAT   TGGAATCACA   AGGGCTGTCG    600
AACCAGACTT   AGGGATTTAC   AGCCCTGCTC   TGAAGTTGAA   TGGCCAAGAG   CTGTGAGATT    660
CAGTGAAATC   ACCTCTTAGA   GTTCCCATCC   TCCATGAGG    ATTTGCCTAG   GTCTCAAAAC    720
TTCCATGTGC   CTAGGGATCT   CTAGAGTGCT   TTTGAAAAAA   AATTACAGTG   TTCGACTCCT    780
CACTTTAGAA   AATCAATTCT   GTAGGCTGGA   TAAGGTCTAA   GAATCTGTAT   TTCAAAACAA    840
GCCCCAAGTG   GTACCCGTGT   GGGTGGTTCA   AGCATCACGC   ACACAGTCCT   GGTGTAGATG    900
GCCTTGGGTG   ATGCTATCCG   TGTGCTAGAA   ACTGGGTGTC   TGTCGTGAAG   AGACTACAGA    960
CAGCTGGGAT   GTCAGGCTTG   ACTGGATATA   CTGGCCTGGG   GGAAATTCCT   GCTTGTGGGC   1020
TGTCTAATGC   CAGTTCTTAT   TGAATGATAC   TGGCCTGAAA   GAACTGTCCA   AAGGGCAGCT   1080
AGATGAATAG   AGTCAGCTCA   TGGAGAGCTG   GGTCAAATGT   AATGAAGTGG   TCCTTTAATG   1140
GGAAGGTTTG   GGATCAAAAG   AACACTGCCC   TTGCTGGTGT   TATCTCCCAC   AGTGAAATCT   1200
GGGTTTGTAG   ATGGATCAGG   CTTGGGATGT   TACAAAAAAA   TGGCTACAAA   GTTGCTTTAG   1260
CCCATGCGGT   CTGCAGGGCT   TGGGATTCTA   CAGCTTGGTG   GTGTACTTTG   GGGTTATGGC   1320
TGGAACAGAG   GCCACTTCTT   TTTCTCAGAG   AGGCATTCCA   TTGGAGCTTG   AGCCTGCAGC   1380
CTGACAAGCA   ATCTCGCCAA   GACTCTTGAC   CTAGGCTTGC   TGCTGATTGG   CTGGCTAGCA   1440
CCTAGGTTCT   ATTTCCCTGC   TGGCCACCAG   GGGTCTCTGA   AGCAAACATA   GACCTTTGGC   1500
AATTCGAGTT   AAATGTTTGC   CCCGCCCTCC   TTTCCTTAGC   CTGGGAGCTT   GCCTCAGCAC   1560
TGTCCAGCCT   GGAGGTGACC   CTGGAGCCAG   GAATCTAAAC   TCTGTAGAGG   GAAAGGAGTC   1620
CCCTCTTCCA   AGGGCTGTGC   CTATGACCTC   AGTATCAGCT   GGTGGCCACG   CCCCCGGCCA   1680
CAAATGCCAT   TCGGATTTCT   CTCTCCTCCC   CAACCTTGAG   ACTGCCAGCC   TGAAAGTGGG   1740
CTGTCCTCTT   GGCCCCACA    CTTCTTCATC   ACTGGCAGTG   CTGGGAACA    CAGGTCATAG   1800
CTTGGGAATG   TGGCCCTGGG   TGGAGAGAGG   GGATCAAGGA   GGGAGAGAGA   TTTGTGGCCT   1860
CTGCTCAACA   CCTCTGCTTC   TATTATTCTT   CCTGAGCCCC   TTCCCTACCC   ACTGGGTGCA   1920
AACGGAAGCT   GGGGAGGAGC   GACCATTGGG   GAGGAGCGGC   CCACACTTCC   CTAGCTTTGA   1980
GCCCTGGTGG   GCTGAGGGGT   GAGGGGCAGT   TTGCCAGCAG   AAATTCAGTA   GAACCCATGG   2040
TTGAGCAGGG   TGCAGGCCTG   TGTCCTGAAG   TACCTGCTCT   CCTGAACTTG   TCTAGGGCAG   2100
```

```
GACCTGGGAG  TCTGCAGCCA  TGGGCTCAGT  TTCCTTAGGT  TGGCAGGGGA  CAAATCTGGA    2160

AAGGAGGGTC  AAGCCCTGAC  AGTTCTTTGG  TTCTCTGTGT  CTGAAAAAGC  TGGTTGTGGC    2220

CTATTTGGGG  GTTTAAGGCT  GGCTAGTTAT  GTATTCCTAG  GTCAGGATTC  TTCTTGGTTT    2280

GGGCAAAGCA  TGGCGCTTGC  TGTGCTGTAT  GGGTCAACAC  TTCTGGCCCA  GGCAAGGATA    2340

TTAAATGCCG  CAGTGCAGTG  CCACCCCTTA  GACCCTCTG   AGGACGGGG   TCCCCACACC    2400

TGTAGTCTAG  GCCCTACTGA  TGGGTTCAGC  TCTTGTCAGT  GTCCCAAGCT  GTAAGGAGAG    2460

GAAAGGCAGA  CAGCTAGCTG  CTTGGAATGA  TCAGAGTCTA  AATTCAGCTG  GTCTGGGCTC    2520

CGCCCCTCCC  CCGTTCCTAT  TCCACCACTC  CAGGGGCTGC  TCCCTGTGGT  CTCAGCAGGC    2580

ACCACCTTCC  CAGCCAGCGC  CTGCCTGCTG  CCCAGCCTCT  TGCTGGCCAC  CCCCACCTCC    2640

TCCTTCCCCC  GCTCCTAGGC  TCACTTCCCC  TCCCCCCAGG  GCTGGCTCAG  TGCGGGGCCT    2700

CAGCTGGGTC  AGCGAGTGAG  TGGGGCTGGC  CAGGCTGA                              2738
```

( 2 ) INFORMATION FOR SEQ ID NO:18:

( i ) SEQUENCE CHARACTERISTICS:
        ( A ) LENGTH: 113 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:18:

```
Met  Lys  Leu  Ser  Pro  Ser  Gln  Asp  His  Asp  Ser  Ser  Asp  Ser  Ser
 1              5                        10                       15

Lys  Ala  Pro  Pro  Thr  Phe  Lys  Val  Ser  Leu  Met  Asp  Gln  Ser  Val  Arg
              20                        25                       30

Glu  Gly  Gln  Asp  Val  Ile  Met  Ser  Ile  Arg  Val  Gln  Gly  Glu  Pro  Lys
              35                        40                       45

Pro  Val  Val  Ser  Trp  Leu  Arg  Asn  Arg  Gln  Pro  Val  Arg  Pro  Asp  Gln
              50                        55                       60

Arg  Arg  Phe  Ala  Glu  Glu  Ala  Glu  Gly  Gly  Leu  Cys  Arg  Leu  Arg  Ile
 65                       70                       75                       80

Leu  Ala  Ala  Glu  Arg  Gly  Asp  Ala  Gly  Phe  Tyr  Thr  Cys  Lys  Ala  Val
                   85                        90                       95

Asn  Glu  Tyr  Gly  Ala  Arg  Gln  Cys  Glu  Ala  Arg  Leu  Glu  Val  Arg  Gly
                  100                       105                      110

Glu
```

( 2 ) INFORMATION FOR SEQ ID NO:19:

( i ) SEQUENCE CHARACTERISTICS:
        ( A ) LENGTH: 114 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:19:

```
Met  Lys  Xaa  Ser  Pro  Ser  Gln  Asp  Xaa  Xaa  Ser  Ser  Asp  Xaa  Xaa  Ser
 1              5                        10                       15

Lys  Ala  Pro  Pro  Thr  Phe  Lys  Val  Ser  Leu  Met  Asp  Gln  Ser  Val  Arg
              20                        25                       30

Glu  Gly  Gln  Asp  Val  Ile  Met  Ser  Ile  Arg  Val  Gln  Gly  Glu  Pro  Lys
              35                        40                       45
```

| | | | | | | | | | | | | | | |
|---|---|---|---|---|---|---|---|---|---|---|---|---|---|---|
| Pro | Val 50 | Val | Ser | Trp | Leu | Arg 55 | Asn | Arg | Gln | Pro 60 | Val | Arg | Pro | Asp | Gln |
| Arg 65 | Arg | Phe | Ala | Glu | Glu 70 | Ala | Glu | Gly | Gly | Leu 75 | Cys | Arg | Leu | Arg | Ile 80 |
| Leu | Ala | Ala | Glu | Arg 85 | Gly | Asp | Ala | Gly | Phe 90 | Tyr | Thr | Cys | Lys | Ala 95 | Val |
| Asn | Glu | Tyr | Gly 100 | Ala | Arg | Gln | Cys | Glu 105 | Ala | Arg | Leu | Glu | Val 110 | Arg | Gly |
| Glu | Xaa | | | | | | | | | | | | | | |